US012758781B2

(12) United States Patent
Ghosh

(10) Patent No.: US 12,758,781 B2
(45) Date of Patent: Oct. 13, 2026

(54) CARDIAC CONDUCTION SYSTEM ENGAGEMENT

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 931 days.

(21) Appl. No.: 17/193,794

(22) Filed: Mar. 5, 2021

(65) Prior Publication Data

US 2021/0308458 A1 Oct. 7, 2021

Related U.S. Application Data

(60) Provisional application No. 63/005,064, filed on Apr. 3, 2020.

(51) Int. Cl.

| | |
|---|---|
| ***A61N 1/362*** | (2006.01) |
| ***A61B 5/349*** | (2021.01) |
| ***A61N 1/04*** | (2006.01) |
| ***A61N 1/36*** | (2006.01) |
| ***A61N 1/37*** | (2006.01) |

(52) U.S. Cl.

CPC ............ *A61N 1/3625* (2013.01); *A61B 5/349* (2021.01); *A61N 1/0404* (2013.01); *A61N 1/36017* (2013.01); *A61N 1/36031* (2017.08); *A61N 1/3702* (2013.01)

(58) Field of Classification Search

CPC ................ A61N 1/3625; A61N 1/0404; A61N 1/36017; A61N 1/36031; A61N 1/3702

See application file for complete search history.

(56) References Cited

U.S. PATENT DOCUMENTS

| | | | |
|---|---|---|---|
| 3,835,864 | A | 9/1974 | Rasor et al. |
| 3,865,118 | A | 2/1975 | Bures |
| 3,943,936 | A | 3/1976 | Rasor et al. |
| 3,949,757 | A | 4/1976 | Sabel |
| 4,142,530 | A | 3/1979 | Wittkampf |
| 4,151,513 | A | 4/1979 | Menken et al. |
| 4,157,720 | A | 6/1979 | Greatbatch |
| RE30,366 | E | 8/1980 | Rasor et al. |
| 4,243,045 | A | 1/1981 | Mass |
| 4,250,884 | A | 2/1981 | Hartlaub et al. |

(Continued)

FOREIGN PATENT DOCUMENTS

| | | | |
|---|---|---|---|
| AU | 2008279789 | B2 | 10/2011 |
| AU | 2008329620 | B2 | 5/2014 |

(Continued)

OTHER PUBLICATIONS

US 8,886,318 B2, 11/2014, Jacobson et al. (withdrawn)

(Continued)

*Primary Examiner* — Mallika D Fairchild

(74) *Attorney, Agent, or Firm* — Mueting Raasch Group

(57) ABSTRACT

Systems and methods are described herein for determining whether a patient's cardiac conduction system or portions thereof are engaged by cardiac conduction system pacing therapy. One or more local metrics of electrical heterogeneity information may be generated based on surrogate cardiac electrical measured using a plurality of local external electrodes, which may be used to determine whether the patient's cardiac conduction system is engaged.

36 Claims, 12 Drawing Sheets

(56) References Cited

U.S. PATENT DOCUMENTS 4,256,115 A 3/1981 Bilitch
4,263,919 A 4/1981 Levin
4,280,502 A 7/1981 Baker, Jr. et al.
4,289,144 A 9/1981 Gilman
4,310,000 A 1/1982 Lindemans
4,312,354 A 1/1982 Walters
4,323,081 A 4/1982 Wiebusch
4,332,259 A 6/1982 McCorkle, Jr.
4,357,946 A 11/1982 Dutcher et al.
4,365,639 A 12/1982 Goldreyer
4,374,382 A 2/1983 Markowitz et al.
4,393,883 A 7/1983 Smyth et al.
4,440,173 A 4/1984 Hudziak et al.
4,476,868 A 10/1984 Thompson
4,479,500 A 10/1984 Smits
4,522,208 A 6/1985 Buffet
4,537,200 A 8/1985 Widrow
4,546,777 A 10/1985 Groch et al.
4,556,063 A 12/1985 Thompson et al.
4,562,841 A 1/1986 Brockway et al.
4,574,814 A 3/1986 Buffet
4,593,702 A 6/1986 Kepski et al.
4,593,955 A 6/1986 Leiber
4,630,611 A 12/1986 King
4,635,639 A 1/1987 Hakala et al.
4,674,508 A 6/1987 DeCote
4,712,554 A 12/1987 Garson
4,729,376 A 3/1988 DeCote
4,754,753 A 7/1988 King
4,759,366 A 7/1988 Callaghan
4,776,338 A 10/1988 Lekholm et al.
4,787,389 A 11/1988 Tarjan
4,793,353 A 12/1988 Borkan
4,819,662 A 4/1989 Heil et al.
4,830,006 A 5/1989 Haluska et al.
4,858,610 A 8/1989 Callaghan et al.
4,865,037 A 9/1989 Chin et al.
4,886,064 A 12/1989 Strandberg
4,887,609 A 12/1989 Cole, Jr.
4,928,688 A 5/1990 Mower
4,953,564 A 9/1990 Berthelsen
4,967,746 A 11/1990 Vandegriff
4,987,897 A 1/1991 Funke
4,989,602 A 2/1991 Sholder et al.
5,012,806 A 5/1991 De Bellis
5,036,849 A 8/1991 Hauck et al.
5,040,534 A 8/1991 Mann et al.
5,058,581 A 10/1991 Silvian
5,078,134 A 1/1992 Heilman et al.
5,109,845 A 5/1992 Yuuchi et al.
5,113,859 A 5/1992 Funke
5,113,869 A 5/1992 Nappholz et al.
5,117,824 A 6/1992 Keimel et al.
5,127,401 A 7/1992 Grievous et al.
5,133,353 A 7/1992 Hauser
5,144,950 A 9/1992 Stoop et al.
5,154,170 A 10/1992 Bennett et al.
5,170,784 A 12/1992 Ramon et al.
5,174,289 A 12/1992 Cohen
5,179,945 A 1/1993 Van Hofwegen et al.
5,193,539 A 3/1993 Schulman et al.
5,193,540 A 3/1993 Schulman et al.
5,241,961 A 9/1993 Henry
5,243,977 A 9/1993 Trabucco et al.
5,255,692 A 10/1993 Neubauer et al.
5,259,387 A 11/1993 dePinto
5,269,326 A 12/1993 Verrier
5,284,136 A 2/1994 Hauck et al.
5,300,107 A 4/1994 Stokes et al.
5,301,677 A 4/1994 Hsung
5,305,760 A 4/1994 McKown et al.
5,312,439 A 5/1994 Loeb
5,313,953 A 5/1994 Yomtov et al.
5,314,459 A 5/1994 Swanson et al.
5,318,594 A 6/1994 Limousin et al.
5,318,597 A 6/1994 Hauck et al.
5,324,316 A 6/1994 Schulman et al.
5,331,966 A 7/1994 Bennett et al.
5,334,222 A 8/1994 Salo et al.
5,342,408 A 8/1994 Decoriolis et al.
5,370,667 A 12/1994 Alt
5,372,606 A 12/1994 Lang et al.
5,376,106 A 12/1994 Stahmann et al.
5,383,915 A 1/1995 Adams
5,388,578 A 2/1995 Yomtov et al.
5,404,877 A 4/1995 Nolan et al.
5,405,367 A 4/1995 Schulman et al.
5,411,031 A 5/1995 Yomtov
5,411,525 A 5/1995 Swanson et al.
5,411,535 A 5/1995 Fujii et al.
5,456,691 A 10/1995 Snell
5,458,622 A 10/1995 Alt
5,466,246 A 11/1995 Silvian
5,468,254 A 11/1995 Hahn et al.
5,472,453 A 12/1995 Alt
5,522,866 A 6/1996 Fernald
5,540,727 A 7/1996 Tockman et al.
5,545,186 A 8/1996 Olson et al.
5,545,202 A 8/1996 Dahl et al.
5,554,177 A 9/1996 Kieval et al.
5,562,711 A 10/1996 Yerich et al.
5,571,146 A 11/1996 Jones et al.
5,591,214 A 1/1997 Lu
5,620,466 A 4/1997 Haefner et al.
5,634,938 A 6/1997 Swanson et al.
5,649,968 A 7/1997 Alt et al.
5,662,688 A 9/1997 Haefner et al.
5,674,259 A 10/1997 Gray
5,683,426 A 11/1997 Greenhut et al.
5,683,432 A 11/1997 Goedeke et al.
5,706,823 A 1/1998 Wodlinger
5,709,215 A 1/1998 Perttu et al.
5,720,770 A 2/1998 Nappholz et al.
5,728,140 A 3/1998 Salo et al.
5,728,154 A 3/1998 Crossett et al.
5,741,314 A 4/1998 Daly et al.
5,741,315 A 4/1998 Lee et al.
5,749,909 A 5/1998 Schroeppel et al.
5,752,976 A 5/1998 Duffin et al.
5,752,977 A 5/1998 Grievous et al.
5,755,736 A 5/1998 Gillberg et al.
5,759,199 A 6/1998 Snell et al.
5,774,501 A 6/1998 Halpern et al.
5,792,195 A 8/1998 Carlson et al.
5,792,202 A 8/1998 Rueter
5,792,203 A 8/1998 Schroeppel
5,792,205 A 8/1998 Alt et al.
5,792,208 A 8/1998 Gray
5,814,089 A 9/1998 Stokes et al.
5,817,130 A 10/1998 Cox et al.
5,827,216 A 10/1998 Igo et al.
5,836,985 A 11/1998 Goyal et al.
5,836,987 A 11/1998 Baumann et al.
5,842,977 A 12/1998 Lesho et al.
5,855,593 A 1/1999 Olson et al.
5,873,894 A 2/1999 Vandegriff et al.
5,891,184 A 4/1999 Lee et al.
5,897,586 A 4/1999 Molina
5,899,876 A 5/1999 Flower
5,899,928 A 5/1999 Sholder et al.
5,919,214 A 7/1999 Ciciarelli et al.
5,928,271 A 7/1999 Hess et al.
5,935,078 A 8/1999 Feierbach
5,941,906 A 8/1999 Barreras et al.
5,944,744 A 8/1999 Paul et al.
5,954,757 A 9/1999 Gray
5,978,713 A 11/1999 Prutchi et al.
5,991,660 A 11/1999 Goyal
5,991,661 A 11/1999 Park et al.
5,999,848 A 12/1999 Gord et al.
5,999,857 A 12/1999 Weijand et al.
6,016,445 A 1/2000 Baura
6,026,320 A 2/2000 Carlson et al.
6,029,085 A 2/2000 Olson et al.

(56) References Cited

U.S. PATENT DOCUMENTS

| | | | |
|---|---|---|---|
| 6,041,250 | A | 3/2000 | dePinto |
| 6,044,298 | A | 3/2000 | Salo et al. |
| 6,044,300 | A | 3/2000 | Gray |
| 6,055,454 | A | 4/2000 | Heemels |
| 6,070,104 | A | 5/2000 | Hine et al. |
| 6,073,050 | A | 6/2000 | Griffith |
| 6,076,016 | A | 6/2000 | Feierbach |
| 6,077,236 | A | 6/2000 | Cunningham |
| 6,080,187 | A | 6/2000 | Alt et al. |
| 6,083,248 | A | 7/2000 | Thompson |
| 6,106,551 | A | 8/2000 | Crossett et al. |
| 6,115,636 | A | 9/2000 | Ryan |
| 6,128,526 | A | 10/2000 | Stadler et al. |
| 6,132,456 | A | 10/2000 | Sommer et al. |
| 6,141,581 | A | 10/2000 | Olson et al. |
| 6,141,588 | A | 10/2000 | Cox et al. |
| 6,141,592 | A | 10/2000 | Pauly |
| 6,144,879 | A | 11/2000 | Gray |
| 6,162,195 | A | 12/2000 | Igo et al. |
| 6,164,284 | A | 12/2000 | Schulman et al. |
| 6,167,310 | A | 12/2000 | Grevious |
| 6,201,993 | B1 | 3/2001 | Kruse et al. |
| 6,208,894 | B1 | 3/2001 | Schulman et al. |
| 6,211,799 | B1 | 4/2001 | Post et al. |
| 6,221,011 | B1 | 4/2001 | Bardy |
| 6,240,316 | B1 | 5/2001 | Richmond et al. |
| 6,240,317 | B1 | 5/2001 | Villaseca et al. |
| 6,256,534 | B1 | 7/2001 | Dahl |
| 6,259,947 | B1 | 7/2001 | Olson et al. |
| 6,266,558 | B1 | 7/2001 | Gozani et al. |
| 6,266,567 | B1 | 7/2001 | Ishikawa et al. |
| 6,270,457 | B1 | 8/2001 | Bardy |
| 6,272,377 | B1 | 8/2001 | Sweeney et al. |
| 6,273,856 | B1 | 8/2001 | Sun et al. |
| 6,277,072 | B1 | 8/2001 | Bardy |
| 6,280,380 | B1 | 8/2001 | Bardy |
| 6,285,903 | B1 | 9/2001 | Rosenthal et al. |
| 6,285,907 | B1 | 9/2001 | Kramer et al. |
| 6,292,698 | B1 | 9/2001 | Duffin et al. |
| 6,295,473 | B1 | 9/2001 | Rosar |
| 6,297,943 | B1 | 10/2001 | Carson |
| 6,298,271 | B1 | 10/2001 | Weijand |
| 6,307,751 | B1 | 10/2001 | Bodony et al. |
| 6,312,378 | B1 | 11/2001 | Bardy |
| 6,315,721 | B2 | 11/2001 | Schulman et al. |
| 6,336,903 | B1 | 1/2002 | Bardy |
| 6,345,202 | B2 | 2/2002 | Richmond et al. |
| 6,351,667 | B1 | 2/2002 | Godie |
| 6,351,669 | B1 | 2/2002 | Hartley et al. |
| 6,353,759 | B1 | 3/2002 | Hartley et al. |
| 6,358,203 | B2 | 3/2002 | Bardy |
| 6,361,780 | B1 | 3/2002 | Ley et al. |
| 6,368,284 | B1 | 4/2002 | Bardy |
| 6,371,922 | B1 | 4/2002 | Baumann et al. |
| 6,393,316 | B1 | 5/2002 | Gillberg et al. |
| 6,398,728 | B1 | 6/2002 | Bardy |
| 6,400,982 | B2 | 6/2002 | Sweeney et al. |
| 6,400,990 | B1 | 6/2002 | Silvian |
| 6,408,208 | B1 | 6/2002 | Sun |
| 6,409,674 | B1 | 6/2002 | Brockway et al. |
| 6,411,848 | B2 | 6/2002 | Kramer et al. |
| 6,424,865 | B1 | 7/2002 | Ding |
| 6,434,429 | B1 | 8/2002 | Kraus et al. |
| 6,438,410 | B2 | 8/2002 | Hsu et al. |
| 6,438,417 | B1 | 8/2002 | Rockwell et al. |
| 6,438,421 | B1 | 8/2002 | Stahmann et al. |
| 6,440,066 | B1 | 8/2002 | Bardy |
| 6,441,747 | B1 | 8/2002 | Khair et al. |
| 6,442,426 | B1 | 8/2002 | Kroll |
| 6,442,432 | B2 | 8/2002 | Lee |
| 6,443,891 | B1 | 9/2002 | Grevious |
| 6,445,953 | B1 | 9/2002 | Bulkes et al. |
| 6,453,200 | B1 | 9/2002 | Koslar |
| 6,459,929 | B1 | 10/2002 | Hopper et al. |
| 6,470,215 | B1 | 10/2002 | Kraus et al. |
| 6,471,645 | B1 | 10/2002 | Warkentin et al. |
| 6,480,745 | B2 | 11/2002 | Nelson et al. |
| 6,487,443 | B2 | 11/2002 | Olson et al. |
| 6,490,487 | B1 | 12/2002 | Kraus et al. |
| 6,498,951 | B1 | 12/2002 | Larson et al. |
| 6,507,755 | B1 | 1/2003 | Gozani et al. |
| 6,507,759 | B1 | 1/2003 | Prutchi et al. |
| 6,508,771 | B1 | 1/2003 | Padmanabhan et al. |
| 6,512,940 | B1 | 1/2003 | Brabec et al. |
| 6,522,915 | B1 | 2/2003 | Ceballos et al. |
| 6,526,311 | B2 | 2/2003 | Begemann |
| 6,539,253 | B2 | 3/2003 | Thompson et al. |
| 6,542,775 | B2 | 4/2003 | Ding et al. |
| 6,553,258 | B2 | 4/2003 | Stahmann et al. |
| 6,561,975 | B1 | 5/2003 | Pool et al. |
| 6,564,807 | B1 | 5/2003 | Schulman et al. |
| 6,574,506 | B2 | 6/2003 | Kramer et al. |
| 6,584,351 | B1 | 6/2003 | Ekwall |
| 6,584,352 | B2 | 6/2003 | Combs et al. |
| 6,597,948 | B1 | 7/2003 | Rockwell et al. |
| 6,597,951 | B2 | 7/2003 | Kramer et al. |
| 6,622,046 | B2 | 9/2003 | Fraley et al. |
| 6,623,518 | B2 | 9/2003 | Thompson et al. |
| 6,628,985 | B2 | 9/2003 | Sweeney et al. |
| 6,647,292 | B1 | 11/2003 | Bardy et al. |
| 6,666,844 | B1 | 12/2003 | Igo et al. |
| 6,689,117 | B2 | 2/2004 | Sweeney et al. |
| 6,690,959 | B2 | 2/2004 | Thompson |
| 6,694,189 | B2 | 2/2004 | Begemann |
| 6,704,602 | B2 | 3/2004 | Berg et al. |
| 6,718,212 | B2 | 4/2004 | Parry et al. |
| 6,721,597 | B1 | 4/2004 | Bardy et al. |
| 6,738,670 | B1 | 5/2004 | Almendinger et al. |
| 6,746,797 | B2 | 6/2004 | Benson et al. |
| 6,749,566 | B2 | 6/2004 | Russ |
| 6,754,528 | B2 | 6/2004 | Bardy et al. |
| 6,758,810 | B2 | 7/2004 | Lebel et al. |
| 6,763,269 | B2 | 7/2004 | Cox |
| 6,778,860 | B2 | 8/2004 | Ostroff et al. |
| 6,788,971 | B1 | 9/2004 | Sloman et al. |
| 6,788,974 | B2 | 9/2004 | Bardy et al. |
| 6,804,558 | B2 | 10/2004 | Haller et al. |
| 6,807,442 | B1 | 10/2004 | Myklebust et al. |
| 6,847,844 | B2 | 1/2005 | Sun et al. |
| 6,869,404 | B2 | 3/2005 | Schulhauser et al. |
| 6,871,095 | B2 | 3/2005 | Stahmann et al. |
| 6,871,096 | B2 | 3/2005 | Hill |
| 6,878,112 | B2 | 4/2005 | Linberg et al. |
| 6,885,889 | B2 | 4/2005 | Chinchoy |
| 6,892,094 | B2 | 5/2005 | Ousdigian et al. |
| 6,897,788 | B2 | 5/2005 | Khair et al. |
| 6,904,315 | B2 | 6/2005 | Panken et al. |
| 6,922,592 | B2 | 7/2005 | Thompson et al. |
| 6,931,282 | B2 | 8/2005 | Esler |
| 6,931,286 | B2 | 8/2005 | Sigg et al. |
| 6,934,585 | B1 | 8/2005 | Schloss et al. |
| 6,941,169 | B2 | 9/2005 | Pappu |
| 6,957,107 | B2 | 10/2005 | Rogers et al. |
| 6,978,176 | B2 | 12/2005 | Lattouf |
| 6,980,675 | B2 | 12/2005 | Evron et al. |
| 6,985,773 | B2 | 1/2006 | Von Arx et al. |
| 6,990,375 | B2 | 1/2006 | Kloss et al. |
| 6,993,389 | B2 | 1/2006 | Ding et al. |
| 7,001,366 | B2 | 2/2006 | Ballard |
| 7,003,350 | B2 | 2/2006 | Denker et al. |
| 7,006,864 | B2 | 2/2006 | Echt et al. |
| 7,013,176 | B2 | 3/2006 | Ding et al. |
| 7,013,178 | B2 | 3/2006 | Reinke et al. |
| 7,027,871 | B2 | 4/2006 | Burnes et al. |
| 7,031,711 | B2 | 4/2006 | Brown et al. |
| 7,031,771 | B2 | 4/2006 | Brown et al. |
| 7,035,684 | B2 | 4/2006 | Lee et al. |
| 7,050,849 | B2 | 5/2006 | Echt et al. |
| 7,060,031 | B2 | 6/2006 | Webb et al. |
| 7,063,693 | B2 | 6/2006 | Guenst |
| 7,082,336 | B2 | 7/2006 | Ransbury et al. |
| 7,085,606 | B2 | 8/2006 | Flach et al. |
| 7,092,758 | B2 | 8/2006 | Sun et al. |
| 7,110,824 | B2 | 9/2006 | Amundson et al. |

(56) References Cited

U.S. PATENT DOCUMENTS 7,120,504 B2 10/2006 Osypka
7,130,681 B2 10/2006 Gebhardt et al.
7,139,613 B2 11/2006 Reinke et al.
7,142,912 B2 11/2006 Wagner et al.
7,146,225 B2 12/2006 Guenst et al.
7,146,226 B2 12/2006 Lau et al.
7,149,581 B2 12/2006 Goedeke
7,149,588 B2 12/2006 Lau et al.
7,158,839 B2 1/2007 Lau
7,162,307 B2 1/2007 Patrias
7,164,952 B2 1/2007 Lau et al.
7,177,700 B1 2/2007 Cox
7,177,704 B2 2/2007 Laske et al.
7,181,284 B2 2/2007 Burnes et al.
7,181,505 B2 2/2007 Haller et al.
7,184,830 B2 2/2007 Echt et al.
7,186,214 B2 3/2007 Ness
7,191,015 B2 3/2007 Lamson et al.
7,200,437 B1 4/2007 Nabutovsky et al.
7,200,439 B2 4/2007 Zdeblick et al.
7,206,423 B1 4/2007 Feng et al.
7,209,785 B2 4/2007 Kim et al.
7,209,790 B2 4/2007 Thompson et al.
7,211,884 B1 5/2007 Davis et al.
7,212,871 B1 5/2007 Morgan
7,226,440 B2 6/2007 Gelfand et al.
7,228,183 B2 6/2007 Sun et al.
7,231,248 B2 6/2007 Kramer et al.
7,231,253 B2 6/2007 Tidemand et al.
7,236,821 B2 6/2007 Cates et al.
7,236,829 B1 6/2007 Farazi et al.
7,254,448 B2 8/2007 Almendinger et al.
7,260,436 B2 8/2007 Kilgore et al.
7,270,669 B1 9/2007 Sra
7,272,448 B1 9/2007 Morgan et al.
7,277,755 B1 10/2007 Falkenberg et al.
7,280,872 B1 10/2007 Mosesov et al.
7,286,866 B2 10/2007 Okerlund et al.
7,288,096 B2 10/2007 Chin
7,289,847 B1 10/2007 Gill et al.
7,289,852 B2 10/2007 Helfinstine et al.
7,289,853 B1 10/2007 Campbell et al.
7,289,855 B2 10/2007 Nghiem et al.
7,302,294 B2 11/2007 Kamath et al.
7,305,266 B1 12/2007 Kroll
7,307,321 B1 12/2007 Avanzino
7,308,297 B2 12/2007 Reddy et al.
7,308,299 B2 12/2007 Burrell et al.
7,310,556 B2 12/2007 Bulkes
7,317,950 B2 1/2008 Lee
7,319,905 B1 1/2008 Morgan et al.
7,321,677 B2 1/2008 Evron et al.
7,321,798 B2 1/2008 Muhlenberg et al.
7,333,853 B2 2/2008 Mazar et al.
7,336,994 B2 2/2008 Hettrick et al.
7,346,381 B2 3/2008 Okerlund et al.
7,346,393 B2 3/2008 Spinelli et al.
7,347,819 B2 3/2008 Lebel et al.
7,366,572 B2 4/2008 Heruth et al.
7,373,207 B2 5/2008 Lattouf
7,384,403 B2 6/2008 Sherman
7,386,342 B1 6/2008 Falkenberg et al.
7,386,351 B2 6/2008 Hine et al.
7,392,090 B2 6/2008 Sweeney et al.
7,406,105 B2 7/2008 DelMain et al.
7,406,349 B2 7/2008 Seeberger et al.
7,410,497 B2 8/2008 Hastings et al.
7,425,200 B2 9/2008 Brockway et al.
7,433,739 B1 10/2008 Salys et al.
7,454,248 B2 11/2008 Burrell et al.
7,496,409 B2 2/2009 Greenhut et al.
7,496,410 B2 2/2009 Heil
7,499,743 B2 3/2009 Vass et al.
7,502,652 B2 3/2009 Gaunt et al.
7,512,448 B2 3/2009 Malick et al.
7,515,969 B2 4/2009 Tockman et al.
7,526,342 B2 4/2009 Chin et al.
7,529,589 B2 5/2009 Williams et al.
7,532,933 B2 5/2009 Hastings et al.
7,536,222 B2 5/2009 Bardy et al.
7,536,224 B2 5/2009 Ritscher et al.
7,539,541 B2 5/2009 Quiles et al.
7,544,197 B2 6/2009 Kelsch et al.
7,546,166 B2 6/2009 Michels et al.
7,558,626 B2 7/2009 Corbucci
7,558,631 B2 7/2009 Cowan et al.
7,565,190 B2 7/2009 Okerlund et al.
7,565,195 B1 7/2009 Kroll et al.
7,584,002 B2 9/2009 Burnes et al.
7,587,074 B2 9/2009 Zarkh et al.
7,590,455 B2 9/2009 Heruth et al.
7,599,730 B2 10/2009 Hunter et al.
7,606,621 B2 10/2009 Brisken et al.
7,610,088 B2 10/2009 Chinchoy
7,610,092 B2 10/2009 Cowan et al.
7,610,099 B2 10/2009 Almendinger et al.
7,610,104 B2 10/2009 Kaplan et al.
7,613,500 B2 11/2009 Vass et al.
7,616,991 B2 11/2009 Mann et al.
7,617,001 B2 11/2009 Penner et al.
7,617,007 B2 11/2009 Williams et al.
7,630,764 B2 12/2009 Ding et al.
7,630,767 B1 12/2009 Poore et al.
7,634,313 B1 12/2009 Kroll et al.
7,635,541 B2 12/2009 Scott et al.
7,637,867 B2 12/2009 Zdeblick
7,640,057 B2 12/2009 Libbus et al.
7,640,060 B2 12/2009 Zdeblick
7,647,109 B2 1/2010 Hastings et al.
7,650,186 B2 1/2010 Hastings et al.
7,657,311 B2 2/2010 Bardy et al.
7,657,313 B2 2/2010 Rom
7,668,596 B2 2/2010 Von Arx et al.
7,682,316 B2 3/2010 Anderson et al.
7,691,047 B2 4/2010 Ferrari
7,702,392 B2 4/2010 Echt et al.
7,706,879 B2 4/2010 Burnes et al.
7,713,194 B2 5/2010 Zdeblick
7,713,195 B2 5/2010 Zdeblick
7,729,783 B2 6/2010 Michels et al.
7,734,333 B2 6/2010 Ghanem et al.
7,734,343 B2 6/2010 Ransbury et al.
7,738,958 B2 6/2010 Zdeblick et al.
7,738,964 B2 6/2010 Von Arx et al.
7,742,629 B2 6/2010 Zarkh et al.
7,742,812 B2 6/2010 Ghanem et al.
7,742,816 B2 6/2010 Masoud et al.
7,742,822 B2 6/2010 Masoud et al.
7,743,151 B2 6/2010 Vallapureddy et al.
7,747,047 B2 6/2010 Okerlund et al.
7,747,335 B2 6/2010 Williams
7,751,881 B2 7/2010 Cowan et al.
7,758,521 B2 7/2010 Morris et al.
7,761,150 B2 7/2010 Ghanem et al.
7,761,164 B2 7/2010 Verhoef et al.
7,765,001 B2 7/2010 Echt et al.
7,769,452 B2 8/2010 Ghanem et al.
7,778,685 B2 8/2010 Evron et al.
7,778,686 B2 8/2010 Vass et al.
7,783,362 B2 8/2010 Whitehurst et al.
7,792,588 B2 9/2010 Harding
7,797,059 B1 9/2010 Bornzin et al.
7,801,596 B2 9/2010 Fischell et al.
7,809,438 B2 10/2010 Echt et al.
7,813,785 B2 10/2010 Okerlund et al.
7,840,281 B2 11/2010 Kveen et al.
7,844,331 B2 11/2010 Li et al.
7,844,348 B2 11/2010 Swoyer et al.
7,846,088 B2 12/2010 Ness
7,848,815 B2 12/2010 Brisken et al.
7,848,823 B2 12/2010 Drasler et al.
7,860,455 B2 12/2010 Fukumoto et al.
7,871,433 B2 1/2011 Lattouf
7,877,136 B1 1/2011 Moffitt et al.

(56) References Cited

U.S. PATENT DOCUMENTS 7,877,142 B2 1/2011 Moaddeb et al.
7,877,144 B2 1/2011 Coles, Jr. et al.
7,881,786 B2 2/2011 Jackson
7,881,791 B2 2/2011 Sambelashvili et al.
7,881,798 B2 2/2011 Miesel et al.
7,881,806 B2 2/2011 Horrigan et al.
7,881,810 B1 2/2011 Chitre et al.
7,890,173 B2 2/2011 Brisken et al.
7,890,181 B2 2/2011 Denzene et al.
7,890,192 B1 2/2011 Kelsch et al.
7,894,885 B2 2/2011 Bartal et al.
7,894,894 B2 2/2011 Stadler et al.
7,894,902 B2 2/2011 Rom
7,894,907 B2 2/2011 Cowan et al.
7,894,910 B2 2/2011 Cowan et al.
7,894,915 B1 2/2011 Chitre et al.
7,899,537 B1 3/2011 Kroll et al.
7,899,541 B2 3/2011 Cowan et al.
7,899,542 B2 3/2011 Cowan et al.
7,899,554 B2 3/2011 Williams et al.
7,901,360 B1 3/2011 Yang et al.
7,904,170 B2 3/2011 Harding
7,907,993 B2 3/2011 Ghanem et al.
7,912,544 B1 3/2011 Min et al.
7,920,928 B1 4/2011 Yang et al.
7,925,343 B1 4/2011 Min et al.
7,930,022 B2 4/2011 Zhang et al.
7,930,027 B2 4/2011 Prakash et al.
7,930,040 B1 4/2011 Kelsch et al.
7,937,135 B2 5/2011 Ghanem et al.
7,937,148 B2 5/2011 Jacobson
7,937,161 B2 5/2011 Hastings et al.
7,941,214 B2 5/2011 Kleckner et al.
7,941,218 B2 5/2011 Sambelashvili et al.
7,945,333 B2 5/2011 Jacobson
7,946,997 B2 5/2011 Hubinette
7,949,404 B2 5/2011 Hill
7,949,405 B2 5/2011 Feher
7,953,486 B2 5/2011 Daum et al.
7,953,493 B2 5/2011 Fowler et al.
7,962,202 B2 6/2011 Bhunia
7,974,702 B1 7/2011 Fain et al.
7,979,136 B2 7/2011 Young et al.
7,983,753 B2 7/2011 Severin
7,991,467 B2 8/2011 Markowitz et al.
7,991,471 B2 8/2011 Ghanem et al.
7,996,063 B2 8/2011 Vass et al.
7,996,087 B2 8/2011 Cowan et al.
8,000,791 B2 8/2011 Sunagawa et al.
8,000,807 B2 8/2011 Morris et al.
8,001,975 B2 8/2011 DiSilvestro et al.
8,002,700 B2 8/2011 Ferek-Petric et al.
8,002,718 B2 8/2011 Buchholtz et al.
8,010,209 B2 8/2011 Jacobson
8,019,419 B1 9/2011 Panescu et al.
8,019,434 B2 9/2011 Quiles et al.
8,027,727 B2 9/2011 Freeberg
8,027,729 B2 9/2011 Sunagawa et al.
8,032,219 B2 10/2011 Neumann et al.
8,036,743 B2 10/2011 Savage et al.
8,046,065 B2 10/2011 Burnes et al.
8,046,079 B2 10/2011 Bange et al.
8,046,080 B2 10/2011 Von Arx et al.
8,050,297 B2 11/2011 Delmain et al.
8,050,759 B2 11/2011 Stegemann et al.
8,050,774 B2 11/2011 Kveen et al.
8,055,345 B2 11/2011 Li et al.
8,055,350 B2 11/2011 Roberts
8,060,185 B2 11/2011 Hunter et al.
8,060,212 B1 11/2011 Rios et al.
8,065,018 B2 11/2011 Haubrich et al.
8,068,920 B2 11/2011 Gaudiani
8,073,542 B2 12/2011 Doerr
8,078,278 B2 12/2011 Penner
8,078,283 B2 12/2011 Cowan et al.
8,095,123 B2 1/2012 Gray
8,102,789 B2 1/2012 Rosar et al.
8,103,359 B2 1/2012 Reddy
8,103,361 B2 1/2012 Moser
8,105,714 B2 1/2012 Schmidt et al.
8,112,148 B2 2/2012 Giftakis et al.
8,114,021 B2 2/2012 Robertson et al.
8,121,680 B2 2/2012 Falkenberg et al.
8,123,684 B2 2/2012 Zdeblick
8,126,545 B2 2/2012 Flach et al.
8,131,334 B2 3/2012 Lu et al.
8,140,161 B2 3/2012 Willerton et al.
8,145,308 B2 3/2012 Sambelashvili et al.
8,150,521 B2 4/2012 Crowley et al.
8,160,672 B2 4/2012 Kim et al.
8,160,702 B2 4/2012 Mann et al.
8,160,704 B2 4/2012 Freeberg
8,165,694 B2 4/2012 Carbanaru et al.
8,175,715 B1 5/2012 Cox
8,180,428 B2 5/2012 Kaiser et al.
8,180,451 B2 5/2012 Hickman et al.
8,185,213 B2 5/2012 Kveen et al.
8,187,161 B2 5/2012 Li et al.
8,195,293 B2 6/2012 Limousin et al.
8,204,590 B2 6/2012 Sambelashvili et al.
8,204,595 B2 6/2012 Pianca et al.
8,204,605 B2 6/2012 Hastings et al.
8,209,014 B2 6/2012 Doerr
8,214,041 B2 7/2012 Van Gelder et al.
8,214,043 B2 7/2012 Matos
8,224,244 B2 7/2012 Kim et al.
8,229,556 B2 7/2012 Li
8,233,985 B2 7/2012 Bulkes et al.
8,262,578 B1 9/2012 Bharmi et al.
8,265,748 B2 9/2012 Liu et al.
8,265,757 B2 9/2012 Mass et al.
8,280,521 B2 10/2012 Haubrich et al.
8,285,387 B2 10/2012 Utsi et al.
8,290,598 B2 10/2012 Boon et al.
8,290,600 B2 10/2012 Hastings et al.
8,295,939 B2 10/2012 Jacobson
8,301,254 B2 10/2012 Mosesov et al.
8,315,701 B2 11/2012 Cowan et al.
8,315,708 B2 11/2012 Berthelsdorf et al.
8,321,014 B2 11/2012 Maskara et al.
8,321,021 B2 11/2012 Kisker et al.
8,321,036 B2 11/2012 Brockway et al.
8,332,036 B2 12/2012 Hastings et al.
8,335,563 B2 12/2012 Stessman
8,335,568 B2 12/2012 Heruth et al.
8,340,750 B2 12/2012 Prakash et al.
8,340,780 B2 12/2012 Hastings et al.
8,352,025 B2 1/2013 Jacobson
8,352,027 B2 1/2013 Spinelli et al.
8,352,028 B2 1/2013 Wenger
8,352,038 B2 1/2013 Mao et al.
8,359,098 B2 1/2013 Lund et al.
8,364,261 B2 1/2013 Stubbs et al.
8,364,276 B2 1/2013 Willis
8,369,959 B2 2/2013 Meskens
8,369,962 B2 2/2013 Abrahamson
8,380,320 B2 2/2013 Spital
8,383,269 B2 2/2013 Scott et al.
8,386,051 B2 2/2013 Rys
8,391,964 B2 3/2013 Musley et al.
8,391,981 B2 3/2013 Mosesov
8,391,990 B2 3/2013 Smith et al.
8,401,616 B2 3/2013 Verard et al.
8,406,874 B2 3/2013 Liu et al.
8,406,879 B2 3/2013 Shuros et al.
8,406,886 B2 3/2013 Gaunt et al.
8,406,899 B2 3/2013 Reddy et al.
8,412,352 B2 4/2013 Griswold et al.
8,417,340 B2 4/2013 Goossen
8,417,341 B2 4/2013 Freeberg
8,423,149 B2 4/2013 Hennig
8,428,716 B2 4/2013 Mullen et al.
8,428,722 B2 4/2013 Verhoef et al.
8,433,402 B2 4/2013 Ruben et al.

(56) References Cited

U.S. PATENT DOCUMENTS 8,433,409 B2 4/2013 Johnson et al.
8,433,420 B2 4/2013 Bange et al.
8,447,412 B2 5/2013 Dal Molin et al.
8,452,413 B2 5/2013 Young et al.
8,457,740 B2 6/2013 Osche
8,457,742 B2 6/2013 Jacobson
8,457,744 B2 6/2013 Janzig et al.
8,457,761 B2 6/2013 Wariar
8,467,871 B2 6/2013 Maskara
8,478,407 B2 7/2013 Demmer et al.
8,478,408 B2 7/2013 Hastings et al.
8,478,431 B2 7/2013 Griswold et al.
8,494,632 B2 7/2013 Sun et al.
8,504,156 B2 8/2013 Bonner et al.
8,509,910 B2 8/2013 Sowder et al.
8,509,916 B2 8/2013 Byrd et al.
8,515,559 B2 8/2013 Roberts et al.
8,521,268 B2 8/2013 Zhang et al.
8,525,340 B2 9/2013 Eckhardt et al.
8,527,068 B2 9/2013 Ostroff
8,532,790 B2 9/2013 Griswold
8,538,526 B2 9/2013 Stahmann et al.
8,541,131 B2 9/2013 Lund
8,543,205 B2 9/2013 Ostroff
8,547,248 B2 10/2013 Zdeblick et al.
8,548,605 B2 10/2013 Ollivier
8,554,333 B2 10/2013 Wu et al.
8,565,882 B2 10/2013 Matoes
8,565,897 B2 10/2013 Regnier et al.
8,571,678 B2 10/2013 Wang
8,577,327 B2 11/2013 Makdissi et al.
8,588,926 B2 11/2013 Moore et al.
8,594,775 B2 11/2013 Ghosh et al.
8,612,002 B2 12/2013 Faltys et al.
8,615,310 B2 12/2013 Khairkhahan et al.
8,617,082 B2 12/2013 Zhang et al.
8,626,280 B2 1/2014 Allavatam et al.
8,626,294 B2 1/2014 Sheldon et al.
8,634,908 B2 1/2014 Cowan
8,634,912 B2 1/2014 Bornzin et al.
8,634,919 B1 1/2014 Hou et al.
8,639,333 B2 1/2014 Stadler et al.
8,639,335 B2 1/2014 Peichel et al.
8,644,934 B2 2/2014 Hastings et al.
8,649,859 B2 2/2014 Smith et al.
8,670,842 B1 3/2014 Bornzin et al.
8,676,314 B2 3/2014 Maskara et al.
8,676,319 B2 3/2014 Knoll
8,676,335 B2 3/2014 Katoozi et al.
8,700,173 B2 4/2014 Edlund
8,700,181 B2 4/2014 Bomzin et al.
8,705,599 B2 4/2014 Dal Molin et al.
8,718,766 B2 5/2014 Wahlberg
8,718,773 B2 5/2014 Willis et al.
8,725,260 B2 5/2014 Shuros et al.
8,731,642 B2 5/2014 Zarkh et al.
8,738,133 B2 5/2014 Shuros et al.
8,738,147 B2 5/2014 Hastings et al.
8,744,555 B2 6/2014 Allavatam et al.
8,744,572 B1 6/2014 Greenbut et al.
8,747,314 B2 6/2014 Stahmann et al.
8,750,994 B2 6/2014 Ghosh et al.
8,750,998 B1 6/2014 Ghosh et al.
8,755,884 B2 6/2014 Demmer et al.
8,758,365 B2 6/2014 Bonner et al.
8,768,459 B2 7/2014 Ghosh et al.
8,768,483 B2 7/2014 Schmitt et al.
8,774,572 B2 7/2014 Hamamoto
8,781,582 B2 7/2014 Ziegler et al.
8,781,605 B2 7/2014 Bornzin et al.
8,788,035 B2 7/2014 Jacobson
8,788,053 B2 7/2014 Jacobson
8,798,740 B2 8/2014 Samade et al.
8,798,745 B2 8/2014 Jacobson
8,798,762 B2 8/2014 Fain et al.
8,798,770 B2 8/2014 Reddy
8,805,505 B1 8/2014 Roberts
8,805,528 B2 8/2014 Corndorf
8,812,109 B2 8/2014 Blomqvist et al.
8,818,504 B2 8/2014 Bodner et al.
8,827,913 B2 9/2014 Havel et al.
8,831,747 B1 9/2014 Min et al.
8,855,789 B2 10/2014 Jacobson
8,861,830 B2 10/2014 Brada et al.
8,868,186 B2 10/2014 Kroll
8,886,307 B2 11/2014 Sambelashvili et al.
8,886,311 B2 11/2014 Anderson et al.
8,886,339 B2 11/2014 Faltys et al.
8,903,473 B2 12/2014 Rogers et al.
8,903,513 B2 12/2014 Ollivier
8,909,336 B2 12/2014 Navarro-Paredes et al.
8,914,131 B2 12/2014 Bornzin et al.
8,923,795 B2 12/2014 Makdissi et al.
8,923,963 B2 12/2014 Bonner et al.
8,938,300 B2 1/2015 Rosero
8,942,806 B2 1/2015 Sheldon et al.
8,948,883 B2 2/2015 Eggen et al.
8,958,892 B2 2/2015 Khairkhahan et al.
8,972,228 B2 3/2015 Ghosh et al.
8,977,358 B2 3/2015 Ewert et al.
8,989,873 B2 3/2015 Locsin
8,996,109 B2 3/2015 Karst et al.
9,002,467 B2 4/2015 Smith et al.
9,008,776 B2 4/2015 Cowan et al.
9,008,777 B2 4/2015 Dianaty et al.
9,014,818 B2 4/2015 Deterre et al.
9,017,341 B2 4/2015 Bornzin et al.
9,020,611 B2 4/2015 Khairkhahan et al.
9,033,996 B1 5/2015 West
9,037,262 B2 5/2015 Regnier et al.
9,042,984 B2 5/2015 Demmer et al.
9,072,872 B2 7/2015 Asleson et al.
9,072,911 B2 7/2015 Hastings et al.
9,072,913 B2 7/2015 Jacobson
9,101,281 B2 8/2015 Reinert et al.
9,119,959 B2 9/2015 Rys et al.
9,155,882 B2 10/2015 Grubac et al.
9,168,372 B2 10/2015 Fain
9,168,380 B1 10/2015 Greenhut et al.
9,168,383 B2 10/2015 Jacobson et al.
9,180,285 B2 11/2015 Moore et al.
9,192,774 B2 11/2015 Jacobson
9,205,225 B2 12/2015 Khairkhahan et al.
9,216,285 B1 12/2015 Boling et al.
9,216,293 B2 12/2015 Berthiaume et al.
9,216,298 B2 12/2015 Jacobson
9,227,077 B2 1/2016 Jacobson
9,238,145 B2 1/2016 Wenzel et al.
9,242,102 B2 1/2016 Khairkhahan et al.
9,242,113 B2 1/2016 Smith et al.
9,248,300 B2 2/2016 Rys et al.
9,265,436 B2 2/2016 Min et al.
9,265,962 B2 2/2016 Dianaty et al.
9,272,155 B2 3/2016 Ostroff
9,278,218 B2 3/2016 Karst et al.
9,278,229 B1 3/2016 Reinke et al.
9,283,381 B2 3/2016 Grubac et al.
9,283,382 B2 3/2016 Berthiaume et al.
9,289,612 B1 3/2016 Sambelashbili et al.
9,302,115 B2 4/2016 Molin et al.
9,320,446 B2 4/2016 Gillberg et al.
9,333,364 B2 5/2016 Echt et al.
9,358,387 B2 6/2016 Suwito et al.
9,358,400 B2 6/2016 Jacobson
9,364,675 B2 6/2016 Deterre et al.
9,370,663 B2 6/2016 Moulder
9,375,580 B2 6/2016 Bonner et al.
9,375,581 B2 6/2016 Baru et al.
9,381,365 B2 7/2016 Kibler et al.
9,393,424 B2 7/2016 Demmer et al.
9,393,436 B2 7/2016 Doerr
9,399,139 B2 7/2016 Demmer et al.
9,399,140 B2 7/2016 Cho et al.
9,409,033 B2 8/2016 Jacobson

(56) References Cited

U.S. PATENT DOCUMENTS 9,427,594 B1 8/2016 Bornzin et al.
9,433,368 B2 9/2016 Stahmann et al.
9,433,780 B2 9/2016 Regnier et al.
9,457,193 B2 10/2016 Klimovitch et al.
9,474,457 B2 10/2016 Ghosh et al.
9,486,151 B2 11/2016 Ghosh et al.
9,492,668 B2 11/2016 Sheldon et al.
9,492,669 B2 11/2016 Demmer et al.
9,492,674 B2 11/2016 Schmidt et al.
9,492,677 B2 11/2016 Greenhut et al.
9,510,763 B2 12/2016 Ghosh et al.
9,511,233 B2 12/2016 Sambelashvili
9,511,236 B2 12/2016 Varady et al.
9,511,237 B2 12/2016 Deterre et al.
9,517,336 B2 12/2016 Eggen et al.
9,522,276 B2 12/2016 Shen et al.
9,522,280 B2 12/2016 Fishler et al.
9,526,522 B2 12/2016 Wood et al.
9,526,891 B2 12/2016 Eggen et al.
9,526,909 B2 12/2016 Stahmann et al.
9,533,163 B2 1/2017 Klimovitch et al.
9,561,382 B2 2/2017 Persson et al.
9,566,012 B2 2/2017 Greenhut et al.
9,579,500 B2 2/2017 Rys et al.
9,623,234 B2 4/2017 Anderson
9,636,511 B2 5/2017 Carney et al.
9,643,014 B2 5/2017 Zhang et al.
9,675,579 B2 6/2017 Rock et al.
9,707,399 B2 7/2017 Zielinski et al.
9,724,519 B2 8/2017 Demmer et al.
9,789,319 B2 10/2017 Sambelashvili
9,808,628 B2 11/2017 Sheldon et al.
9,808,633 B2 11/2017 Bonner et al.
9,877,789 B2 1/2018 Ghosh
9,901,732 B2 2/2018 Sommer et al.
9,924,884 B2 3/2018 Ghosh et al.
10,004,467 B2 6/2018 Lahm et al.
10,064,567 B2 9/2018 Ghosh et al.
10,092,744 B2 10/2018 Sommer et al.
10,099,050 B2 10/2018 Chen et al.
10,166,396 B2 1/2019 Schrock et al.
10,251,555 B2 4/2019 Ghosh et al.
10,315,028 B2 6/2019 Sommer et al.
10,406,370 B1 9/2019 Makharinsky
10,456,581 B2 10/2019 Liu et al.
10,463,853 B2 11/2019 Drake et al.
10,478,627 B2 11/2019 Muessig
2002/0032470 A1 3/2002 Linberg
2002/0035376 A1 3/2002 Bardy et al.
2002/0035377 A1 3/2002 Bardy et al.
2002/0035378 A1 3/2002 Bardy et al.
2002/0035380 A1 3/2002 Rissmann et al.
2002/0035381 A1 3/2002 Bardy et al.
2002/0042629 A1 4/2002 Bardy et al.
2002/0042630 A1 4/2002 Bardy et al.
2002/0042634 A1 4/2002 Bardy et al.
2002/0049475 A1 4/2002 Bardy et al.
2002/0049476 A1 4/2002 Bardy et al.
2002/0052636 A1 5/2002 Bardy et al.
2002/0068958 A1 6/2002 Bardy et al.
2002/0072773 A1 6/2002 Bardy et al.
2002/0082665 A1 6/2002 Haller et al.
2002/0091414 A1 7/2002 Bardy et al.
2002/0095196 A1 7/2002 Linberg
2002/0099423 A1 7/2002 Berg et al.
2002/0103510 A1 8/2002 Bardy et al.
2002/0107545 A1 8/2002 Rissmann et al.
2002/0107546 A1 8/2002 Ostroff et al.
2002/0107547 A1 8/2002 Erlinger et al.
2002/0107548 A1 8/2002 Bardy et al.
2002/0107549 A1 8/2002 Bardy et al.
2002/0107559 A1 8/2002 Sanders et al.
2002/0120299 A1 8/2002 Ostroff et al.
2002/0173830 A1 11/2002 Starkweather et al.
2002/0193846 A1 12/2002 Pool et al.
2003/0004549 A1 1/2003 Hill et al.
2003/0009203 A1 1/2003 Lebel et al.
2003/0028082 A1 2/2003 Thompson
2003/0040779 A1 2/2003 Engmark et al.
2003/0041866 A1 3/2003 Linberg et al.
2003/0045805 A1 3/2003 Sheldon et al.
2003/0083104 A1 5/2003 Bonner et al.
2003/0088278 A1 5/2003 Bardy et al.
2003/0093995 A1 5/2003 Tadayon et al.
2003/0097153 A1 5/2003 Bardy et al.
2003/0105497 A1 6/2003 Zhu et al.
2003/0114908 A1 6/2003 Flach
2003/0144701 A1 7/2003 Mehra et al.
2003/0187460 A1 10/2003 Chin et al.
2003/0187461 A1 10/2003 Chin
2003/0204233 A1 10/2003 Laske et al.
2004/0024435 A1 2/2004 Leckrone et al.
2004/0064158 A1 4/2004 Klein
2004/0068302 A1 4/2004 Rodgers et al.
2004/0087938 A1 5/2004 Leckrone et al.
2004/0088035 A1 5/2004 Guenst et al.
2004/0102830 A1 5/2004 Williams
2004/0127959 A1 7/2004 Amundson et al.
2004/0133242 A1 7/2004 Chapman et al.
2004/0147969 A1 7/2004 Mann et al.
2004/0147973 A1 7/2004 Hauser
2004/0167558 A1 8/2004 Igo et al.
2004/0167587 A1 8/2004 Thompson
2004/0172071 A1 9/2004 Bardy et al.
2004/0172077 A1 9/2004 Chinchoy
2004/0172104 A1 9/2004 Berg et al.
2004/0176817 A1 9/2004 Wahlstrand et al.
2004/0176818 A1 9/2004 Wahlstrand et al.
2004/0176830 A1 9/2004 Fang
2004/0186529 A1 9/2004 Bardy et al.
2004/0204673 A1 10/2004 Flaherty
2004/0210292 A1 10/2004 Bardy et al.
2004/0210293 A1 10/2004 Bardy et al.
2004/0210294 A1 10/2004 Bardy et al.
2004/0215308 A1 10/2004 Bardy et al.
2004/0220624 A1 11/2004 Ritscher et al.
2004/0220626 A1 11/2004 Wagner
2004/0220639 A1 11/2004 Mulligan et al.
2004/0230283 A1 11/2004 Prinzen et al.
2004/0249431 A1 12/2004 Ransbury et al.
2004/0260348 A1 12/2004 Bakken et al.
2004/0267303 A1 12/2004 Guenst
2005/0008210 A1 1/2005 Evron et al.
2005/0038477 A1 2/2005 Kramer et al.
2005/0061320 A1 3/2005 Lee et al.
2005/0070962 A1 3/2005 Echt et al.
2005/0102003 A1 5/2005 Grabek et al.
2005/0137629 A1 6/2005 Dyjach et al.
2005/0137638 A1 6/2005 Yonce et al.
2005/0137671 A1 6/2005 Liu
2005/0149138 A1 7/2005 Min et al.
2005/0165466 A1 7/2005 Morris et al.
2005/0182465 A1 8/2005 Ness
2005/0203410 A1 9/2005 Jenkins
2005/0277990 A1 12/2005 Ostroff et al.
2005/0283208 A1 12/2005 Von Arx et al.
2005/0288743 A1 12/2005 Ahn et al.
2006/0042830 A1 3/2006 Maghribi et al.
2006/0052829 A1 3/2006 Sun et al.
2006/0052830 A1 3/2006 Spinelli et al.
2006/0064135 A1 3/2006 Brockway
2006/0064149 A1 3/2006 Belacazar et al.
2006/0074285 A1 4/2006 Zarkh et al.
2006/0085039 A1 4/2006 Hastings et al.
2006/0085041 A1 4/2006 Hastings et al.
2006/0085042 A1 4/2006 Hastings et al.
2006/0095078 A1 5/2006 Tronnes
2006/0106442 A1 5/2006 Richardson et al.
2006/0116746 A1 6/2006 Chin
2006/0135999 A1 6/2006 Bodner et al.
2006/0136004 A1 6/2006 Cowan et al.
2006/0161061 A1 7/2006 Echt et al.
2006/0161205 A1 7/2006 Mitrani et al.
2006/0200002 A1 9/2006 Guenst

(56) References Cited

U.S. PATENT DOCUMENTS

2006/0206151 A1 9/2006 Lu
2006/0212079 A1 9/2006 Routh et al.
2006/0235478 A1 10/2006 Van Gelder et al.
2006/0241701 A1 10/2006 Markowitz et al.
2006/0241705 A1 10/2006 Neumann et al.
2006/0247672 A1 11/2006 Vidlund et al.
2006/0259088 A1 11/2006 Pastore et al.
2006/0265018 A1 11/2006 Smith et al.
2007/0004979 A1 1/2007 Wojciechowicz et al.
2007/0016098 A1 1/2007 Kim et al.
2007/0027508 A1 2/2007 Cowan
2007/0049975 A1 3/2007 Cates et al.
2007/0078490 A1 4/2007 Cowan et al.
2007/0088394 A1 4/2007 Jacobson
2007/0088396 A1 4/2007 Jacobson
2007/0088397 A1 4/2007 Jacobson
2007/0088398 A1 4/2007 Jacobson
2007/0088405 A1 4/2007 Jaconson
2007/0135882 A1 6/2007 Drasler et al.
2007/0135883 A1 6/2007 Drasler et al.
2007/0150037 A1 6/2007 Hastings et al.
2007/0150038 A1 6/2007 Hastings et al.
2007/0156190 A1 7/2007 Cinbis
2007/0219525 A1 9/2007 Gelfand et al.
2007/0219590 A1 9/2007 Hastings et al.
2007/0225545 A1 9/2007 Ferrari
2007/0233206 A1 10/2007 Frikart et al.
2007/0233216 A1 10/2007 Liu
2007/0239244 A1 10/2007 Morgan et al.
2007/0255376 A1 11/2007 Michels et al.
2007/0276444 A1 11/2007 Gelbart et al.
2007/0293900 A1 12/2007 Sheldon et al.
2007/0293904 A1 12/2007 Gelbart et al.
2007/0299475 A1 12/2007 Levin et al.
2008/0004663 A1 1/2008 Jorgenson
2008/0021505 A1 1/2008 Hastings et al.
2008/0021519 A1 1/2008 De Geest et al.
2008/0021532 A1 1/2008 Kveen et al.
2008/0065183 A1 3/2008 Whitehurst et al.
2008/0065185 A1 3/2008 Worley
2008/0071318 A1 3/2008 Brooke et al.
2008/0103539 A1 5/2008 Stegemann et al.
2008/0109054 A1 5/2008 Hastings et al.
2008/0119911 A1 5/2008 Rosero
2008/0130670 A1 6/2008 Kim et al.
2008/0154139 A1 6/2008 Shuros et al.
2008/0154322 A1 6/2008 Jackson et al.
2008/0228234 A1 9/2008 Stancer
2008/0234771 A1 9/2008 Chinchoy et al.
2008/0243217 A1 10/2008 Wildon
2008/0269814 A1 10/2008 Rosero
2008/0269816 A1 10/2008 Prakash et al.
2008/0269823 A1 10/2008 Burnes et al.
2008/0269825 A1 10/2008 Chinchoy et al.
2008/0275518 A1 11/2008 Ghanem et al.
2008/0275519 A1 11/2008 Ghanem et al.
2008/0288008 A1 11/2008 Lee
2008/0288039 A1 11/2008 Reddy
2008/0294208 A1 11/2008 Willis et al.
2008/0294210 A1 11/2008 Rosero
2008/0294229 A1 11/2008 Friedman et al.
2008/0306359 A1 12/2008 Zdeblick et al.
2009/0018599 A1 1/2009 Hastings et al.
2009/0024180 A1 1/2009 Kisker et al.
2009/0036941 A1 2/2009 Corbucci
2009/0048646 A1 2/2009 Katoozi et al.
2009/0062895 A1 3/2009 Stahmann et al.
2009/0082827 A1 3/2009 Kveen et al.
2009/0082828 A1 3/2009 Ostroff
2009/0088813 A1 4/2009 Brockway et al.
2009/0099619 A1 4/2009 Lessmeier et al.
2009/0131907 A1 5/2009 Chin et al.
2009/0135886 A1 5/2009 Robertson et al.
2009/0143835 A1 6/2009 Pastore et al.
2009/0171408 A1 7/2009 Solem
2009/0171414 A1 7/2009 Kelly et al.
2009/0204163 A1 8/2009 Shuros et al.
2009/0204170 A1 8/2009 Hastings et al.
2009/0210024 A1 8/2009 Jason
2009/0216292 A1 8/2009 Pless et al.
2009/0234407 A1 9/2009 Hastings et al.
2009/0234411 A1 9/2009 Sambelashvili et al.
2009/0234412 A1 9/2009 Sambelashvili
2009/0234413 A1 9/2009 Sambelashvili et al.
2009/0234414 A1 9/2009 Sambelashvili et al.
2009/0234415 A1 9/2009 Sambelashvili et al.
2009/0248103 A1 10/2009 Sambelashvili et al.
2009/0259272 A1 10/2009 Reddy et al.
2009/0266573 A1 10/2009 Engmark et al.
2009/0275998 A1 11/2009 Burnes et al.
2009/0275999 A1 11/2009 Burnes et al.
2009/0299447 A1 12/2009 Jensen et al.
2010/0013668 A1 1/2010 Kantervik
2010/0016911 A1 1/2010 Willis et al.
2010/0016914 A1 1/2010 Mullen et al.
2010/0023078 A1 1/2010 Dong et al.
2010/0023085 A1 1/2010 Wu et al.
2010/0030061 A1 2/2010 Canfield et al.
2010/0030327 A1 2/2010 Chatel
2010/0042108 A1 2/2010 Hibino
2010/0063375 A1 3/2010 Kassab et al.
2010/0063562 A1 3/2010 Cowan et al.
2010/0065871 A1 3/2010 Govari et al.
2010/0094367 A1 4/2010 Sen
2010/0114209 A1 5/2010 Krause et al.
2010/0114214 A1 5/2010 Morelli et al.
2010/0125281 A1 5/2010 Jacobson et al.
2010/0152798 A1 6/2010 Sanghera et al.
2010/0168761 A1 7/2010 Kassab et al.
2010/0168819 A1 7/2010 Freeberg
2010/0185250 A1 7/2010 Rom
2010/0198288 A1 8/2010 Ostroff
2010/0198291 A1 8/2010 Sambelashvili et al.
2010/0198304 A1 8/2010 Wang
2010/0217367 A1 8/2010 Belson
2010/0228308 A1 9/2010 Cowan et al.
2010/0234906 A1 9/2010 Kob
2010/0234924 A1 9/2010 Willis
2010/0241185 A1 9/2010 Mahapatra et al.
2010/0249729 A1 9/2010 Morris et al.
2010/0286541 A1 11/2010 Musley et al.
2010/0286626 A1 11/2010 Petersen
2010/0286744 A1 11/2010 Echt et al.
2010/0298841 A1 11/2010 Prinzen et al.
2010/0312309 A1 12/2010 Harding
2010/0318147 A1 12/2010 Forslund
2011/0022113 A1 1/2011 Ideblick et al.
2011/0071586 A1 3/2011 Jacobson
2011/0077708 A1 3/2011 Ostroff
2011/0106202 A1 5/2011 Ding et al.
2011/0112398 A1 5/2011 Zarkh et al.
2011/0112600 A1 5/2011 Cowan et al.
2011/0118588 A1 5/2011 Komblau et al.
2011/0118810 A1 5/2011 Cowan et al.
2011/0137187 A1 6/2011 Yang et al.
2011/0144720 A1 6/2011 Cowan et al.
2011/0152970 A1 6/2011 Jollota et al.
2011/0160558 A1 6/2011 Rassatt et al.
2011/0160565 A1 6/2011 Stubbs
2011/0160801 A1 6/2011 Markowitz et al.
2011/0160806 A1 6/2011 Lyden et al.
2011/0166620 A1 7/2011 Cowan et al.
2011/0166621 A1 7/2011 Cowan et al.
2011/0184491 A1 7/2011 Kivi
2011/0190835 A1 8/2011 Brockway et al.
2011/0190841 A1 8/2011 Sambelashvili et al.
2011/0196444 A1 8/2011 Prakash et al.
2011/0208260 A1 8/2011 Jacobson
2011/0218587 A1 9/2011 Jacobson
2011/0230734 A1 9/2011 Fain et al.
2011/0237967 A1 9/2011 Moore et al.
2011/0245890 A1 10/2011 Brisben et al.
2011/0251660 A1 10/2011 Griswold
2011/0251662 A1 10/2011 Griswold et al.

(56) References Cited

U.S. PATENT DOCUMENTS

2011/0270099 A1 11/2011 Ruben et al.
2011/0270339 A1 11/2011 Murray, III et al.
2011/0270340 A1 11/2011 Pellegrini et al.
2011/0276102 A1 11/2011 Cohen
2011/0282423 A1 11/2011 Jacobson
2012/0004527 A1 1/2012 Thompson et al.
2012/0029323 A1 2/2012 Zhao
2012/0035685 A1 2/2012 Saha et al.
2012/0041508 A1 2/2012 Rousso et al.
2012/0059433 A1 3/2012 Cowan et al.
2012/0059436 A1 3/2012 Fontaine et al.
2012/0065500 A1 3/2012 Rogers et al.
2012/0078129 A1 3/2012 Bailin
2012/0078322 A1 3/2012 Dal Molin et al.
2012/0089198 A1 4/2012 Ostroff
2012/0089214 A1 4/2012 Kroll et al.
2012/0093245 A1 4/2012 Makdissi et al.
2012/0095521 A1 4/2012 Hintz
2012/0095539 A1 4/2012 Khairkhahan et al.
2012/0101540 A1 4/2012 O'Brien et al.
2012/0101553 A1 4/2012 Reddy
2012/0109148 A1 5/2012 Bonner et al.
2012/0109149 A1 5/2012 Bonner et al.
2012/0109235 A1 5/2012 Sheldon et al.
2012/0109236 A1 5/2012 Jacobson et al.
2012/0109259 A1 5/2012 Bond et al.
2012/0116489 A1 5/2012 Khairkhahan et al.
2012/0150251 A1 6/2012 Giftakis et al.
2012/0158111 A1 6/2012 Khairkhahan et al.
2012/0165827 A1 6/2012 Khairkhahan et al.
2012/0172690 A1 7/2012 Anderson et al.
2012/0172891 A1 7/2012 Lee
2012/0172892 A1 7/2012 Grubac et al.
2012/0172942 A1 7/2012 Berg
2012/0179221 A1 7/2012 Reddy et al.
2012/0197350 A1 8/2012 Roberts et al.
2012/0197373 A1 8/2012 Khairkhahan et al.
2012/0215285 A1 8/2012 Tahmasian et al.
2012/0232478 A1 9/2012 Haslinger
2012/0232563 A1 9/2012 Williams
2012/0232565 A1 9/2012 Kveen et al.
2012/0245665 A1 9/2012 Friedman et al.
2012/0263218 A1 10/2012 Dal Molin et al.
2012/0277600 A1 11/2012 Greenhut
2012/0277606 A1 11/2012 Ellingson et al.
2012/0283587 A1 11/2012 Gosh et al.
2012/0283795 A1 11/2012 Stancer et al.
2012/0283807 A1 11/2012 Deterre et al.
2012/0284003 A1 11/2012 Gosh et al.
2012/0290025 A1 11/2012 Keimel
2012/0296228 A1 11/2012 Zhang et al.
2012/0296381 A1 11/2012 Matos
2012/0303082 A1 11/2012 Dong et al.
2012/0316613 A1 12/2012 Keefe et al.
2013/0012151 A1 1/2013 Hankins
2013/0013017 A1 1/2013 Mullen et al.
2013/0023975 A1 1/2013 Locsin
2013/0035748 A1 2/2013 Bonner et al.
2013/0041422 A1 2/2013 Jacobson
2013/0053906 A1 2/2013 Ghosh et al.
2013/0053908 A1 2/2013 Smith et al.
2013/0053915 A1 2/2013 Holmstrom et al.
2013/0053921 A1 2/2013 Bonner et al.
2013/0060298 A1 3/2013 Splett et al.
2013/0066169 A1 3/2013 Rys et al.
2013/0072770 A1 3/2013 Rao et al.
2013/0079798 A1 3/2013 Tran et al.
2013/0079861 A1 3/2013 Reinert et al.
2013/0085350 A1 4/2013 Schugt et al.
2013/0085403 A1 4/2013 Gunderson et al.
2013/0085550 A1 4/2013 Polefko et al.
2013/0096649 A1 4/2013 Martin et al.
2013/0103047 A1 4/2013 Steingisser et al.
2013/0103109 A1 4/2013 Jacobson
2013/0110008 A1 5/2013 Bourg et al.
2013/0110127 A1 5/2013 Bornzin et al.
2013/0110192 A1 5/2013 Tran et al.
2013/0110219 A1 5/2013 Bornzin et al.
2013/0116529 A1 5/2013 Min et al.
2013/0116738 A1 5/2013 Samade et al.
2013/0116739 A1 5/2013 Brada et al.
2013/0116740 A1 5/2013 Bornzin et al.
2013/0116741 A1 5/2013 Bornzin et al.
2013/0123872 A1 5/2013 Bornzin et al.
2013/0123875 A1 5/2013 Varady et al.
2013/0131591 A1 5/2013 Berthiaume et al.
2013/0131693 A1 5/2013 Berthiaume et al.
2013/0131750 A1 5/2013 Stadler et al.
2013/0131751 A1 5/2013 Stadler et al.
2013/0138006 A1 5/2013 Bornzin et al.
2013/0150695 A1 6/2013 Biela et al.
2013/0150911 A1 6/2013 Perschbacher et al.
2013/0150912 A1 6/2013 Perschbacher et al.
2013/0184776 A1 7/2013 Shuros et al.
2013/0196703 A1 8/2013 Masoud et al.
2013/0197599 A1 8/2013 Sambelashvili et al.
2013/0197609 A1 8/2013 Moore et al.
2013/0231710 A1 9/2013 Jacobson
2013/0238072 A1 9/2013 Deterre et al.
2013/0238073 A1 9/2013 Makdissi et al.
2013/0253342 A1 9/2013 Griswold et al.
2013/0253343 A1 9/2013 Walfhauser et al.
2013/0253344 A1 9/2013 Griswold et al.
2013/0253345 A1 9/2013 Griswold et al.
2013/0253346 A1 9/2013 Griswold et al.
2013/0253347 A1 9/2013 Griswold et al.
2013/0261497 A1 10/2013 Pertijs et al.
2013/0265144 A1 10/2013 Banna et al.
2013/0268017 A1 10/2013 Zhang et al.
2013/0268042 A1 10/2013 Hastings et al.
2013/0274828 A1 10/2013 Willis
2013/0274847 A1 10/2013 Ostroff
2013/0282070 A1 10/2013 Cowan et al.
2013/0282073 A1 10/2013 Cowan et al.
2013/0296727 A1 11/2013 Sullivan et al.
2013/0303872 A1 11/2013 Taff et al.
2013/0324825 A1 12/2013 Ostroff et al.
2013/0325081 A1 12/2013 Karst et al.
2013/0345770 A1 12/2013 Dianaty et al.
2014/0012344 A1 1/2014 Hastings et al.
2014/0018876 A1 1/2014 Ostroff
2014/0018877 A1 1/2014 Demmer et al.
2014/0031836 A1 1/2014 Ollivier
2014/0039591 A1 2/2014 Drasler et al.
2014/0043146 A1 2/2014 Makdissi et al.
2014/0046395 A1 2/2014 Regnier et al.
2014/0046420 A1 2/2014 Moore et al.
2014/0058240 A1 2/2014 Mothilal et al.
2014/0058494 A1 2/2014 Ostroff et al.
2014/0074114 A1 3/2014 Khairkhahan et al.
2014/0074186 A1 3/2014 Faltys et al.
2014/0094891 A1 4/2014 Pare et al.
2014/0100627 A1 4/2014 Min
2014/0107723 A1 4/2014 Hou et al.
2014/0114173 A1 4/2014 Bar-Tal et al.
2014/0114372 A1 4/2014 Ghosh et al.
2014/0121719 A1 5/2014 Bonner et al.
2014/0121720 A1 5/2014 Bonner et al.
2014/0121722 A1 5/2014 Sheldon et al.
2014/0128935 A1 5/2014 Kumar et al.
2014/0135865 A1 5/2014 Hastings et al.
2014/0142648 A1 5/2014 Smith et al.
2014/0148675 A1 5/2014 Nordstrom et al.
2014/0148815 A1 5/2014 Wenzel et al.
2014/0155950 A1 6/2014 Hastings et al.
2014/0169162 A1 6/2014 Romano et al.
2014/0172060 A1 6/2014 Bornzin et al.
2014/0180306 A1 6/2014 Grubac et al.
2014/0180366 A1 6/2014 Edlund
2014/0207149 A1 7/2014 Hastings et al.
2014/0207210 A1 7/2014 Willis et al.
2014/0214104 A1 7/2014 Greenhut et al.
2014/0222098 A1 8/2014 Baru et al.
2014/0222109 A1 8/2014 Moulder

(56) References Cited

U.S. PATENT DOCUMENTS

2014/0228913 A1 8/2014 Molin et al.
2014/0236172 A1 8/2014 Hastings et al.
2014/0243848 A1 8/2014 Auricchio et al.
2014/0255298 A1 9/2014 Cole et al.
2014/0257324 A1 9/2014 Fain
2014/0257422 A1 9/2014 Herken
2014/0257444 A1 9/2014 Cole et al.
2014/0276929 A1 9/2014 Foster et al.
2014/0303704 A1 10/2014 Suwito et al.
2014/0309706 A1 10/2014 Jacobson
2014/0323882 A1 10/2014 Ghosh et al.
2014/0323892 A1 10/2014 Ghosh et al.
2014/0330208 A1 11/2014 Christie et al.
2014/0330287 A1 11/2014 Thompson-Nauman et al.
2014/0330326 A1 11/2014 Thompson-Nauman et al.
2014/0339570 A1 11/2014 Mollard et al.
2014/0358135 A1 12/2014 Sambelashvili et al.
2014/0371832 A1 12/2014 Ghosh
2014/0371833 A1 12/2014 Ghosh et al.
2014/0379041 A1 12/2014 Foster
2015/0025612 A1 1/2015 Haasl et al.
2015/0039041 A1 2/2015 Smith et al.
2015/0051609 A1 2/2015 Schmidt et al.
2015/0051610 A1 2/2015 Schmidt et al.
2015/0051611 A1 2/2015 Schmidt et al.
2015/0051612 A1 2/2015 Schmidt et al.
2015/0051613 A1 2/2015 Schmidt et al.
2015/0051614 A1 2/2015 Schmidt et al.
2015/0051615 A1 2/2015 Schmidt et al.
2015/0051616 A1 2/2015 Haasl et al.
2015/0051682 A1 2/2015 Schmidt et al.
2015/0057520 A1 2/2015 Foster et al.
2015/0057558 A1 2/2015 Stahmann et al.
2015/0057721 A1 2/2015 Stahmann et al.
2015/0088155 A1 3/2015 Foster et al.
2015/0105836 A1 4/2015 Bonner et al.
2015/0142070 A1 5/2015 Sambelashvili
2015/0148697 A1 5/2015 Burnes et al.
2015/0149096 A1 5/2015 Soykan
2015/0157861 A1 6/2015 Aghassian
2015/0173655 A1 6/2015 Demmer et al.
2015/0190638 A1 7/2015 Smith et al.
2015/0196756 A1 7/2015 Stahmann et al.
2015/0196757 A1 7/2015 Stahmann et al.
2015/0196758 A1 7/2015 Stahmann et al.
2015/0196769 A1 7/2015 Stahmann et al.
2015/0217119 A1 8/2015 Nikolski et al.
2015/0221898 A1 8/2015 Chi et al.
2015/0224315 A1 8/2015 Stahmann
2015/0224320 A1 8/2015 Stahmann
2015/0258345 A1 9/2015 Smith et al.
2015/0290468 A1 10/2015 Zhang
2015/0297905 A1 10/2015 Greenhut et al.
2015/0297907 A1 10/2015 Zhang
2015/0305637 A1 10/2015 Greenhut et al.
2015/0305638 A1 10/2015 Zhang
2015/0305639 A1 10/2015 Greenhut et al.
2015/0305640 A1 10/2015 Reinke et al.
2015/0305641 A1 10/2015 Stadler et al.
2015/0305642 A1 10/2015 Reinke et al.
2015/0305695 A1 10/2015 Lahm et al.
2015/0306374 A1 10/2015 Seifert et al.
2015/0306375 A1 10/2015 Marshall et al.
2015/0306406 A1 10/2015 Crutchfield et al.
2015/0306407 A1 10/2015 Crutchfield et al.
2015/0306408 A1 10/2015 Greenhut et al.
2015/0321016 A1 11/2015 O'Brien et al.
2015/0328459 A1 11/2015 Chin et al.
2015/0335894 A1 11/2015 Bornzin et al.
2016/0015287 A1 1/2016 Anderson et al.
2016/0015322 A1 1/2016 Anderson et al.
2016/0023000 A1 1/2016 Cho et al.
2016/0030757 A1 2/2016 Jacobson
2016/0033177 A1 2/2016 Barot et al.
2016/0045738 A1 2/2016 Ghosh et al.
2016/0045744 A1 2/2016 Gillberg et al.
2016/0051821 A1 2/2016 Sambelashvili et al.
2016/0059002 A1 3/2016 Grubac et al.
2016/0067486 A1 3/2016 Brown et al.
2016/0067487 A1 3/2016 Demmer et al.
2016/0067490 A1 3/2016 Carney et al.
2016/0110856 A1 4/2016 Hoof et al.
2016/0114161 A1 4/2016 Amblard et al.
2016/0121127 A1 5/2016 Klimovitch et al.
2016/0121128 A1 5/2016 Fishler et al.
2016/0121129 A1 5/2016 Persson et al.
2016/0129239 A1 5/2016 Anderson
2016/0213919 A1 7/2016 Suwito et al.
2016/0213937 A1 7/2016 Reinke et al.
2016/0213939 A1 7/2016 Carney et al.
2016/0228026 A1 8/2016 Jackson
2016/0317825 A1 11/2016 Jacobson
2016/0367823 A1 12/2016 Cowan et al.
2017/0014629 A1 1/2017 Ghosh et al.
2017/0035315 A1 2/2017 Jackson
2017/0043173 A1 2/2017 Sharma et al.
2017/0043174 A1 2/2017 Greenhut et al.
2017/0056670 A1 3/2017 Sheldon et al.
2017/0182327 A1 6/2017 Liu
2017/0189681 A1 7/2017 Anderson
2017/0209689 A1 7/2017 Chen
2017/0216575 A1 8/2017 Asleson et al.
2017/0246461 A1 8/2017 Ghosh
2017/0303840 A1 10/2017 Stadler et al.
2017/0304624 A1 10/2017 Friedman et al.
2017/0326369 A1 11/2017 Koop et al.
2017/0326372 A1 11/2017 Koop et al.
2017/0340885 A1 11/2017 Sambelashvili
2018/0008829 A1 1/2018 An et al.
2018/0021567 A1 1/2018 An et al.
2018/0021581 A1 1/2018 An et al.
2018/0021582 A1 1/2018 An et al.
2018/0050208 A1 2/2018 Shuros et al.
2018/0078773 A1 3/2018 Thakur et al.
2018/0078779 A1 3/2018 An et al.
2018/0117324 A1 5/2018 Schilling et al.
2018/0140848 A1 5/2018 Stahmann
2018/0178007 A1 6/2018 Shuros et al.
2018/0212451 A1 7/2018 Schmidt et al.
2018/0263522 A1 9/2018 Ghosh et al.
2018/0264262 A1 9/2018 Haasl et al.
2018/0264272 A1 9/2018 Haasl et al.
2018/0264273 A1 9/2018 Haasl et al.
2018/0264274 A1 9/2018 Haasl et al.
2018/0280686 A1 10/2018 Shuros et al.
2018/0326215 A1 11/2018 Ghosh
2019/0030346 A1 1/2019 Li
2019/0038906 A1 2/2019 Koop et al.
2019/0083779 A1 3/2019 Yang et al.
2019/0083800 A1 3/2019 Yang et al.
2019/0083801 A1 3/2019 Yang et al.
2019/0192860 A1 6/2019 Ghosh et al.
2019/0192863 A1 6/2019 Koop et al.
2019/0269926 A1 9/2019 Ghosh
2019/0290905 A1 9/2019 Yang et al.
2019/0290909 A1 9/2019 Ghosh
2019/0290910 A1 9/2019 Yang et al.
2019/0298990 A1 10/2019 De Kock et al.
2019/0314636 A1 10/2019 Shuros et al.
2019/0351236 A1 11/2019 Koop
2020/0069949 A1 3/2020 Ghosh

FOREIGN PATENT DOCUMENTS

AU 2014203793 A1 7/2014
CN 202933393 5/2013
EP 0362611 A1 4/1990
EP 0459 239 A2 12/1991
EP 0 728 497 A2 8/1996
EP 1 541 191 A1 6/2005
EP 1 702 648 A1 9/2006
EP 1 904 166 B1 6/2011
EP 2 452 721 A1 5/2012
EP 2 471 452 A1 7/2012

(56) References Cited

FOREIGN PATENT DOCUMENTS

| | | | |
|---|---|---|---|
| EP | 2 662 113 | A2 | 11/2013 |
| EP | 1 703 944 | B1 | 7/2015 |
| JP | 2005245215 | | 9/2005 |
| WO | WO 95/00202 | | 1/1995 |
| WO | WO 96/36134 | | 11/1996 |
| WO | WO 97/24981 | | 7/1997 |
| WO | WO 02/22206 | A1 | 3/2002 |
| WO | WO 03/092800 | A1 | 11/2003 |
| WO | WO 2005/000206 | A2 | 1/2005 |
| WO | WO 2005/042089 | A1 | 5/2005 |
| WO | WO 2006/086435 | A2 | 8/2006 |
| WO | WO 2006/113659 | A1 | 10/2006 |
| WO | WO 2007/073435 | A1 | 6/2007 |
| WO | WO 2007/075974 | A2 | 7/2007 |
| WO | WO 2009/006531 | A1 | 1/2009 |
| WO | WO 2013/080038 | A2 | 6/2013 |
| WO | WO 2013/098644 | A2 | 7/2013 |
| WO | WO 2015/081221 | A1 | 6/2015 |
| WO | WO 2016/011042 | A1 | 1/2016 |
| WO | WO 2016/077099 | A1 | 5/2016 |
| WO | WO 2016/110856 | A1 | 7/2016 |
| WO | WO 2016/171891 | A1 | 10/2016 |
| WO | WO 2017/075193 | A1 | 5/2017 |
| WO | WO 2018/009569 | A1 | 1/2018 |
| WO | WO 2018/017226 | A1 | 1/2018 |
| WO | WO 2018/017361 | A1 | 1/2018 |
| WO | WO 2018/035343 | A1 | 2/2018 |
| WO | WO 2018/081519 | A1 | 5/2018 |

OTHER PUBLICATIONS

U.S. Appl. No. 10/039,305, filed Aug. 27, 2019, Asleson et al.

U.S. Appl. No. 16/944,230, filed Jul. 31, 2020, Gelfman et al.

U.S. Appl. No. 17/031,182, filed Sep. 24, 2020, Ghosh et al.

U.S. Appl. No. 17/070,361, filed Oct. 14, 2020, Hine et al.

U.S. Appl. No. 63/059,878, filed Jul. 31, 2020, Whitman et al.

http://www.isrctn.com/ISRCTN47824547, public posting published Aug. 2019.

Abed et al., "Obesity results in progressive atrial structural and electrical remodeling: Implications for atrial fibrillation," *Heart Rhythm Society*, Jan. 2013; 10(1):90-100.

Adragão et al., "Ablation of pulmonary vein foci for the treatment of atrial fibrillation; percutaneous electroanatomical guided approach," *Europace*, Oct. 2002; 4(4):391-9.

Aliot et al., "Arrhythmia detection by dual-chamber implantable cardioverter defibrillators: A review of current algorithms," *Europace*, Jul. 2004; 6(4):273-86.

Amirahmadi et al., "Ventricular Tachycardia Caused by Mesothelial Cyst," *Indian Pacing and Electrophysiology Journal*, 2013; 13(1):43-44.

Ammirabile et al., "Pitx2 confers left morphological, molecular, and functional identity to the sinus venosus myocardium," *Cardiovasc Res.*, Feb. 2012; 93(2):291-301.

Anderson et al., "Left bundle branch block and the evolving role of QRS morphology in selection of patients for cardiac resynchronization", Journal of Interventional Cardio Electrophysiology, vol. 52, No. 3. Aug. 20. 2018, pp. 353-374.

Anfinsen, "Non-pharmacological Treatment of Atrial Fibrillation," *Indian Pacing and Electrophysiology Journal*, Jan. 2002; 2(1):4-14.

Anné et al., "Ablation of post-surgical intra-atrial reentrant Tachycardia," *European Heart Journal*, 2002; 23:169-1616.

Arenal et al., "Dominant frequency differences in atrial fibrillation patients with and without left ventricular systolic dysfunction," *Europace*, Apr. 2009; 11(4):450-457.

Arriagada et al., "Predictors of arrhythmia recurrence in patients with lone atrial fibrillation," *Europace*, Jan. 2008; 10(1):9-14.

Asirvatham et al., "Cardiac Anatomic Considerations in Pediatric Electrophysiology," *Indian Pacing and Electrophysiology Journal*, Apr. 2008; 8(Suppl 1):S75-S91.

Asirvatham et al., "Intramyocardial Pacing and Sensing for the Enhancement of Cardiac Stimulation and Sensing Specificity," *Pacing Clin. Electrophysiol.*, Jun. 2007; 30(6):748-754.

Asirvatham et al., "Letter to the Editor," *J Cardiovasc Electrophysiol.*, Mar. 2010; 21(3): E77.

Balmer et al., "Long-term follow up of children with congenital complete atrioventricular block and the impact of pacemaker therapy," *Europace*, Oct. 2002; 4(4):345-349.

Barold et al., "Conventional and biventricular pacing in patients with first-degree atrioventricular block," *Europace*, Oct. 2012; 14(10):1414-9.

Barold et al., "The effect of hyperkalaemia on cardiac rhythm devices," *Europace*, Apr. 2014; 16(4):467-76.

Bayrak et al., "Added value of transoesophageal echocardiography during transseptal puncture performed by inexperienced operators," *Europace*, May 2012; 14(5):661-5.

Bergau et al., "Measurement of Left Atrial Pressure is a Good Predictor of Freedom From Atrial Fibrillation," *Indian Pacing and Electrophysiology Journal*, Jul. 2014; 14(4):181-93.

Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.

Bito et al., "Early exercise training after myocardial infarction prevents contractile but not electrical remodeling or hypertrophy," *Cardiovascular Research*, Apr. 2010; 86(1):72-81.

Bollmann et al., "Analysis of surface electrocardiograms in atrial fibrillation: techniques, research, and clinical applications," *Europace*, Nov. 2006; 8(11):911-926.

Bortone et al., "Evidence for an incomplete mitral isthmus block after failed ablation of a left postero-inferior concealed accessory pathway," *Europace*, Jun. 2006; 8(6):434-7.

Boulos et al., "Electroanatomical mapping and radiofrequency ablation of an accessory pathway associated with a large aneurysm of the coronary sinus," *Europace*, Nov. 2004; 6(6):608-12.

Brembilla-Perrot et al., "Incidence and prognostic significance of spontaneous and inducible antidromic tachycardia," *Europace*, Jun. 2013; 15(6):871-876.

Buber et al., "Morphological features of the P-waves at surface electrocardiogram as surrogate to mechanical function of the left atrium following a successful modified maze procedure," *Europace*, Apr. 2014; 16(4):578-86.

Burashnikov et al., "Late-phase 3 EAD. A unique mechanism contributing to initiation of atrial fibrillation," *Pacing Clin Electrophysiol.*, Mar. 2006; 29(3):290-5.

Burashnikov et al., "Atrial-selective inhibition of sodium-channel current by Wenxin Keli is effective in suppressing atrial fibrillation," *Heart Rhythm*, Jan. 2012; 9(1):125-31.

Calvo et al., "Efficacy of circumferential pulmonary vein ablation of atrial fibrillation in endurance athletes," *Europace*, Jan. 2010; 12(1):30-6.

Can et al., ""Atrial torsades de pointes" Induced by Low-Energy Shock From Implantable-Cardioverter Defibrillator," *Indian Pacing and Electrophysiology Journal*, Sep. 2013; 13(5):194-199.

Carroz et al., "Pseudo-pacemaker syndrome in a young woman with first-degree atrio-ventricular block," *Europace*, Apr. 2010; 12(4):594-596.

Catanchin et al., "Wolff-Parkinson-White syndrome with an unroofed coronary sinus without persistent left superior vena cava treated with catheter cryoablation," *Indian Pacing and Electrophysiology Journal*, Aug. 2008; 8(3):227-233.

Cazeau et al., "Cardiac resynchronization therapy," *Europace*, Sep. 2004; 5 Suppl 1:S42-8.

Cerqueira et al., "Standardized myocardial segmentation and nomenclature for tomographic imaging of the heart. A statement for healthcare professionals from the Cardiac Imaging Committee of the Council on Clinical Cardiology of the American Heart Association," *Circulation*, Jan. 29, 2002; 105(4):539-42.

Chandra et al., "Evaluation of KCB-328, a new IKr blocking antiarrhythmic agent in pacing induced canine atrial fibrillation," *Europace*, Sep. 2004; 6(5):384-91.

(56) References Cited

OTHER PUBLICATIONS

Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.
Charron et al., "A familial form of conduction defect related to a mutation in the PRKAG2 gene," *Europace*, Aug. 2007; 9(8):597-600.
Chou et al., "Effects of SEA0400 on Arrhythmogenicity in a Langendorff-Perfused 1-Month Myocardial Infarction Rabbit Model," *Pacing Clin Electrophysiol.*, May 2013; 36(5):596-606.
Ciploetta et al., "Posterior Coronary Vein as the Substrate for an Epicardial Accessory Pathway," *Indian Pacing and Electrophysiology Journal*, Aug. 2013; 13(4):142-7.
Climent et al., "Effects of endocardial microwave energy ablation," *Indian Pacing and Electrophysiology Journal*, Jul. 2005; 5(3):233-43.
Comtois et al., "Of circles and spirals: bridging the gap between the leading circle and spiral wave concepts of cardiac reentry," *Europace*, Sep. 2005; 7 Suppl 2:10-20.
Crick et al., "Anatomy of the pig heart: comparisons with normal human cardiac structure," *J. Anat.*, 1998, 193:105-119.
Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.
De Mattia et al., "Paroxysmal atrial fibrillation triggered by a monomorphic ventricular couplet in a patient with acute coronary syndrome," *Indian Pacing and Electrophysiology Journal*, Jan. 2012; 12(1):19-23.
DeSimone et al., "New approach to cardiac resynchronization therapy: CRT without left ventricular lead," Apr. 25, 2014, 2 pages.
De Sisti et al., "Electrophysiological determinants of atrial fibrillation in sinus node dysfunction despite atrial pacing," *Europace*, Oct. 2000; 2(4):304-11.
De Voogt et al., "Electrical characteristics of low atrial septum pacing compared with right atrial appendage pacing," *Europace*, Jan. 2005; 7(1):60-6.
De Voogt et al., "A technique of lead insertion for low atrial septal pacing," *Pacing Clin Electrophysiol.*, Jul. 2005; 28(7):639-46.
Dizon et al. "Real-time stroke volume measurements for the optimization of cardiac resynchronization therapy parameters," *Europace*, Sep. 2010; 12(9):1270-1274.
Duckett et al., "Relationship between endocardial activation sequences defined by high-density mapping to early septal contraction (septal flash) in patients with left bundle branch block undergoing cardiac resynchronization therapy," *Europace*, Jan. 2012; 14(1):99-106.
Eksik et al., "Influence of atrioventricular nodal reentrant tachycardia ablation on right to left inter-atrial conduction," *Indian Pacing and Electrophysiology Journal*, Oct. 2005; 5(4):279-88.
Fiala et al., "Left Atrial Voltage during Atrial Fibrillation in Paroxysmal and Persistent Atrial Fibrillation Patients," *PACE*, May 2010; 33(5):541-548.
Fragakis et al., "Acute beta-adrenoceptor blockade improves efficacy of ibutilide in conversion of atrial fibrillation with a rapid ventricular rate," *Europace*, Jan. 2009; 11(1):70-4.
Frogoudaki et al., "Pacing for adult patients with left atrial isomerism: efficacy and technical considerations," *Europace*, Apr. 2003; 5(2):189-193.
Ganapathy et al., "Implantable Device to Monitor Cardiac Activity with Sternal Wires," *Pacing Clin. Electrophysiol.*, Dec. 2014; Epub Aug. 24, 2014; 37(12):1630-40.
Geddes, "Accuracy limitations of chronaxie values," *IEEE Trans Biomed Eng.*, Jan. 2004; 51(1):176-81.
Gertz et al., "The impact of mitral regurgitation on patients undergoing catheter ablation of atrial fibrillation," *Europace*, Aug. 2011; 13(8):1127-32.
Girmatsion et al., "Changes in microRNA-1 expression and IK1 up-regulation in human atrial fibrillation," *Heart Rhythm*, Dec. 2009; 6(12):1802-9.
Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.
Goette et al., "Electrophysiological effects of angiotensin II. Part I: signal transduction and basic electrophysiological mechanisms," *Europace*, Feb. 2008; 10(2):238-41.
Gómez et al., "Nitric oxide inhibits Kv4.3 and human cardiac transient outward potassium current (Ito1)," *Cardiovasc Res.*, Dec. 2008; 80(3):375-84.
Gros et al., "Connexin 30 is expressed in the mouse sino-atrial node and modulates heart rate," *Cardiovascular Research*, Jan. 2010; 85(1):45-55.
Guenther et al., "Substernal Lead Implantation: A Novel Option to Manage OFT Failure in S-ICD patients," *Clinical Research Cardiology*, Feb. 2015; Epub Oct. 2, 2014; 104(2):189-91.
Guillem et al., "Noninvasive mapping of human atrial fibrillation," *J Cardiovasc Electrophysiol.*, May 2009; 20(5):507-513.
Hachisuka et al., "Development and Performance Analysis of an Intra-Body Communication Device," The 12$^{th}$ International Conference on Solid State Sensors, Actuators and Microsystems, vol. 4A1.3, pp. 1722-1725, 2003.
Hakacova et al., "Septal atrial pacing for the prevention of atrial fibrillation," *Europace*, 2007; 9:1124-1128.
Hasan et al., "Safety, efficacy, and performance of implanted recycled cardiac rhythm management (CRM) devices in underprivileged patients," *Pacing Clin Electrophysiol.*, Jun. 2011; 34(6):653-8.
Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.
He et al., "Three-dimensional cardiac electrical imaging from intracavity recordings," *IEEE Trans Biomed Eng.*, Aug. 2007; 54(8):1454-60.
Heist et al., "Direct visualization of epicardial structures and ablation utilizing a visually guided laser balloon catheter: preliminary findings," *J Cardiovasc Electrophysiol.*, Jul. 2011; 22(7):808-12.
Henz et al., "Synchronous Ventricular Pacing without Crossing the Tricuspid Valve or Entering the Coronary Sinus—Preliminary Results," *J Cardiovasc Electrophysiol.*, Dec. 2009; 20(12):1391-1397.
Hiippala et al., "Automatic Atrial Threshold Measurement and Adjustment in Pediatric Patients," *Pacing Clin Electrophysiol.*, Mar. 2010; 33(3):309-13.
Ho, "Letter to the Editor" *J Cardiovasc Electrophysiol.*, Mar. 2010; 21(3): E76.
Höijer et al., "Improved cardiac function and quality of life following upgrade to dual chamber pacing after long-term ventricular stimulation," *European Heart Journal*, Mar. 2002; 23(6):490-497.
Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.el-1736.e.
Inter-Office Memo, Model 6426-85 Canine Feasibility AV Septal 8 mm Screw-In Right Single Pass DDD Lead Final Report (AR # 0120A0207).
Ishigaki et al., "Prevention of immediate recurrence of atrial fibrillation with low-dose landiolol after radiofrequency catheter ablation," *Journal of Arrhythmia*, Oct. 2015; 31(5):279-285.
Israel, "The role of pacing mode in the development of atrial fibrillation," *Europace*, Feb. 2006; 8(2):89-95.
Janion et al., "Dispersion of P wave duration and P wave vector in patients with atrial septal aneurysm," *Europace*, Jul. 2007; 9(7):471-4.
Kabra et al., "Recent Trends in Imaging for Atrial Fibrillation Ablation," *Indian Pacing and Electrophysiology Journal*, 2010; 10(5):215-227.

(56) References Cited

OTHER PUBLICATIONS

Kalbfleisch et al., "Catheter Ablation with Radiofrequency Energy: Biophysical Aspects and Clinical Applications," *Journal of Cardiovascular Electrophysiology*, Oct. 2008; 3(2):173-186.
Katritsis et al., "Classification and differential diagnosis of atrioventricular nodal re-entrant tachycardia," *Europace*, Jan. 2006; 8(1):29-36.
Katritsis et al., "Anatomically left-sided septal slow pathway ablation in dextrocardia and situs inversus totalis," *Europace*, Aug. 2008; 10(8):1004-5.
Khairy et al., "Cardiac Arrhythmias In Congenital Heart Diseases," *Indian Pacing and Electrophysiology Journal*, Nov.-Dec. 2009; 9(6):299-317.
Kimmel et al., "Single-site ventricular and biventricular pacing: investigation of latest depolarization strategy," *Europace*, Dec. 2007; 9(12):1163-1170.
Knackstedt et al., "Electro-anatomic mapping systems in arrhythmias," *Europace*, Nov. 2008; 10 Suppl 3:iii28-iii34.
Kobayashi et al., "Successful Ablation of Antero-septal Accessory Pathway in the Non-Coronary Cusp in a Child," *Indian Pacing and Electrophysiology Journal*, 2012; 12(3):124-130.
Kojodjojo et al., "4:2:1 conduction of an AF initiating trigger," *Indian Pacing and Electrophysiology Journal*, Nov. 2015; 15(5):255-8.
Kołodzińska et al., "Differences in encapsulating lead tissue in patients who underwent transvenous lead removal," *Europace*, Jul. 2012; 14(7):994-1001.
Konecny et al., "Synchronous intra-myocardial ventricular pacing without crossing the tricuspid valve or entering the coronary sinus," *Cardiovascular Revascularization Medicine*, 2013; 14:137-138.
Kriatselis et al., "Ectopic atrial tachycardias with early activation at His site: radiofrequency ablation through a retrograde approach," *Europace*, Jun. 2008; 10(6):698-704.
Lalu et al., "Ischaemia-reperfusion injury activates matrix metalloproteinases in the human heart," *Eur Heart J.*, Jan. 2005; 26(1):27-35.
Laske et al., "Excitation of the Intrinsic Conduction System Through His and Interventricular Septal Pacing," *Pacing Clin. Electrophysiol.*, Apr. 2006; 29(4):397-405.
Leclercq, "Problems and troubleshooting in regular follow-up of patients with cardiac resynchronization therapy," *Europace*, Nov. 2009; 11 Suppl 5:v66-71.
Lee et al., "An unusual atrial tachycardia in a patient with Friedreich ataxia," *Europace*, Nov. 2011; 13(11):1660-1.
Lee et al., "Blunted Proarrhythmic Effect of Nicorandil in a Langendorff-Perfused Phase-2 Myocardial Infarction Rabbit Model," *Pacing Clin Electrophysiol.*, Feb. 2013; 36(2):142-51.
Lemay et al., "Spatial dynamics of atrial activity assessed by the vectorcardiogram: from sinus rhythm to atrial fibrillation," *Europace*, Nov. 2007; 9 Suppl 6:vi109-18.
Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.
Lewalter et al., "Comparison of spontaneous atrial fibrillation electrogram potentials to the P wave electrogram amplitude in dual chamber pacing with unipolar atrial sensing," *Europace*, Apr. 2000; 2(2):136-40.
Liakopoulos et al., "Sequential deformation and physiological considerations in unipolar right and left ventricular pacing," *European Journal of Cardio-thoracic Surgery*, Apr. 1, 2006; 29S1:S188-197.
Lian et al., "Computer modeling of ventricular rhythm during atrial fibrillation and ventricular pacing," *IEEE Transactions on Biomedical Engineering*, Aug. 2006; 53(8):1512-1520.
Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.
Lim et al., "Coupled pacing improves left ventricular function during simulated atrial fibrillation without mechanical dyssynchrony," *Europace*, Mar. 2010; 12(3):430-6.
Lou et al., "Tachy-brady arrhythmias: The critical role of adenosine-induced sinoatrial conduction block in post-tachycardia pauses," *Heart Rhythm.*, Jan. 2013; 10(1):110-8.
Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.
Macedo et al., "Septal accessory pathway: anatomy, causes for difficulty, and an approach to ablation," *Indian Pacing and Electrophysiology Journal*, Jul. 2010; 10(7):292-309.
Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3):e003344.
Mani et al., "Dual Atrioventricular Nodal Pathways Physiology: A Review of Relevant Anatomy, Electrophysiology, and Electrocardiogramanifestations," *Indian Pacing and Electrophysiology Journal*, Jan. 2014; 14(1):12-25.
Manios et al., "Effects of successful cardioversion of persistent atrial fibrillation on right ventricular refractoriness and repolarization," *Europace*, Jan. 2005; 7(1):34-9.
Manolis et al., "Prevention of atrial fibrillation by inter-atrial septum pacing guided by electrophysiological testing, in patients with delayed interatrial conduction," *Europace*, Apr. 2002; 4(2):165-174.
Marino et al., "Inappropriate mode switching clarified by using a chest radiograph," *Journal of Arrhythmia*, Aug. 2015; 31(4):246-248.
Markowitz et al., "Time course and predictors of autonomic dysfunction after ablation of the slow atrioventricular nodal pathway," *Pacing Clin Electrophysiol.*, Dec. 2004; 27(12):1638-43.
Marshall et al., "The effects of temperature on cardiac pacing thresholds," *Pacing Clin Electrophysiol.*, Jul. 2010, 33(7):826-833.
McSharry et al., "A Dynamical Model for Generating Synthetic Electrocardiogram Signals," *IEEE Transactions on Biomedical Engineering*, Mar. 2003; 50(3):289-294.
Meijler et al., "Scaling of Atrioventricular Transmission in *Mammalian* Species: An Evolutionary Riddle!," *Journal of Cfardiovascular Electrophysiology*, Aug. 2002; 13(8):826-830.
Meiltz et al., "Permanent form of junctional reciprocating tachycardia in adults: peculiar features and results of radiofrequency catheter ablation," *Europace*, Jan. 2006; 8(1):21-8.
Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.
Mestan et al., "The influence of fluid and diuretic administration on the index of atrial contribution in sequentially paced patients," *Europace*, Apr. 2006; 8(4):273-8.
Metin et al., "Assessment of the P Wave Dispersion and Duration in Elite Women Basketball Players," *Indian Pacing and Electrophysiology Journal*, 2010; 10(1):11-20.
Mills et al., "Left Ventricular Septal and Left Ventricular Apical Pacing Chronically Maintain Cardiac Contractile Coordination, Pump Function and Efficiency," *Circ Arrhythm Electrophysoil.*, Oct. 2009; 2(5):571-579.
Mitchell et al., "How do atrial pacing algorithms prevent atrial arrhythmias?" *Europace*, Jul. 2004; 6(4):351-62.
Mirzoyev et al., "Embryology of the Conduction System for the Electrophysiologist," *Indian Pacing and Electrophysiology Journal*, 2010; 10(8):329-338.
Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.
Montgomery et al., "Measurement of diffuse ventricular fibrosis with myocardial T1 in patients with atrial fibrillation," *J Arrhythm.*, Feb. 2016; 32(1):51-6.

(56) References Cited

OTHER PUBLICATIONS

Mulpuru et al., "Synchronous ventricular pacing with direct capture of the atrioventricular conduction system: Functional anatomy, terminology, and challenges," *Heart Rhythm*, Nov. 2016, Epub Aug. 3, 2016; 13(11):2237-2246.
Musa et al., "Inhibition of Platelet-Derived Growth Factor—AB Signaling Prevents Electromechanical Remodeling of Adult Atrial Myocytes that Contact Myofibroblasts," *Heart Rhythm*, Jul. 2013; 10(7):1044-1051.
Nagy et al., "Wnt-11 signalling controls ventricular myocardium development by patterning N-cadherin and β-catenin expression," *Cardiovascular Research*, Jan. 2010; 85(1):100-9.
Namboodiri et al., "Electrophysiological features of atrial flutter in cardiac sarcoidosis: a report of two cases," *Indian Pacing and Electrophysiology Journal*, Nov. 2012; 12(6):284-9.
Nanthakumar et al., "Assessment of accessory pathway and atrial refractoriness by transesophageal and intracardiac atrial stimulation: An analysis of methodological agreement," *Europace*, Jan. 1999; 1(1):55-62.
Neto et al., "Temporary atrial pacing in the prevention of postoperative atrial fibrillation," *Pacing Clin Electrophysiol.*, Jan. 2007; 30(Suppl 1):S79-83.
Nishijima et al., "Tetrahydrobiopterin depletion and NOS2 uncoupling contribute to heart failure-induced alterations in atrial electrophysiology," *Cardiovasc Res.*, Jul. 2011; 91(1):71-9.
Niwano et al., "Effect of oral L-type calcium channel blocker on repetitive paroxysmal atrial fibrillation: spectral analysis of fibrillation waves in the Holter monitoring," *Europace*, Dec. 2007; 9(12):1209-1215.
Okumura et al., "Effects of a high-fat diet on the electrical properties of porcine atria," *Journal of Arrhythmia*, Dec. 2015; 31(6):352-358.
Olesen et al., "Mutations in sodium channel β-subunit SCN3B are associated with early-onset lone atrial fibrillation," *Cardiovascular Research*, Mar. 2011; 89(4):786-93.
Ozmen et al., "P wave dispersion is increased in pulmonary stenosis," *Indian Pacing and Electrophysiology Journal*, Jan. 2006; 6(1):25-30.
Packer et al., "New generation of electro-anatomic mapping: Full intracardiac image integration," *Europace*, Nov. 2008; 10 Suppl 3:iii35-41.
Page et al., "Ischemic ventricular tachycardia presenting as a narrow complex tachycardia," *Indian Pacing and Electrophysiology Journal*, Jul. 2014; 14(4):203-210.
Pakarinen et al., "Pre-implant determinants of adequate long-term function of single lead VDD pacemakers," *Europace*, Apr. 2002; 4:137-141.
Patel et al., "Atrial Fibrillation after Cardiac Surgery: Where are we now?" *Indian Pacing and Electrophysiology Journal*, Oct.-Dec. 2008; 8(4):281-291.
Patel et al., "Successful ablation of a left-sided accessory pathway in a patient with coronary sinus atresia and arteriovenous fistula: clinical and developmental insights," *Indian Pacing and Electrophysiology Journal*, Mar. 2011; 11(2):43-49.
Peschar et al., "Left Ventricular Septal and Apex Pacing for Optimal Pump Function in Canine Hearts," *J Am Coll Cardiol.*, Apr. 2, 2003; 41(7):1218-1226.
Physiological Research Laboratories, Final Report for an Acute Study for Model 6426-85 AV Septal Leads, Feb. 1996.
Porciani et al., "Interatrial septum pacing avoids the adverse effect of interatrial delay in biventricular pacing: an echo-Doppler evaluation," *Europace*, Jul. 2002; 4(3):317-324.
Potse et al., "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.
Prystowsky et al., "Case studies with the experts: management decisions in atrial fibrillation," *J Cardiovasc Electrophysiol.*, Feb. 2008; 19(Suppl. 1):S1-12.
Prystowsky, "The history of atrial fibrillation: the last 100 years," *J Cardiovasc Electrophysiol*, Jun. 2008; 19(6):575-582.
Pytkowski et al., "Paroxysmal atrial fibrillation is associated with increased intra-atrial conduction delay," *Europace*, Dec. 2008; 10(12):1415-20.
Qu et al., "Dynamics and cardiac arrhythmias," *J Cardiovasc Electrophysiol.*, Sep. 2006; 17(9):1042-9.
Ravens et al., "Role of potassium currents in cardiac arrhythmias," *Europace*, Oct. 2008; 10(10):1133-7.
Ricci et al., Efficacy of a dual chamber defibrillator with atrial antitachycardia functions in treating spontaneous atrial tachyarrhythmias in patients with life-threatening ventricular tachyarrhythmias, *European Heart Journal*, Sep. 2002; 23(18):1471-9.
Roberts-Thomson et al., "Focal atrial tachycardia II: management," *Pacing Clin Electrophysiol.*, Jul. 2006; 29(7):769-78.
Rossi et al., "Endocardial vagal atrioventricular node stimulation in humans: reproducibility on 18-month follow-up," *Europace*, Dec. 2010; 12(12):1719-24.
Rouzet et al., "Contraction delay of the RV outflow tract in patients with Brugada syndrome is dependent on the spontaneous ST-segment elevation pattern," *Heart Rhythm*, Dec. 2011; 8(12):1905-12.
Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.
Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2):219-22.
Sairaku et al., "Prediction of sinus node dysfunction in patients with persistent atrial flutter using the flutter cycle length," *Europace*, Mar. 2012; 14(3):380-7.
Santini et al., "Immediate and long-term atrial sensing stability in single-lead VDD pacing depends on right atrial dimensions," *Europace*, Oct. 2001; 3(4):324-31.
Saremi et al., "Cardiac Conduction System: Delineation of Anatomic Landmarks With Multidetector CT," *Indian Pacing and Electrophysiology Journal*, Nov. 2009; 9(6):318-33.
Savelieva et al., "Anti-arrhythmic drug therapy for atrial fibrillation: current anti-arrhythmic drugs, investigational agents, and innovative approaches," *Europace*, Jun. 2008; 10(6):647-665.
Schmidt et al., "Navigated Dense strain imaging for post-radiofrequency ablation lesion assessment in the swine left atria," *Europace*, Jan. 2014; 16(1):133-41.
Schoonderwoerd et al., "Rapid Pacing Results in Changes in Atrial but not in Ventricular Refractoriness," *Pacing Clin Electrophysiol.*, Mar. 2002; 25(3):287-90.
Schoonderwoerd et al., "Atrial natriuretic peptides during experimental atrial tachycardia: role of developing tachycardiomyopathy," *J Cardiovasc Electrophysiol.*, Aug. 2004; 15(8):927-32.
Schoonderwoerd et al., "Atrial ultrastructural changes during experimental atrial tachycardia depend on high ventricular rate," *J Cardiovasc Electrophysiol.*, Oct. 2004; 15(10):1167-74.
Sedmera, "Function and form in the developing cardiovascular system," *Cardiovasc Res.*, Jul. 2011; 91(2):252-9.
Severi et al., "Alterations of atrial electrophysiology induced by electrolyte variations: combined computational and P-wave analysis," *Europace*, Jun. 2010; 12(6):842-9.
Seyedi et al., "A Survey on Intrabody Communications for Body Area Network Application," IEEE Transactions on Biomedical Engineering, vol. 60(8): 2067-2079, 2013.
Shah et al., "Stable atrial sensing on long-term follow up of VDD pacemakers," *Indian Pacing and Electrophysiology Journal*, Oct. 2006; 6(4):189-93.
Shenthar et al., "Permanent pacemaker implantation in a patient with situs solitus, dextrocardia, and corrected transposition of the great arteries using a novel angiographic technique," *Journal of Arrhythmia*, Apr. 2014; 30(2):134-138.
Shenthar et al., "Transvenous permanent pacemaker implantation in dextrocardia: technique, challenges, outcome, and a brief review of literature," *Europace*, Sep. 2014; 16(9):1327-33.
Shirayama, "Role of atrial fibrillation threshold evaluation on guiding treatment," *Indian Pacing and Electrophysiology Journal*, Oct. 2003; 3(4):224-230.

(56) References Cited

OTHER PUBLICATIONS

Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.
Spickler et al., "Totally Self-Contained Intracardiac Pacemaker," Journal of Electrocardiology, vol. 3(3&4): 324-331, 1970.
Sreeram et al., "Indications for Electrophysiology Study in children," *Indian Pacing and Electrophysiology Journal*, Apr.-Jun. 2008; 8(Suppl. 1):S36-S54.
Stockburger et al., "Optimization of cardiac resynchronization guided by Doppler echocardiography: haemodynamic improvement and intraindividual variability with different pacing configurations and atrioventricular delays," *Europace*, Oct. 2006; 8(10):881-6.
Stroobandt et al., "Prediction of Wenckebach Behavior and Block Response in DDD Pacemakers," *Pacing Clin Electrophysiol.*, Jun. 2006, 9(6):1040-6.
Suenari et al., "Idiopathic left ventricular tachycardia with dual electrocardiogram morphologies in a single patient," *Europace*, Apr. 2010; 12(4):592-4.
Sweeney et al., "Analysis of Ventricular Activation Using Surface Electrocardiogramadict Left Ventricular Reverse Volumetric Remodeling During Cardiac Resynchronization Therapy," Circulation, Feb. 9, 2010, 121(5): 626-34.
Tan et al., "Electrocardiogramce of ventricular repolarization remodelling during atrial fibrillation," *Europace*, Jan. 2008; 10(1):99-104.
Taramasco et al., "Internal low-energy cardioversion: a therapeutic option for restoring sinus rhythm in chronic atrial fibrillation after failure of external cardioversion," *Europace*, Jul. 1999; 1(3):179-82.
Testa et al., "Rate-control or rhythm-control: where do we stand?" *Indian Pacing and Electrophysiology Journal*, Oct. 2005; 5(4):296-304.
Thejus et al., "N-terminal Pro-Brain Natriuretic Peptide and Atrial Fibrillation," *Indian Pacing and Electrophysiology Journal*, Jan. 2009; 9(1):1-4.
Thornton et al., "Magnetic Assisted Navigation in Electrophysiology and Cardiac Resynchronisation: A Review," *Indian Pacing and Electrophysiology Journal*, Oct. 2006; 6(4):202-13.
Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.
Tomaske et al., "Do daily threshold trend fluctuations of epicardial leads correlate with pacing and sensing characteristics in paediatric patients?" *Europace*, Aug. 2007; 9(8):662-668.
Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.
Tournoux et al., "A 'Regularly Irregular' tachycardia: What is the diagnosis?" *Europace*, Dec. 2008; 10(12):1445-6.
Traykov et al., "Electrogram analysis at the His bundle region and the proximal coronary sinus as a tool to predict left atrial origin of focal atrial tachycardias," *Europace*, Jul. 2011; 13(7):1022-7.
Trudel et al., "Simulation of QRST integral maps with a membrane-based computer heart model employing parallel processing," *IEEE Trans Biomed Eng.*, Aug. 2004; 51(8):1319-29.
Tse et al., "Cardiac dynamics: Alternans and arrhythmogenesis," *Journal of Arrhythmia*, Oct. 2016; 32(5):411-417.
Tse, "Mechanisms of cardiac arrhythmias," *Journal of Arrhythmia*, Apr. 2016; 32(2):75-81.
Ueda et al., "Outcomes of single- or dual-chamber implantable cardioverter defibrillator systems in Japanese patients," *Journal of Arrhythmia*, Apr. 2016; 32(2):89-94.
Van Dam et al., "Volume conductor effects involved in the genesis of the P wave," *Europace*, Sep. 2005; 7 Suppl 2:30-8.
Van den Berg et al., "Depletion of atrial natriuretic peptide during longstanding atrial fibrillation," *Europace*, Sep. 2004; 6(5):433-7.
Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.
Van Opstal et al., "Paradoxical increase of stimulus to atrium interval despite His-bundle capture during para-Hisian pacing," *Europace*, Dec. 2009; 11(12):1702-4.
Veenhuyzen et al., "Diagnostic pacing maneuvers for supraventricular tachycardia: part 1," *Pacing Clin Electrophysiol.*, Jun. 2011; 34(6):767-82.
Veenhuyzen et al., "Diagnostic pacing maneuvers for supraventricular tachycardias: part 2," *Pacing Clin Electrophysiol.*, Jun. 2012; 35(6):757-69.
Veenhuyzen et al., "Principles of Entrainment: Diagnostic Utility for Supraventricular Tachycardia," *Indian Pacing and Electrophysiology Journal*, 2008; 8(1):51-65.
Verbrugge et al., "Revisiting diastolic filling time as mechanistic insight for response to cardiac resynchronization therapy," *Europace*, Dec. 2013; 15(12):1747-56.
Verrier et al., "Mechanisms of ranolazine's dual protection against atrial and ventricular fibrillation," *Europace*, Mar. 2013; 15(3):317-324.
Verrijcken et al., "Pacemaker-mediated tachycardia with varying cycle length: what is the mechanism?" *Europace*, Oct. 2009; 11(10):1400-2.
Villani et al., "Reproducibility of internal atrial defibrillation threshold in paroxysmal and persistent atrial fibrillation," *Europace*, Jul. 2004; 6(4):267-72.
Violi et al., "Antioxidants for prevention of atrial fibrillation: a potentially useful future therapeutic approach? A review of the literature and meta-analysis," *Europace*, Aug. 2014; 16(8):1107-1116.
Weber et al., "Adenosine sensitive focal atrial tachycardia originating from the non-coronary aortic cusp," *Europace*, Jun. 2009; 11(6):823-6.
Weber et al., "Open-irrigated laser catheter ablation: relationship between the level of energy, myocardial thickness, and collateral damages in a dog model," *Europace*, Jan. 2014; 16(1):142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," *IEEE Trans Biomed Eng.*, Apr. 1995; 42(4):343-57.
Weijs et al., "Clinical and echocardiographic correlates of intra-atrial conduction delay," *Europace*, Dec. 2011; 13(12):1681-7.
Weiss et al., "The influence of fibre orientation, extracted from different segments of the human left ventricle, on the activation and repolarization sequence: a simulation study," *Europace*, Nov. 2007; 9(Suppl. 6):vi96-vi104.
Wetzel et al., "A stepwise mapping approach for localization and ablation of ectopic right, left, and septal atrial foci using electroanatomic mapping," *European Heart Journal*, Sep. 2002; 23(17):1387-1393.
Wlodarska et al., "Thromboembolic complications in patients with arrhythmogenic right ventricular dysplasia/cardiomyopathy," *Europace*, Aug. 2006; 8(8):596-600.
Wong et al., "A review of mitral isthmus ablation," *Indian Pacing and Electrophysiology Journal*, 2012; 12(4):152-170.
Wu et al., "Acute and long-term outcome after catheter ablation of supraventricular tachycardia in patients after the Mustard or Senning operation for D-transposition of the great arteries," *Europace*, Jun. 2013; 15(6):886-91.
Xia et al., "Asymmetric dimethylarginine concentration and early recurrence of atrial fibrillation after electrical cardioversion," *Pacing Clin Electrophysiol.*, Aug. 2008; 31(8):1036-40.
Yamazaki et al., "Acute Regional Left Atrial Ischemia Causes Acceleration of Atrial Drivers during Atrial Fibrillation," *Heart Rhythm*, Jun. 2013; 10(6):901-9.
Yang et al., "Focal atrial tachycardia originating from the distal portion of the left atrial appendage: Characteristics and long-term outcomes of radiofrequency ablation," *Europace*, Feb. 2012; 14(2):254-60.

(56) References Cited

OTHER PUBLICATIONS

Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.
Yoon et al., "Measurement of thoracic current flow in pigs for the study of defibrillation and cardioversion," *IEEE Transactions on Biomedical Engineering*, Oct. 2003; 50(10):1167-1773.
Yuan et al., "Recording monophasic action potentials using a platinum-electrode ablation catheter," *Europace*, Oct. 2000, 2(4):312-9.
Yusuf et al., "5-Hydroxytryptamine and Atrial Fibrillation: How Significant is This Piece in the Puzzle?" *J Cardiovasc Electrophysiol.*, Feb. 2003; 14(2):209-14.
Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.
Zhang et al., "Acute atrial arrhythmogenicity and altered Ca(2+) homeostasis in murine RyR2-P2328S hearts," *Cardiovascular Research*, Mar. 2011; 89(4):794-804.
Zoghi et al., "Electrical stunning and hibernation: suggestion of new terms for short- and long-term cardiac memory," *Europace*, Sep. 2004; 6(5):418-24.
Zografos et al., "Inhibition of the renin-angiotensin system for prevention of atrial fibrillation," *Pacing Clin Electrophysiol.*, Oct. 2010; 33(10):1270-85.
(PCT/US2014/066792) PCT Notification of Transmittal of the International Search Report and the Written Opinion of the International Searching Authority.
(PCT/US2014/013601) PCT Notification of Transmittal of the International Search Report and the Written Opinion of the International Searching Authority.
(PCT/US2014/036782) PCT Notification of Transmittal of the International Search Report and the Written Opinion of the International Searching Authority, Mailed Aug. 22, 2014, 11 pages.
International Search Report and Written Opinion for Application No. PCT/US2017/047378, 8 pages, date mailed Dec. 6, 2017.
(PCT/US2018/050988) PCT Notification of Transmittal of the International Search Report and the Written Opinion of the International Searching Authority, Mailed Nov. 14, 2018, 11 pages.
(PCT/US2018/050993) PCT Notification of Transmittal of the International Search Report and the Written Opinion of the International Searching Authority, mailed Nov. 16, 2018, 7 pages.
(PCT/US2019/023642) PCT Notification of Transmittal of the International Search Report and the Written Opinion of the International Searching Authority, mailed Jun. 28, 2019, 14 pages.
(PCT/US2019/023645) PCT Notification of Transmittal of the International Search Report and the Written Opinion of the International Searching Authority, mailed Sep. 4, 2019, 14 pages.
(PCT/US2019/023646) PCT Notification of Transmittal of the International Search Report and the Written Opinion of the International Searching Authority, mailed Aug. 19, 2019, 15 pages.
(PCT/IB2019/057352) PCT Notification of Transmittal of the International Search Report and the Written Opinion of the International Searching Authority, mailed Nov. 27, 2019, 123 pages.
International Search Report and Written Opinion for Application No. PCT/US2020/023525, 10 pages, date mailed Jul. 9, 2020.
International Search Report and Written Opinion for Application No. PCT/US2020/047802, 9 pages, date mailed Nov. 19, 2020.
International Search Report and Written Opinion from PCT Application No. PCT/US2020/062466, dated Jan. 27, 2021, 15 pages.
International Search Report and Written Opinion from PCT Application No. PCT/US2021/025149, dated Jun. 30, 2021, 13 pages.

CARDIAC CONDUCTION SYSTEM ENGAGEMENT

The present application claims the benefit of U.S. Provisional Application No. 63/005,064, filed Apr. 3, 2020, which is incorporated herein by reference in its entirety.

The disclosure herein relates to systems and methods for use in determining cardiac conduction system engagement using one or more metrics of dispersion.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

IMDS may be described as delivering one or both of Conventional pacing therapy and cardiac conduction system pacing therapy. Conventional, or traditional, pacing therapy may be described as delivering pacing pulses into myocardial tissue that is not part of the cardiac conduction system of the patient's heart such that, e.g., electrical activation propagates from one myocardial cell to another myocardial cell (also referred to as "cell-to-cell"). For instance, the conventional pacing therapy may deliver pacing pulses directly into the muscular heart tissue that is to be depolarized to provide the contraction of the heart. For example, conventional left ventricular pacing therapy may utilize a left ventricular (LV) coronary sinus lead that is implanted so as to extend through one or more veins, the vena cava, the right atrium, and into the coronary sinus to a region adjacent to the free wall of the left ventricle of the heart so as to deliver pacing pulses to the myocardial tissue of the free wall of the left ventricle.

Cardiac conduction system pacing therapy may be described as delivering pacing pulses into the cardiac conduction system. More specifically, the cardiac conduction system pacing therapy may include one or more parts of the cardiac conduction system such as the left bundle branch, bundle of His, atrioventricular node, right bundle branch, etc. For example, a ventricle-from-atrium (VfA) lead may deliver pacing pulses directly to the left bundle branch of the cardiac conduction system such that the pulses propagate along the left bundle branch and Purkinje fibers to initiate depolarization of cardiac tissues proximate thereto (e.g., the myocardial tissue of the left ventricle).

Systems for implanting medical devices may include workstations or other equipment in addition to the implantable medical device itself. In some cases, these other pieces of equipment assist the physician or other technician with placing the intracardiac leads at particular locations on the heart. In some cases, the equipment provides information to the physician about the electrical activity of the heart and the location of the intracardiac lead. The equipment may perform similar functions as the medical device, including delivering electrical stimulation to the heart and sensing the depolarizations of the heart. In some cases, the equipment may include equipment for obtaining an electrocardiogram (ECG) via electrodes on the surface, or skin, of the patient. More specifically, the patient may have a plurality of electrodes on an ECG belt or vest that surrounds the torso of the patient. After the belt or vest has been secured to the torso, a physician can perform a series of tests to evaluate a patient's cardiac response. The evaluation process can include detection of a baseline rhythm in which no electrical stimuli is delivered to cardiac tissue and another rhythm after electrical stimuli is delivered to the cardiac tissue.

The ECG electrodes placed on the body surface of the patient may be used for various therapeutic purposes (e.g., cardiac resynchronization therapy) including optimizing lead location, pacing parameters, etc. based on one or more metrics derived from the signals captured by the ECG electrodes.

SUMMARY

The exemplary systems and methods described herein may be configured to assist users (e.g., physicians, clinicians, doctors, etc.) to determine whether a cardiac conduction system pacing therapy has engaged the cardiac conduction system of a patient (e.g., the left branch right, the right bundle branch, etc.). Thus, the illustrative systems and methods may be performed during delivery of cardiac conduction system pacing therapy such as, e.g., ventricle-from-atrium (VfA) pacing therapy, His bundle pacing therapy, left bundle branch area pacing, intraseptal left ventricular endocardial pacing, right bundle branch area pacing, etc. Further, although the cardiac conduction system pacing therapy may be described as being invasive (e.g., due to electrodes implanted into the patient's heart to perform the cardiac conduction system pacing therapy, etc.), the illustrative systems and methods may be described as being noninvasive. For example, the illustrative systems and methods may not use implantable devices such as leads, probes, sensors, catheters, etc. to evaluate whether the cardiac conduction system of the patient is engaged by the cardiac conduction system therapy pacing therapy. Instead, the illustrative systems and methods may use electrical measurements taken noninvasively using, e.g., a plurality of external electrodes attached to the skin of a patient about the patient's torso.

Entry into the cardiac conduction system may be achieved by pacing from ventricle-from-atrium (VfA) or other locations proximate the cardiac conduction system. Such entry may be direct or immediate or may be delayed in which case standard metrics like QRS narrowing may not be apparent, especially, in patients with existing ventricular conduction disorders like a left bundle branch block. Distinguishing between activation through involvement of conduction system and activation lacking involvement of conduction system may be helpful in providing successful VfA and other cardiac conduction system pacing efforts.

The illustrative systems and methods described herein may provide and utilize various processes and metrics based on dispersion of surrogate cardiac electrical activation times determined using a plurality of external electrodes (e.g., surface mapping activation times). Such processes and metrics be useful in determining if activation occurred through involvement or entry of left bundle branch and/or right bundle branch.

In one or more embodiments, the illustrative systems and methods may determine surrogate cardiac electrical activation times using electrodes located in a specific anatomic area of the body such as, e.g., left-sided external electrodes positioned on the body surface to the left of the sternum and to the left of the spine and/or right-sided external electrodes positioned on the body surface to the right of the sternum and to the right of the spine. Further, a standard deviation of surrogate cardiac electrical activation times from such electrodes during VfA pacing therapy and/or other conduction system pacing therapy may be determined or calculated. Then, it may be determined that the electrical activation during cardiac conduction system pacing occurs through entry into the left bundle branch if the standard deviation of activation times of the left-sided external electrodes is less than a certain threshold (e.g., 20 milliseconds (ms)). Further, it may be determined that electrical activation during pacing occurs through entry into the right bundle branch if the standard deviation of activation times from the right-sided electrodes is less than a certain threshold (e.g., 20 ms).

Additionally, the illustrative systems and methods may further adjust one or more pacing parameters including location of the pacing lead, angle of insertion through the atrioventricular (AV) groove, pacing vector, pacing timing (e.g., AV timing), etc. to achieve entry into, or engagement with, the left bundle or the right bundle if, for example, the standard deviation of activation times from the left side are not less than the threshold when targeting paced conduction through the left bundle branch or the standard deviation of activation times from the right side are not less than the threshold when targeting paced conduction through the right bundle branch.

One illustrative system may include an electrode apparatus and a computing apparatus operably coupled to the electrode apparatus. The electrode apparatus may include a plurality of external electrodes to be disposed proximate a patient's skin. The plurality of external electrodes may include a plurality of left external electrodes positioned to the left side of the patient's torso. Further, the plurality of external electrodes may include a plurality of right external electrodes positioned to the right side of the patient's torso. The computing apparatus may include processing circuitry and may be configured to measure surrogate cardiac electrical activation times using the plurality external electrodes of the electrode apparatus during delivery of cardiac conduction system pacing therapy. The surrogate cardiac electrical activation times may be representative of depolarization of cardiac tissue that propagates through the torso of the patient. The computing apparatus may be further configured to generate electrical heterogeneity information (EHI) based on the measured surrogate cardiac electrical activation times during delivery of the cardiac conduction system pacing therapy. The EHI may include one or both of a left-sided metric of dispersion based on the surrogate cardiac electrical activation times measured using the plurality of left external electrodes and a right-sided metric of dispersion based on the surrogate cardiac electrical activation times measured using the plurality of right external electrodes. The computing apparatus may be further configured to determine whether a left bundle branch of the cardiac conduction system is engaged by the cardiac conduction system pacing therapy based on the left-sided metric of dispersion and determine whether a right bundle branch of the cardiac conduction system is engaged by the cardiac conduction system pacing therapy based on the right-sided metric of dispersion.

One illustrative method may include measuring surrogate cardiac electrical activation times using a plurality external electrodes disposed proximate a patient's skin during delivery of cardiac conduction system pacing therapy. The plurality of external electrodes may include a plurality of left external electrodes positioned to the left side of the patient's torso. Further, the plurality of external electrodes may include a plurality of right external electrodes positioned to the right side of the patient's torso. The surrogate cardiac electrical activation times may be representative of depolarization of cardiac tissue that propagates through the torso of the patient. The illustrative method may further include generating electrical heterogeneity information (EHI) based on the measured surrogate cardiac electrical activation times during delivery of the cardiac conduction system pacing therapy. The EHI may include one or both of a left-sided metric of dispersion based on the surrogate cardiac electrical activation times measured using the plurality of left external electrodes and a right-sided metric of dispersion based on the surrogate cardiac electrical activation times measured using the plurality of right external electrodes. The illustrative method may further include determining whether a left bundle branch of the cardiac conduction system is engaged by the cardiac conduction system pacing therapy based on the left-sided metric of dispersion and determining whether a right bundle branch of the cardiac conduction system is engaged by the cardiac conduction system pacing therapy based on the right-sided metric of dispersion.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
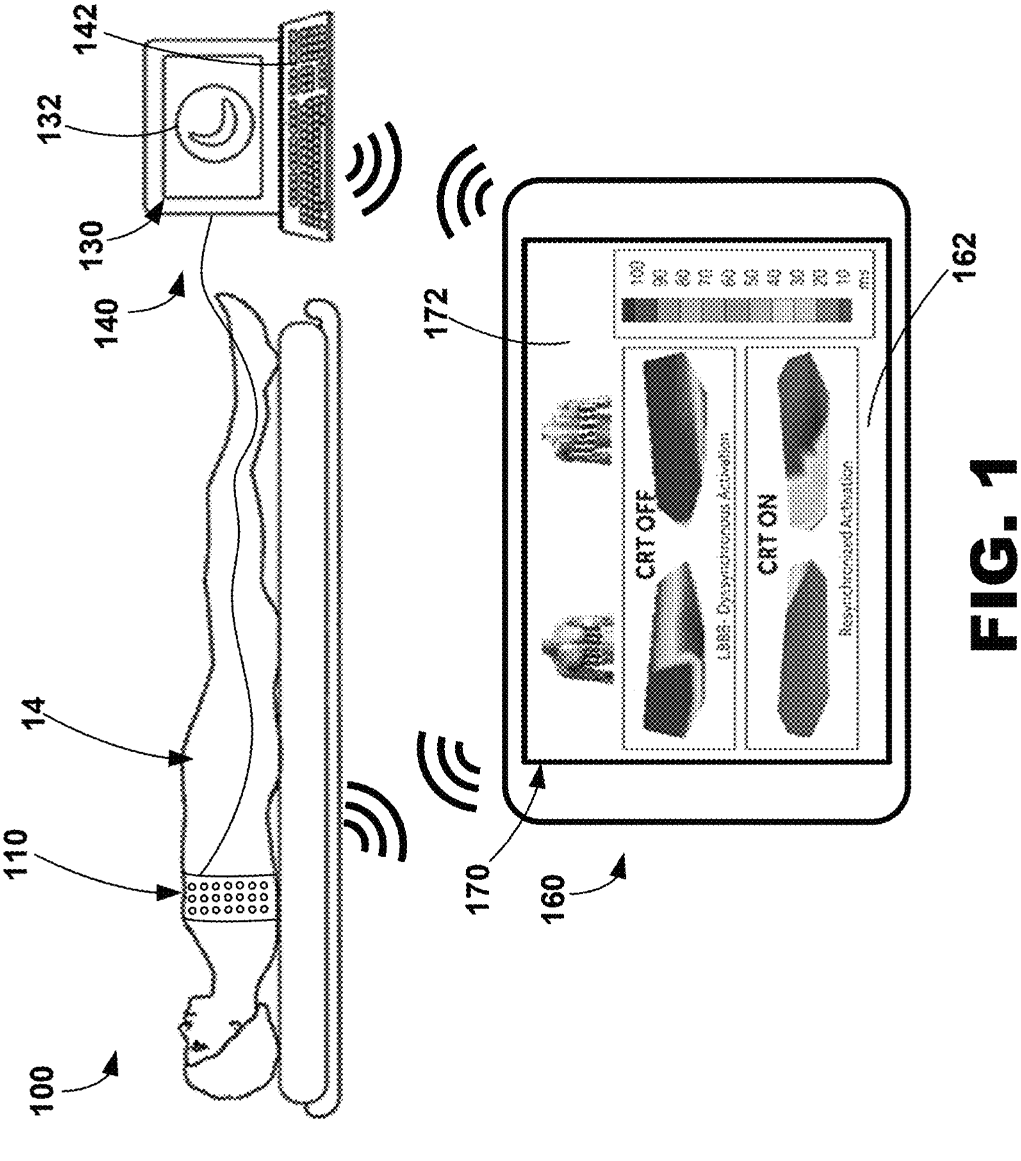
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Illustrative systems and methods shall be described with reference to FIGS. 1-10. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

A plurality of electrocardiogram (ECG) signals (e.g., torso-surface potentials) may be measured, or monitored, using a plurality of external electrodes positioned about the surface, or skin, of a patient. The ECG signals may be used to determine whether a patient's cardiac conduction system has been engaged by cardiac conduction pacing therapy or another cardiac therapy and to evaluate a patient's cardiac health. As described herein, the ECG signals may be gathered or obtained noninvasively since, e.g., implantable electrodes may not be used to measure the ECG signals. Further, the ECG signals may be used to determine cardiac electrical activation times, which may be used to generate various metrics (e.g., electrical heterogeneity information) that may be used by a user (e.g., physician) to determine whether a patient's cardiac conduction system has been engaged by cardiac conduction system pacing therapy such as, e.g., His bundle pacing therapy, ventricle-from-atrium (VfA) pacing therapy, left bundle branch area pacing therapy, right bundle branch area pacing therapy, and intraseptal left ventricular endocardial pacing therapy.

Various illustrative systems, methods, and graphical user interfaces may be configured to use electrode apparatus including external electrodes, display apparatus, and computing apparatus to noninvasively assist a user (e.g., a physician) in the determination of whether a patient's cardiac conduction system has been engaged by cardiac conduction system pacing therapy and in the evaluation of cardiac health. An illustrative system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014, and issued on Mar. 26, 2016, and U.S. Provisional Patent Application Ser. No. 62/957,449 filed on Jan. 6, 2020, entitled "Bioelectric Sensor Device and Methods," each of which is incorporated herein by reference in its entirety. Further, illustrative electrode apparatus 110 will be described in more detail in reference to FIGS. 2-3.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to locate, or place, one or more pacing electrodes proximate the patient's heart in conjunction with the configuration of cardiac therapy.

For example, the illustrative systems and methods may provide image guided navigation that may be used to navigate leads including electrodes, leadless electrodes, wireless electrodes, catheters, etc., within the patient's body while also providing noninvasive cardiac therapy configuration including determining an effective, or optimal, pre-excitation intervals such as A-V and V-V intervals, etc. Illustrative systems and methods that use imaging apparatus and/or electrode apparatus may be described in U.S. Pat. No. 9,877,789 B2 to Ghosh issued on Jan. 30, 2018, U.S. Pat. No. 10,251,555 B2 to Ghosh et al. issued on Apr. 9, 2019, U.S. Pat. No. 9,924,884 B2 to Ghosh et al. issued on Mar. 27, 2018, U.S. Pat. No. 10,064,567 B2 to Ghosh et al. issued on Sep. 4, 2018, each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. An exemplary system that employs ultrasound can be found in U.S. Pat. App. Pub. No. 2017/0303840 entitled NONINVASIVE ASSESSMENT OF CARDIAC RESYNCHRONIZATION THERAPY to Stadler et al., incorporated by reference in its entirety. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate implantable apparatus to target locations within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 to Zarkh et al. issued on May 20, 2014, U.S. Pat. No. 8,861,830 to Brada et al. issued on Oct. 14, 2014, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The computing apparatus 140 and the remote computing device 160 may each include display apparatus 130, 170, respectively, that may be configured to display and analyze data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including surrogate cardiac electrical activation times and electrical heterogeneity information that may be pertinent to determining whether a patient's cardiac conduction system such as, e.g., the left bundle branch and/or the right bundle branch, has been engaged by cardiac conduction system pacing therapy. Additionally, such surrogate cardiac electrical activation times and electrical heterogeneity information may also be pertinent to the therapeutic nature of one or more parameters related to cardiac therapy such as, e.g., pacing parameters, lead location, etc., and thus, may be useful for the adjustment thereof. More specifically, for example, the QRS complex of a single cardiac cycle may be evaluated for one or more metrics such as, e.g., QRS onset, QRS offset, QRS peak, electrical heterogeneity information (EHI), electrical activation times referenced to earliest activation time, left-sided standard deviation of electrical activation times, right-sided standard deviation of electrical activation times, standard deviation of activation times (SDAT), average left ventricular surrogate cardiac electrical activation times (LVAT), QRS duration (e.g., interval between QRS onset to QRS offset), difference between average left surrogate and average right surrogate activation times, relative or absolute QRS morphology, difference between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), global and/or locals metrics of dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, a tablet computer, a mobile device, and a cellular telephone. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining QRS onsets, QRS offsets, medians, modes, averages, peaks or maximum values, valleys or minimum values, metrics of dispersion such as standard deviations, etc., for determining electrical activation times, for driving a graphical user interface configured to noninvasively assist a user in determining whether a patient's cardiac conduction system is engaged by cardiac conduction system pacing therapy, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., left bundle branch, right bundle branch, biventricular pacing, right ventricle only pacing, left ventricle only pacing, etc.), and arrhythmia detection and treatment, rate adaptive settings and performance, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of configuration information related to the cardiac therapy delivered by cardiac therapy apparatus such as, e.g., an implantable medical device.

Although, as depicted, the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, indications of whether a patient's cardiac conduction system is engaged by cardiac conduction system pacing therapy and/or another cardiac therapy, a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, metrics of dispersion, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein. Further, additional illustrative systems, methods, and devices that may be used with the present disclosure may be described in U.S. Provisional Patent Application Ser. No. 62/913,002 entitled "Systems, Methods, and Devices for Determining Cardiac Condition" and filed on Oct. 9, 2019.

Figure 2:
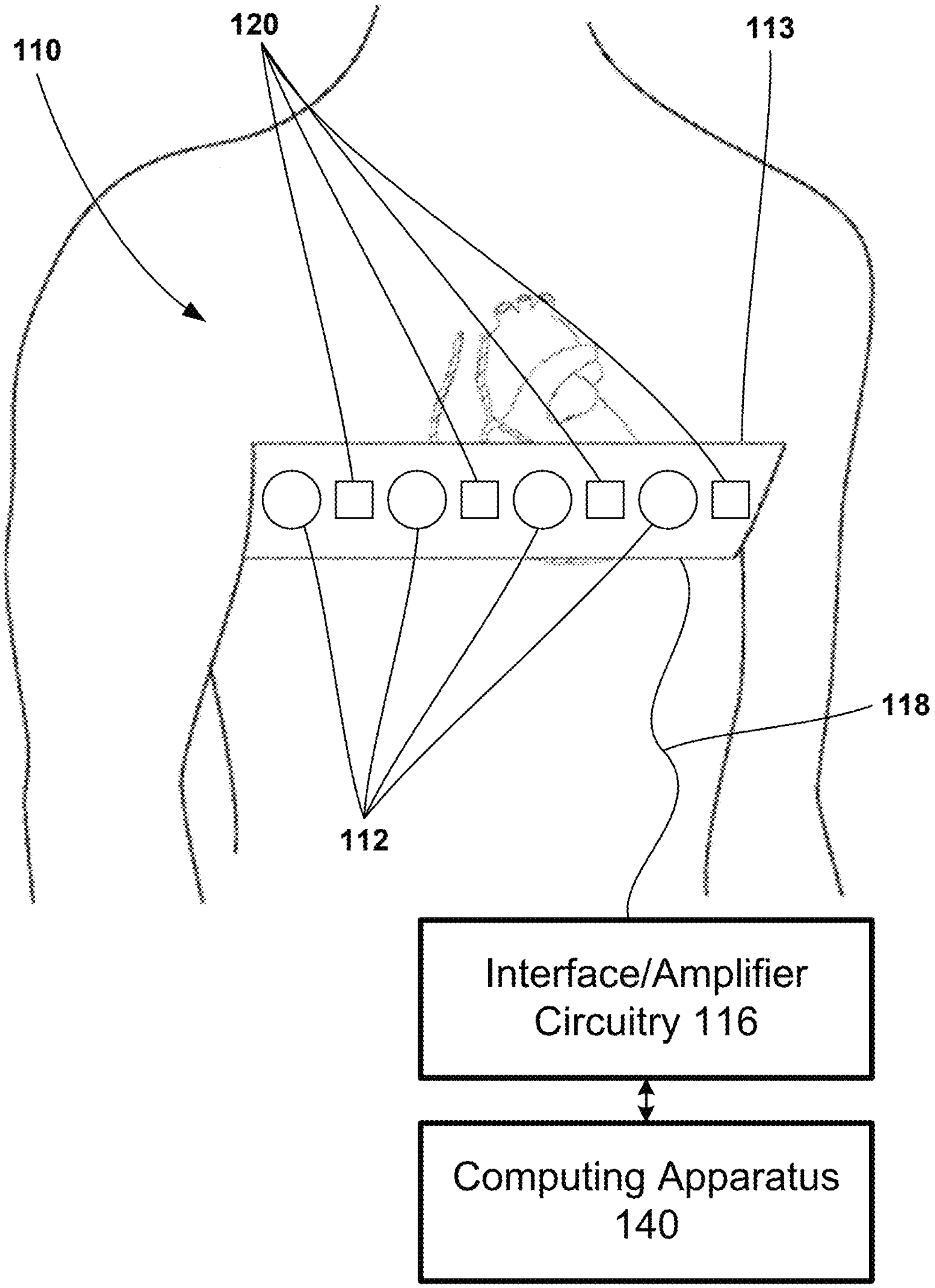
FIGS. 2-3 are diagrams of exemplary external electrode apparatus for monitoring electrical activity (e.g., torso-surface potentials, surrogate cardiac electrical activation times, etc.).

The illustrative electrode apparatus 110 may be configured to measure body-surface potentials of a patient 14 and, more particularly, torso-surface potentials of a patient 14. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

The illustrative electrode apparatus 110 may be further configured to measure, or monitor, sounds from at least one or both the patient 14. As shown in FIG. 2, the illustrative electrode apparatus 110 may include a set, or array, of acoustic sensors 120 attached, or coupled, to the strap 113. The strap 113 may be configured to be wrapped around the torso of a patient 14 such that the acoustic sensors 120 surround the patient's heart. As further illustrated, the acoustic sensors 120 may be positioned around the circumference of a patient 14, including the posterior, lateral, posterolateral, anterolateral, and anterior locations of the torso of a patient 14.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to the computing apparatus 140 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 14. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 14. Still further, in other examples, one or both of the electrodes 112 and the acoustic sensors 120 may be part of, or located within, two sections of material or two patches. One of the two patches may be located on the anterior side of the torso of the patient 14 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 14 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 14 across the left side of the patient 14 to the posterior side of the patient 14. Yet still further, in other examples, one or both of the electrodes 112 and the acoustic sensors 120 may be arranged in a curve around the armpit area and may have an electrode/sensor-density that less dense on the right thorax that the other remaining areas.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 14. Instead, the electrodes 112 and acoustic sensors 120 may be arranged in an array that extends only part of the way or partially around the patient 14. For example, the electrodes 112 and acoustic sensors 120 may be distributed on the anterior, posterior, and left sides of the patient with less or no electrodes and acoustic sensors proximate the right side (including posterior and anterior regions of the right side of the patient). Further, for example, the electrodes 112 and acoustic sensors 120 may be distributed on the anterior, posterior, and right sides of the patient with less or no electrodes and acoustic sensors proximate the left side (including posterior and anterior regions of the left side of the patient).

The computing apparatus 140 may record and analyze the torso-surface potential signals sensed by electrodes 112 and the sound signals sensed by the acoustic sensors 120, which are amplified/conditioned by the interface/amplifier circuitry 116. The computing apparatus 140 may be configured to analyze the electrical signals from the electrodes 112 to provide electrocardiogram (ECG) signals, information, or data from the patient's heart as will be further described herein. The computing apparatus 140 may be configured to analyze the signals from the electrodes 112 to provide surrogate cardiac electrical activation data such as surrogate cardiac electrical activation times, e.g., representative of actual, or local, electrical activation times of one or more regions of the patient's heart as will be further described herein. Measurement of activation times can be performed by picking an appropriate fiducial point (e.g., peak values, minimum values, minimum slopes, maximum slopes, zero crossings, threshold crossings, etc. of a near or far-field EGM) and measuring time between the onset of cardiac depolarization (e.g., onset of QRS complexes) and the appropriate fiducial point (e.g., within the electrical activity). The activation time between the onset of the QRS complex (or the peak Q wave) to the fiducial point may be referred to as q-LV time. In at least one embodiment, the earliest QRS onset from all of the plurality of electrodes may be utilized as the starting point for each activation time for each electrode, and the maximum slope following the onset of the QRS complex may be utilized as the end point of each activation time for each electrode. The computing apparatus 140 may be configured to analyze the electrical signals from the acoustic sensors 120 to provide sound signals, information, or data from the patient's body and/or devices implanted therein.

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient (e.g., to determine whether a patient's cardiac conduction system is engaged by cardiac conduction system pacing therapy).

Further, the electrode apparatus 110 may further include reference electrodes and/or drive electrodes to be, e.g. positioned about the lower torso of the patient 14, that may be further used by the system 100. For example, the electrode apparatus 110 may include three reference electrodes, and the signals from the three reference electrodes may be combined to provide a reference signal. Further, the electrode apparatus 110 may use of three caudal reference electrodes (e.g., instead of standard references used in a Wilson Central Terminal) to get a "true" unipolar signal with less noise from averaging three caudally located reference signals.

Figure 3:
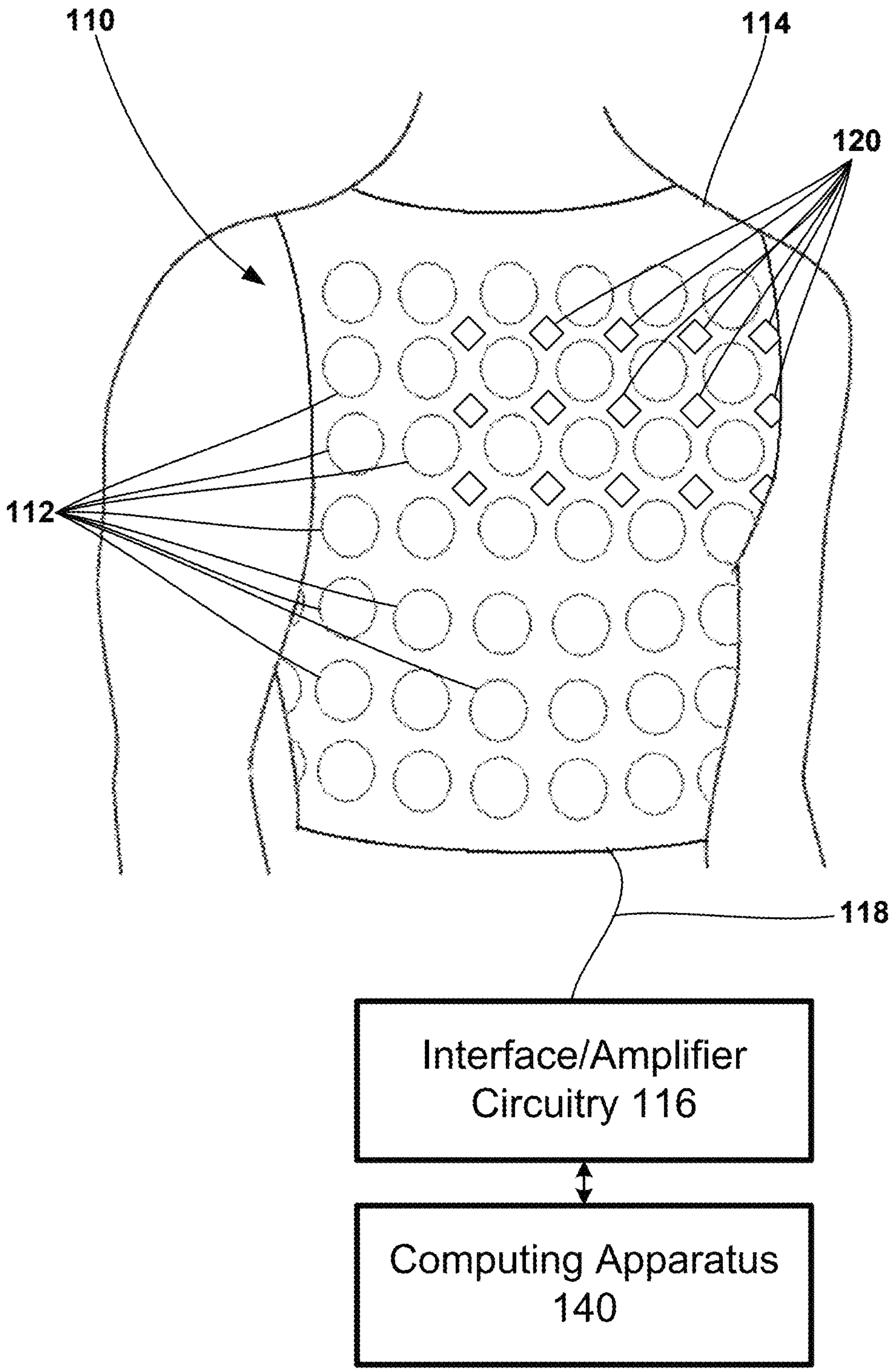

FIG. 3 illustrates another illustrative electrode apparatus 110 that includes a plurality of electrodes 112 configured to surround the heart of the patient 14 and record, or monitor, the electrical signals associated with the depolarization and repolarization of the heart after the signals have propagated through the torso of the patient 14 and a plurality of acoustic sensors 120 configured to surround the heart of the patient 14 and record, or monitor, the sound signals associated with the heart after the signals have propagated through the torso of the patient 14. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate cardiac electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 14, including, for example, the posterior, lateral, posterolateral, anterolateral, and anterior locations of the torso of a patient 14.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 14. Further, the vest 114 may be marked to assist in determining the location of the electrodes 112 and the acoustic sensors 120 on the surface of the torso of the patient 14. In some examples, there may be about 25 to about 256 electrodes 112 and about 25 to about 256 acoustic sensors 120 distributed around the torso of the patient 14, though other configurations may have more or fewer electrodes 112 and more or fewer acoustic sensors 120.

The illustrative systems and methods may be used to provide noninvasive assistance to a user in the evaluation and configuration of cardiac conduction system pacing therapy being presently delivered to the patient (e.g., by an implantable medical device delivering cardiac conduction system pacing therapy, etc.). Further, it is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

The illustrative systems and methods described herein may provide users (e.g., clinicians, doctors, etc.) a useful tool to determine whether a patient's cardiac conduction system is engaged by cardiac conduction system pacing therapy. In particular, the illustrative systems and methods described herein may provide users a useful tool to determine whether a left bundle branch or right bundle branch of a patient's cardiac conduction system is engaged by cardiac conduction system pacing therapy by generating one or more local metrics of dispersion of surrogate cardiac electrical activation times such as, e.g., a left-sided standard deviation of surrogate cardiac electrical activation times measured using a plurality of left external electrodes and/or a right-sided standard deviation of surrogate cardiac electrical activation times measured using a plurality of right external electrodes.

Figure 4A:
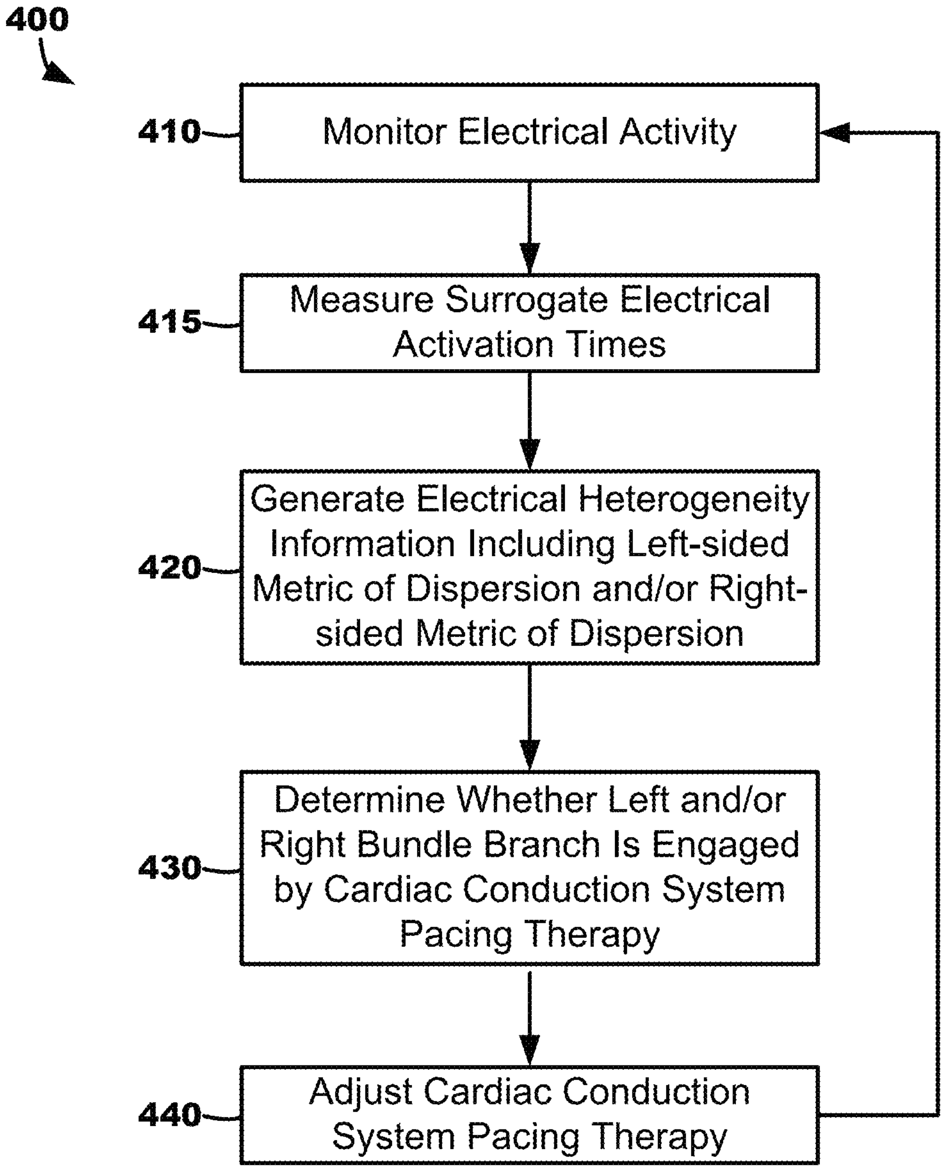
FIG. 4A is a block diagram of an illustrative method for determining whether the cardiac conduction system is engaged by cardiac conduction system pacing therapy.

An illustrative method 400 for determining whether a patient's cardiac conduction system is engaged by cardiac conduction system pacing therapy is depicted in FIG. 4A. As shown, the method 400 includes monitoring electrical activity 410 to generate a plurality of electrical signals (e.g., ECG or cardiac signals), each electrical signal of the plurality of electrical signals corresponding to each of the electrodes of the plurality of extra electrodes.

The electrical activity may be monitored during delivery of cardiac conduction system pacing therapy. The cardiac conduction system pacing therapy may include one or more electrodes positioned proximate one or more different locations of the cardiac conduction system such as, e.g., the bundle of His, the left bundle branch, the right bundle branch, intraseptal left ventricular endocardial area, etc., to deliver pacing pulses thereto. In one or more, embodiments, the cardiac conduction system may include electrodes positioned and configured to optionally stimulate one or both of the left bundle branch and the right bundle branch.

One example of cardiac conduction system pacing therapy may be ventricle-from-atrium (VfA) pacing therapy described and shown herein with respect to FIGS. 7-10. The VfA pacing therapy may be configured to deliver electrical paces to one or more areas of the cardiac conduction system including, but not limited to areas of the left bundle branches and the right bundle branches.

Another example of cardiac conduction system pacing therapy may be His bundle pacing therapy as, e.g., described in U.S. patent application Ser. No. 16/163,132 filed Oct. 17, 2018, entitled “His Bundle and Bundle Branch Pacing Adjustment,” which is incorporated herein by reference in its entirety. Still another example of cardiac conduction system pacing therapy may be intraseptal left ventricular endocardial pacing therapy as, e.g., described in U.S. Pat. No. 7,177,704 issued on Feb. 13, 2007, entitled “Pacing Method and Apparatus,” which is incorporated herein by reference in its entirety.

Thus, method 400 may be performed during or after the implantation of any cardiac conduction system pacing device. For example, the method 400 may be performed during an implantation of cardiac conduction system pacing device, e.g., to ensure that the cardiac conduction system pacing device has successfully or adequately engaged the cardiac conduction system or portion thereof being targeted during implantation and to adjust or configure such cardiac conduction system pacing therapy. Additionally, as described herein, monitoring electrical activity 410 using a plurality of external electrodes is a noninvasive process since, e.g., the external electrodes are attached to the skin of the patient as opposed to inserting or implanting any electrodes to acquire electrical activity or data.

According to various embodiments, the electrical activity is monitored 410 using a plurality of electrodes. The plurality of electrodes may be external surface electrodes configured in a band or a vest similar to as described herein with respect to FIGS. 1-3. Each of the electrodes may be positioned or located about the torso of the patient so as to monitor electrical activity (e.g., acquire torso-potentials) from a plurality of different locations about the torso of the patient. Each of the different locations where the electrodes are located may correspond to the electrical activation of different portions or regions of cardiac tissue of the patient’s heart. Thus, for example, the plurality of electrodes may record, or monitor, the electrical signals associated with the depolarization and repolarization of a plurality of different locations of, or about, the heart after the signals have propagated through the torso of a patient. According to various embodiments, the plurality of external electrodes may include, or comprise, a plurality of anterior electrodes that are located proximate skin of the anterior of the patient’s torso, left lateral or left side electrodes that are located proximate skin of the left lateral or left side of the patient’s torso, right lateral or right side electrodes that are located proximate skin of the right lateral or right side of the patient’s torso, and posterior electrodes that are located proximate skin of the posterior of the patient’s torso.

It may be described that, when using a plurality of external electrodes, the monitoring process 410 may provide a plurality electrocardiograms (ECGs), signals representative of the depolarization and repolarization of the patient’s heart. The plurality of ECGs may, in turn, be used to generate surrogate cardiac electrical activation times 415 representative of the depolarization of the heart. As described herein, surrogate cardiac electrical activation times may be, for example, representative of actual, or local, electrical activation times of one or more regions of the patient’s heart. Measurement of activation times can be performed by picking an appropriate fiducial point (e.g., peak values, minimum values, minimum slopes, maximum slopes, zero crossings, threshold crossings, etc. of a near or far-field EGM) and measuring time between the onset of cardiac depolarization (e.g., onset of QRS complexes) and the appropriate fiducial point (e.g., within the electrical activity). The activation time between the onset of the QRS complex (or the peak Q wave) to the fiducial point may be referred to as q-LV time. In at least one embodiment, the earliest QRS onset from all of the plurality of electrodes may be utilized as the starting point for each activation time for each electrode, and the maximum slope following the onset of the QRS complex may be utilized as the end point of each activation time for each electrode.

The monitored electrical activity 410 and, in turn, the electrical activation times 415 may be used to generate electrical heterogeneity information (EHI) 420. The EHI (e.g., data) may be defined as information indicative of at least one of mechanical synchrony or dyssynchrony of the heart and/or electrical synchrony or dyssynchrony of the heart. In other words, EHI may represent a surrogate of actual mechanical and/or electrical functionality of a patient’s heart. In at least one embodiment, relative changes in EHI (e.g., from baseline heterogeneity information to therapy heterogeneity information, from a first set of heterogeneity information to a second set of therapy heterogeneity information, etc.) may be used to determine a surrogate value representative of the changes in hemodynamic response (e.g., acute changes in LV pressure gradients). Left ventricular pressure may be typically monitored invasively with a pressure sensor located in the left ventricular of a patient’s heart. As such, the use of EHI to determine a surrogate value representative of the left ventricular pressure may avoid invasive monitoring using a left ventricular pressure sensor.

In at least one embodiment, the EHI may include a standard deviation of ventricular activation times measured using some or all of the external electrodes, e.g., of the electrode apparatus 110 described herein with respect FIGS. 1-3. Further, local, or regional, EHI may include standard deviations and/or averages of activation times measured using electrodes located in certain anatomic areas of the torso. For example, external electrodes on the left side of the torso of a patient may be used to compute local, or regional, left-sided EHI. Further, for example, external electrodes on the right side of the torso of a patient may be used to compute local, or regional, right-sided EHI.

The EHI may be generated using one or more various systems and/or methods. For example, EHI may be generated using an array, or a plurality, of surface electrodes and/or imaging systems as described in U.S. Pat. No. 9,510,763 B2 issued on Dec. 6, 2016, and entitled “ASSESSING INRA-CARDIAC ACTIVATION PAT- TERNS AND ELECTRICAL DYSSYNCHRONY," U.S. Pat. No. 8,972,228 B2 issued Mar. 3, 2015, and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

EHI may include one or more metrics or indices. In one or more embodiments, the one or more metrics or indices may be grouped as local or global. Local metrics or indices may be generated based on a subset of all external electrodes, if such external electrodes are spaced or positioned around the entire torso of the patient. Global metrics or indices may be generated based on all external electrodes. For example, one of the global metrics, or indices, of electrical heterogeneity may be a standard deviation of activation times (SDAT) measured using all of the electrodes on the surface of the torso of a patient. In some examples, the SDAT may be calculated using the surrogate, or estimated, cardiac activation times over the surface of a model heart.

In this example, the EHI also includes one or more local metrics such as a left, or left-sided, metric of dispersion generated based on left-sided activation times of the surrogate cardiac electrical activation times measured using a plurality of left external electrodes and/or a right, or right-sided, metric of dispersion generated based on right-sided activation times of the surrogate cardiac electrical activation times measured using a plurality of right external electrodes.

The left-sided metric of dispersion may be determined (e.g., calculated, computed, etc.) from electrical activity measured only by electrodes proximate the left side of the patient, which may be referred to as "left" electrodes. Surrogate cardiac activation times determined, or measured, from the left electrodes may be described as being left-sided activation times. The left electrodes may be defined as any surface electrodes located proximate the left ventricle, which includes the body or torso regions to the left of the patient's sternum and spine (e.g., toward the left arm of the patient, the left side of the patient, etc.). In one embodiment, the left electrodes may include all anterior electrodes on the left of the sternum and all posterior electrodes to the left of the spine. In another embodiment, the left electrodes may include all anterior electrodes on the left of the sternum and all posterior electrodes. In yet another embodiment, the left electrodes may be designated based on the contour of the left side of the heart as determined using imaging apparatus (e.g., x-ray, fluoroscopy, etc.).

The right-sided metric of dispersion may be determined (e.g., calculated, computed, etc.) from electrical activity measured only by electrodes proximate the right side of the patient, which may be referred to as "right" electrodes. Surrogate cardiac electrical activation times determined, or measured, from the right electrodes may be described as being right-sided activation times. The right electrodes may be defined as any surface electrodes located proximate the right ventricle, which includes the body or torso regions to the right of the patient's sternum and spine (e.g., toward the right arm of the patient, the right side of the patient, etc.). In one embodiment, the right electrodes may include all anterior electrodes on the right of the sternum and all posterior electrodes to the right of the spine. In another embodiment, the right electrodes may include right anterior electrodes on the right of the sternum and all posterior electrodes. In yet another embodiment, the right electrodes may be designated based on the contour of the right side of the heart as determined using imaging apparatus (e.g., x-ray, fluoroscopy, etc.).

An illustrative left, or left-sided, metric of dispersion may be a left standard deviation of surrogate cardiac electrical activation times monitored by the left external electrodes. Likewise, an illustrative right, or right-sided metric, of dispersion may be a right standard deviation of surrogate cardiac electrical activation times monitored by the right external electrodes. Other metrics of dispersion may include range, difference between earliest and latest activation times, interquartile differences (e.g., difference between 75th percentile of activation time and 25th percentile of activation times), and mean deviation defined by the mean of absolute differences between each activation time from the mean activation time. Such other metrics of dispersion may be applied to a set of activation times representative of left or right-sided activation. In other words, such other metrics of dispersion may be local metrics of dispersion.

The illustrative method 400 may then determine whether the patient's cardiac conduction system is engaged by the cardiac conduction system pacing therapy 430. In other words, the illustrative method 400 may determine whether the cardiac conduction system pacing therapy is adequately entering the cardiac conduction system so as to benefit the patient.

Figure 4B:
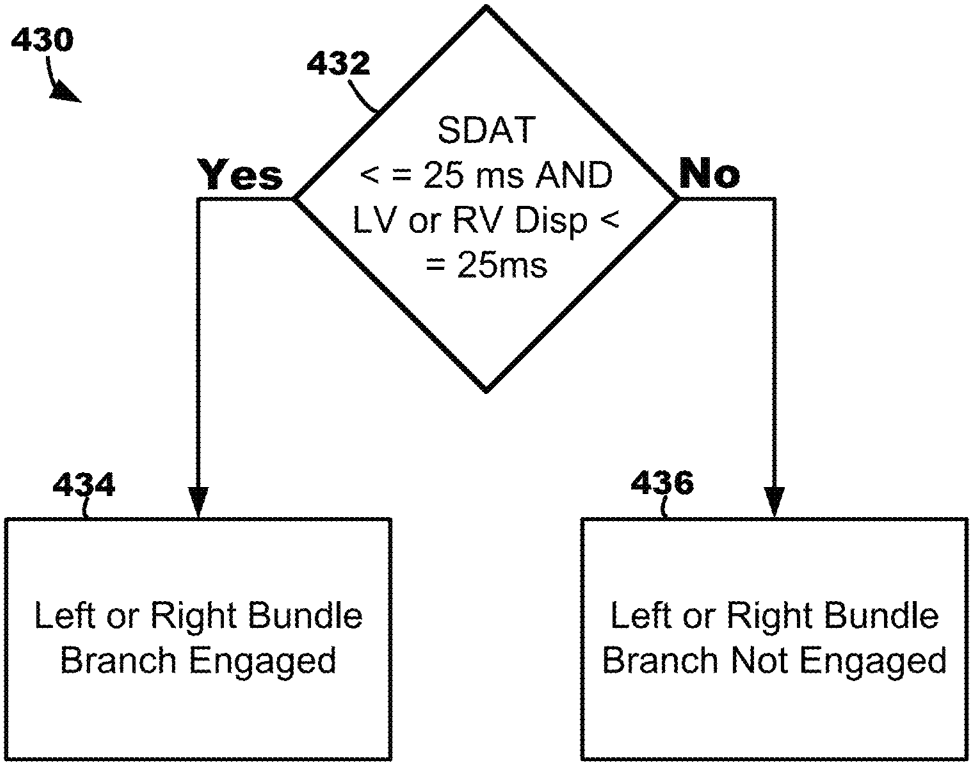
FIG. 4B is a detailed block diagram of an illustrative process of determining cardiac conduction system engagement of the method depicted in FIG. 4A.

The determination of whether the patient's cardiac conduction system is engaged by the cardiac conduction system pacing therapy 430 may be based on the generated EHI such as one or more global metrics (e.g., such as SDAT) and one or more local metrics (e.g. such as a left, or left-sided, metric of dispersion or right, or right-sided, metric of dispersion). Details regarding one illustrative method 430 of determining whether cardiac conduction system engagement is shown in FIG. 4B. In particular, as shown in FIG. 4B, if the SDAT is less than or equal to a global threshold value (in this example, 25 milliseconds (ms)) and the right-sided or left-sided metric of dispersion (e.g., standard deviation) is less than or equal to a local dispersion threshold value (in this example, also 25 ms) 432, then it may be determined that the cardiac conduction system is engaged 434. Conversely, if one of the SDAT is greater than the global threshold value and the right-sided or left-sided metric of dispersion (e.g., standard deviation) is greater than the local dispersion threshold value 432, then it may be determined that the cardiac conduction system is not engaged 436.

As shown in this example, the global dispersion threshold value may be 25 ms. The global dispersion threshold value may be between about 15 ms and about 50 ms. In one or more embodiment, the global dispersion threshold value is greater than or equal to 15 ms, greater than or equal to 20 ms, greater than or equal to 25 ms, etc. and/or less than or equal to 50 ms, less than or equal to 40 ms, less than or equal to 35 ms, less than or equal to 30 ms, etc.

As shown in this example, the local dispersion threshold value may be 25 ms. The local dispersion threshold value may be between about 15 ms and about 50 ms. In one or more embodiment, the local dispersion threshold value is greater than or equal to 15 ms, greater than or equal to 20 ms, greater than or equal to 25 ms, etc. and/or less than or equal to 50 ms, less than or equal to 40 ms, less than or equal to 35 ms, less than or equal to 30 ms, etc.

Further, although both a global and a local metric of dispersion are utilized in the determination of whether a patient's cardiac conduction system is engaged by cardiac conduction system pacing therapy in the example depicted in FIGS. 4A-4B, it is to be understood that only the global metric of dispersion or only the local metric of dispersion may be utilized to determine whether a patient's cardiac conduction system is engaged by cardiac conduction system pacing therapy. For example, in at least on embodiment, only the left-sided metric of dispersion such as the standard deviation of the surrogate cardiac electrical activation times measured by the left external electrodes may be used to determine whether the left bundle branch of a patient's cardiac conduction system is engaged by cardiac conduction system pacing therapy.

As noted in FIGS. 4A-4B, the portion of the cardiac conduction system that may be evaluated for engagement may be one or both of the left bundle branch and right bundle branch. When determining whether the left bundle branch is engaged by cardiac conduction system pacing therapy, the left-sided, or left, metrics of dispersion (e.g., left-sided standard deviation of surrogate cardiac electrical activation times) may be evaluated by processes 430, 432, and when determining whether the right bundle branch is engaged by cardiac conduction system pacing therapy, the right-sided, or right, metrics of dispersion (e.g., right-sided standard deviation of surrogate cardiac electrical activation times) may be evaluated by processes 430, 432.

Additionally, it is to be understood that determining whether the cardiac conduction system is engaged by the cardiac conduction system pacing therapy 430 may not necessarily be a binary, or yes-or-no, determination, and instead, may be a likelihood of cardiac conduction system pacing therapy engagement. For instance, the likelihood of cardiac conduction system pacing therapy engagement may be expressed, or represented, by a percentage or through descriptors such as, e.g., "cardiac conduction system highly likely engaged by cardiac conduction system pacing therapy," "cardiac conduction system likely engaged by cardiac conduction system pacing therapy," "cardiac conduction system unlikely to be engaged by cardiac conduction system pacing therapy," and "cardiac conduction system highly unlikely to be engaged by cardiac conduction system pacing therapy."

Further, configuring cardiac conduction system pacing therapy may be challenging. For example, often small locations within the cardiac conduction system network are targeted by the cardiac conduction system pacing therapy, which may be difficult to target when implanting a pacing electrode. Further, for example, the settings (e.g., pulse widths, timing, etc.) of the cardiac conduction system pacing therapy may be also be challenging to determine. Thus, determining whether the patient's cardiac conduction system is engaged by the cardiac conduction system pacing therapy 430 may be used to position and/or configure such cardiac conduction system pacing therapy.

Thus, the method 400 further includes adjusting, or modifying, the cardiac conduction system pacing therapy 440 if, for example, the cardiac conduction system is not engaged as determined in 430 to attempt to ensure engagement of the cardiac conduction system. Additionally, the method 400 may further include adjusting, or modifying, the cardiac conduction system pacing therapy 440 to optimize the cardiac conduction system pacing therapy to provide effective heart functionality. The method 400 may adjust the cardiac conduction system pacing therapy 440 in various ways. For example, the cardiac conduction system pacing therapy may include, or define, a plurality of different pacing settings, or parameters, that may be adjusted. The plurality of pacing settings may include, but not be limited to, pacing electrode location, angle of insertion through the atrioventricular (AV) groove, pacing electrode angle, pacing amplitude or power, pacing voltage, pacing polarity, pacing times such as A-V delay (e.g., timing of a V-pacing relative to intrinsic or paced atrial timing), V-V delay, pacing rate, and pacing pulse length, use of one or more pacing electrodes (e.g., number of pacing electrodes used), and use of one or more pacing vectors. In other words, one or more of the pacing settings may be changed (e.g., increase, decreased, moved, etc.) during adjustment of the cardiac conduction system pacing therapy 440.

After adjusting the cardiac conduction system pacing therapy 440, the method 400 may return to monitoring electrical activity 410, measuring surrogate cardiac electrical activation times 415, generating EHI 420 from the electrical activity monitored during the newly-adjusted cardiac conduction system pacing therapy, and determine cardiac conduction system engagement 430. In at least one embodiment, the method 400 may continue adjusting the cardiac conduction system pacing therapy until cardiac conduction system engagement is achieved. In at least another embodiment, the method 400 may continue to adjust the cardiac conduction system pacing therapy 440, and continue looping, until a plurality of different cardiac conduction system pacing therapy configurations, each having at least one different pacing parameter, have been attempted. In one embodiment, the pacing settings may be adjusted incrementally by steps or percentages in a way that "sweeps" across a range of possible parameters for each particular setting. For example, A-V delay may start at a level equal to 70% of patient's intrinsic A-V delay and may be progressively decreased in steps of about 10 ms to about 20 ms until a predefined minimum of 60 ms. Additionally, for example, the paced setting may be location or angle of the pacing electrode, and the location or angle of the pacing electrode may be adjusted incrementally by an implanter to provide a range of different locations and angles.

It may be described that method 400 defines a "closed-loop." For example, the processes of method 400 may continue looping for a plurality of different pacing settings or configurations, and for each of the plurality of different pacing settings or configurations, EHI information may be generated 430 and it may be determined whether such different pacing setting or configuration successfully engages the cardiac conduction system 440. If the different pacing setting or configuration does not engage the cardiac conduction system 440, then the method 400 may continue adjusting 440.

Furthermore, the method 400 may continue looping, even after finding a pacing setting or configuration that engages the cardiac conduction system to determine selected pacing settings for the cardiac conduction system pacing therapy that may, in some embodiments, be referred to as the "optimal" pacing settings as, for example, the pacing settings providing the most effective cardiac functionality may be selected. It is to be understood, however, the pacing settings providing the most effective cardiac functionality may not necessarily be the pacing settings that would be selected as considerations other than cardiac functionality exist such as, for example, battery life of the device performing the therapy. Thus, the selected, or optimal, pacing settings for the cardiac conduction system pacing therapy may represented a balance of many factors including cardiac functionality.

Figure 5A:
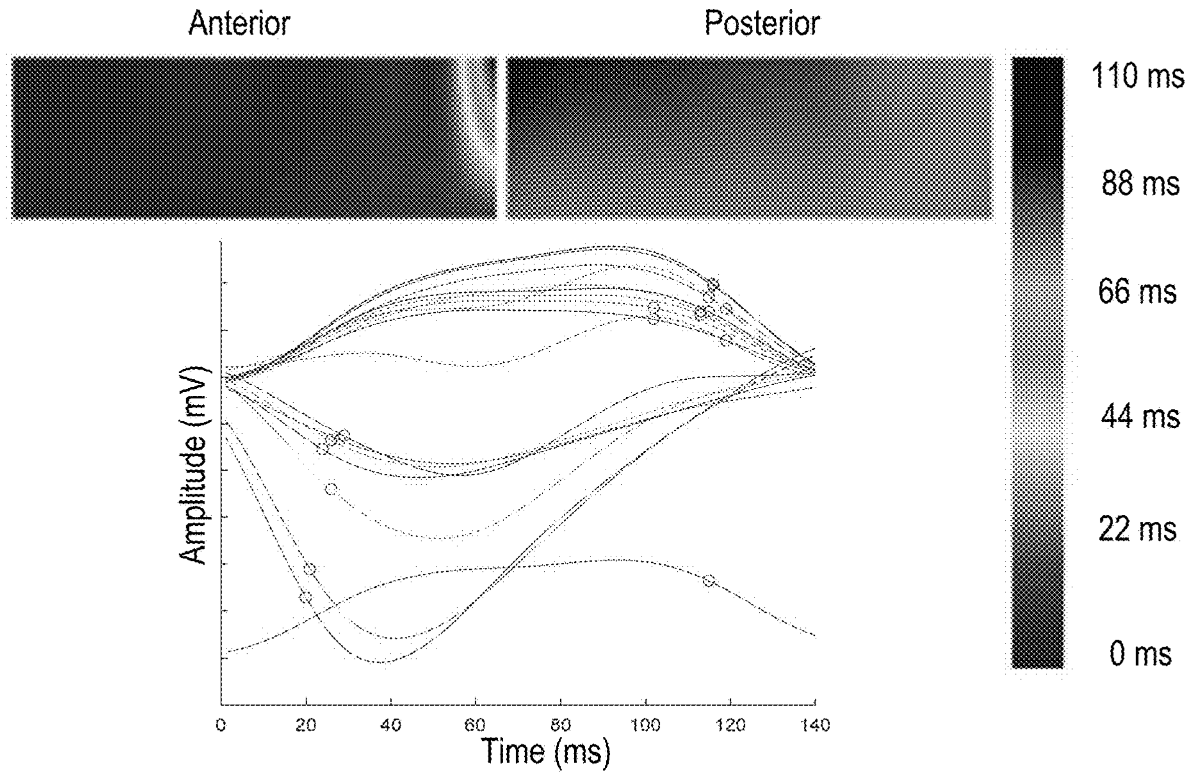
FIG. 5A depicts anterior and posterior surrogate cardiac electrical activation maps and a graph of surrogate cardiac electrical signals during intrinsic activation of a patient and a left bundle branch block.
Figure 5B:
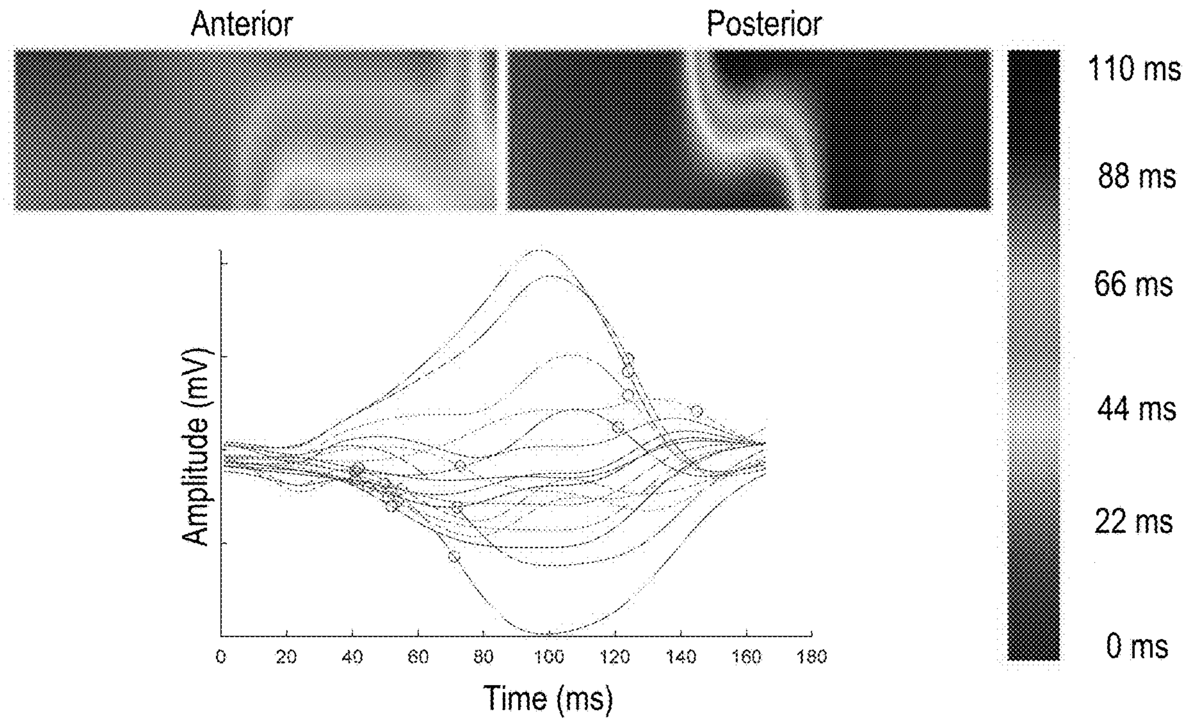
FIG. 5B depicts anterior and posterior surrogate cardiac electrical activation maps and a graph of surrogate cardiac electrical signals monitored during delivery of biventricular cardiac pacing therapy to the patient to treat the left bundle branch block.
Figure 5C:
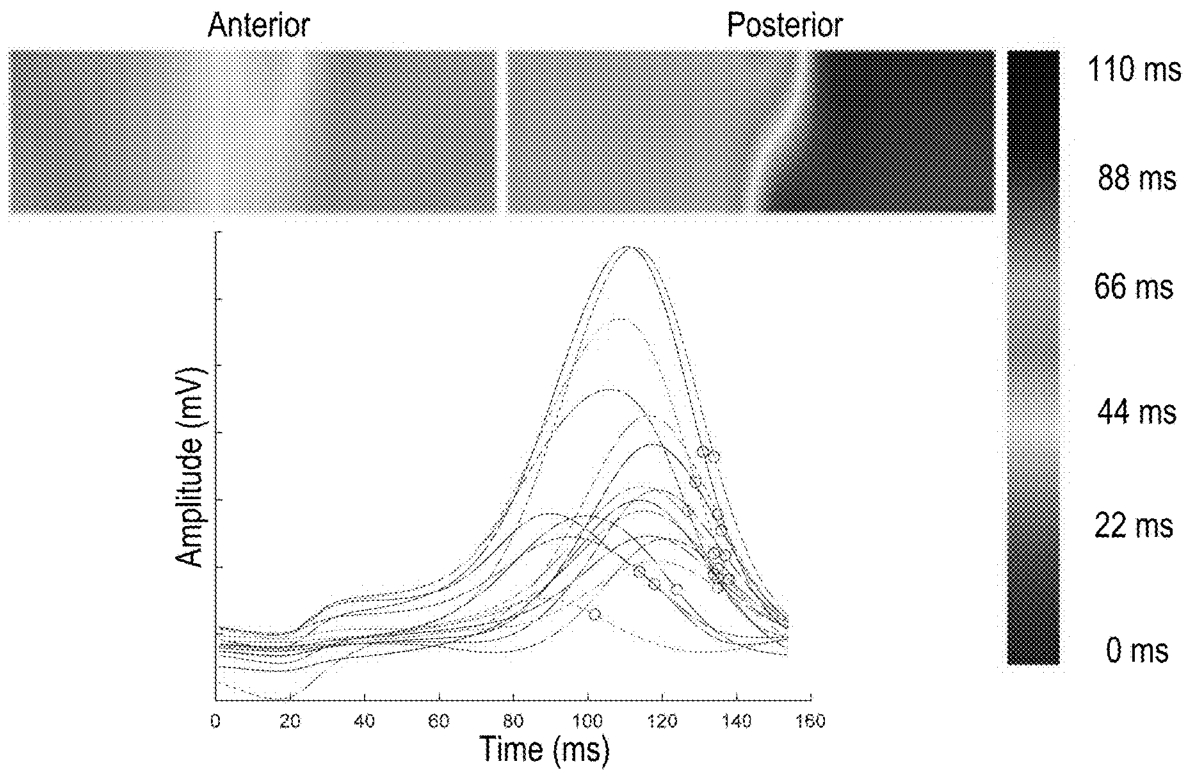
FIG. 5C depicts anterior and posterior surrogate cardiac electrical activation maps and a graph of surrogate cardiac electrical signals monitored during delivery of His bundle pacing therapy to the patient to treat the left bundle branch block.

Anterior and posterior surrogate cardiac electrical activation maps and graph of surrogate cardiac electrical signals monitored during intrinsic activation of a patient having a left bundle branch block, during delivery of biventricular cardiac pacing therapy to the patient to treat the left bundle branch block, and during delivery of His bundle pacing therapy to the patient to treat the left bundle branch block are depicted in FIGS. 5A-5C, respectively. During intrinsic activation as shown in FIG. 5A, the QRS duration was 165 ms, the SDAT was 41 ms, and the left-sided standard deviation of left-sided surrogate cardiac electrical activation times was 44 ms. During delivery of conventional biventricular pacing therapy as shown in FIG. 5B, the QRS duration was 127 ms, the SDAT was 33 ms, and the left-sided standard deviation of left-sided surrogate cardiac electrical activation times was 39 ms. During delivery of His bundle pacing as shown in FIG. 5C, the QRS duration was 110 ms, the SDAT was 25 ms, and the left-sided standard deviation of left-sided surrogate cardiac electrical activation times was 10 ms.

As can been seen from the examples of FIGS. 5A-5C, the left-sided metric of dispersion, namely, left-sided standard deviation of left-sided surrogate cardiac electrical activation times, was markedly lower during His bundle pacing therapy than intrinsic activation or conventional biventricular pacing therapy. Additionally, the global metric of dispersion, namely SDAT, was also lower during His bundle pacing therapy than intrinsic activation or conventional biventricular pacing therapy. Thus, the illustrative systems and methods described herein, which may utilize one or both of a local metric of dispersion and a global metric of dispersion, may identify that the His bundle pacing therapy depicted in FIG. 5C as engaged the patient's cardiac conduction system (in this example, the left bundle branch).

Figure 6A:
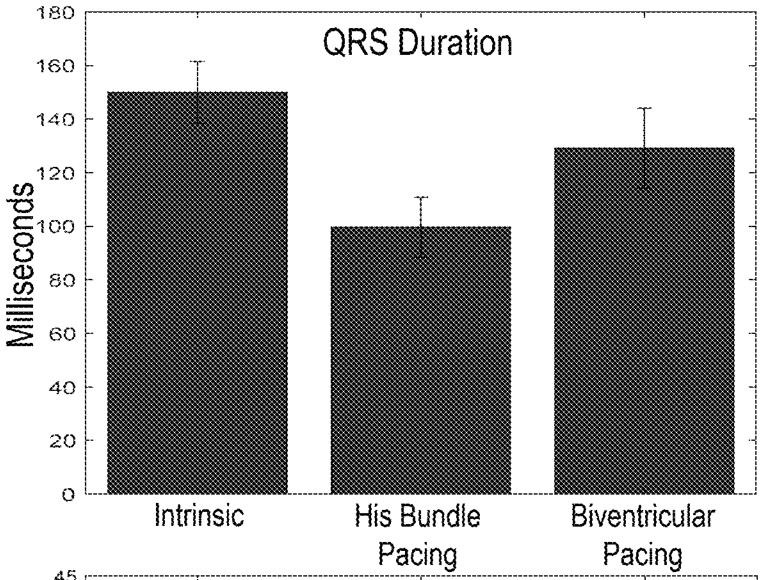
FIG. 6A illustrates bar graphs of QRS duration for 9 different patients during intrinsic activation, delivery of His bundle pacing therapy, and during delivery of biventricular cardiac pacing therapy.
Figure 6B:
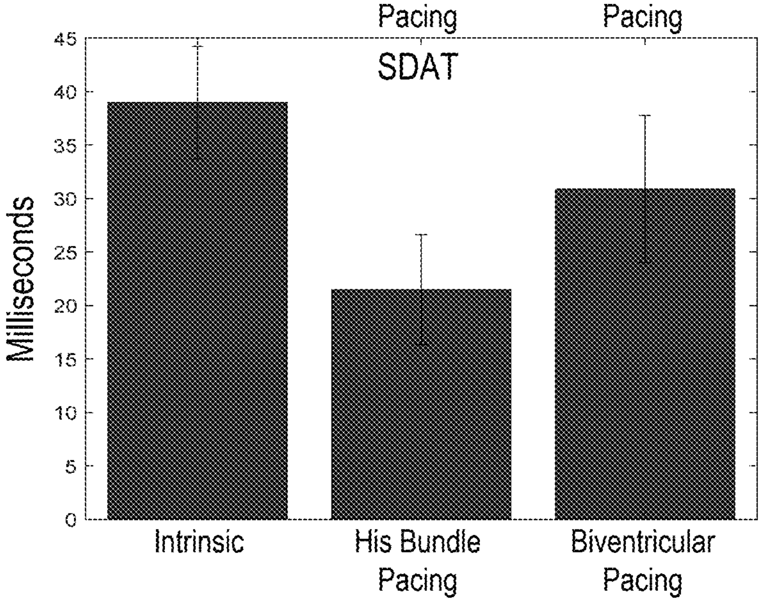
FIG. 6B illustrates bar graphs of a standard deviation of surrogate cardiac electrical activation times monitored by all of a plurality of external electrodes for 9 different patients during intrinsic activation, delivery of His bundle pacing therapy, and during delivery of biventricular cardiac pacing therapy.
Figure 6C:
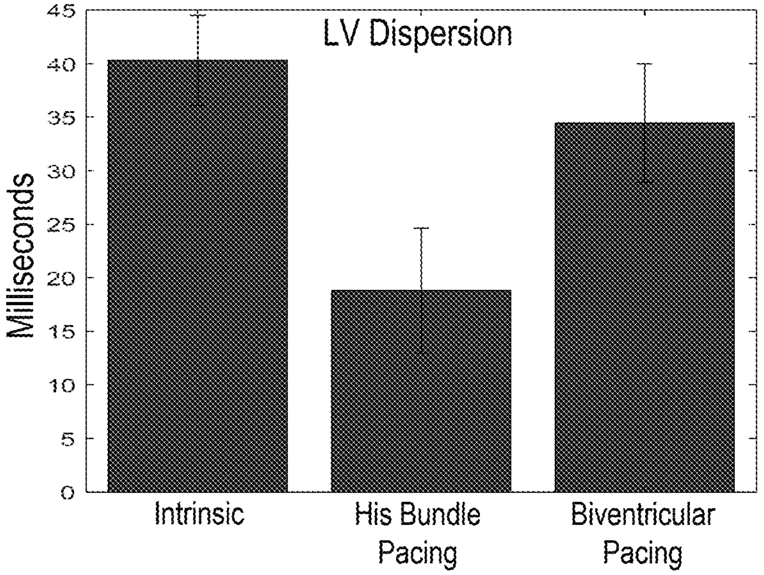
FIG. 6C illustrates bar graphs of a metric of left-sided dispersion monitored by a plurality of left-sided external electrodes for 9 different patients during intrinsic activation, delivery of His bundle pacing therapy, and during delivery of biventricular cardiac pacing therapy.

Each of FIGS. 6A-6C illustrates bar graphs of a different metric for 9 different patients during intrinsic activation, delivery of His bundle pacing therapy, and during delivery of biventricular cardiac pacing therapy. In particular, QRS duration is depicted in FIG. 6A, SDAT is depicted in FIG. 6B, and left-sided standard deviation of left-sided surrogate cardiac electrical activation times duration (LV Dispersion) is depicted in FIG. 6C.

The p-value between the conventional biventricular pacing and the His bundle pacing for QRS duration was 0.012. The p-value between the conventional biventricular pacing and the His bundle pacing for SDAT was also 0.012. The p-value between the conventional biventricular pacing and the His bundle pacing for left-sided standard deviation of left-sided surrogate cardiac electrical activation times markedly lower being less than 0.00005 indicating that left-sided standard deviation may be very discriminatory for determining whether the cardiac conduction system engaged (as opposed to such pacing therapy being delivered directly to myocardial tissue that is not part of the cardiac conduction system of the patient's heart such that, e.g., electrical activation propagates from one myocardial cell to another myocardial cell). In other words, the left-sided dispersion during successful His bundle pacing therapy being significantly lower than the conventional biventricular pacing therapy suggests engagement of the left bundle as a potential mechanism to better correct electrical dyssynchrony.

As described herein, the illustrative systems and methods may assist a user (e.g., clinician, doctor, etc.) to determine whether a patient may benefit from cardiac conduction system pacing therapy and/or determine the location of cardiac conduction system block within or along the cardiac conduction network. In one or more embodiments, illustrative cardiac conduction system pacing therapy may utilize any implantable or non-implantable cardiac pacing system intended to pace or deliver electrical paces to one or more areas or regions of the cardiac conduction system of the patient. The cardiac conduction system pacing therapy may use a single pacing electrode defining a single pacing vector or a plurality of pacing electrodes defining a plurality of pacing vectors.

Figure 7:
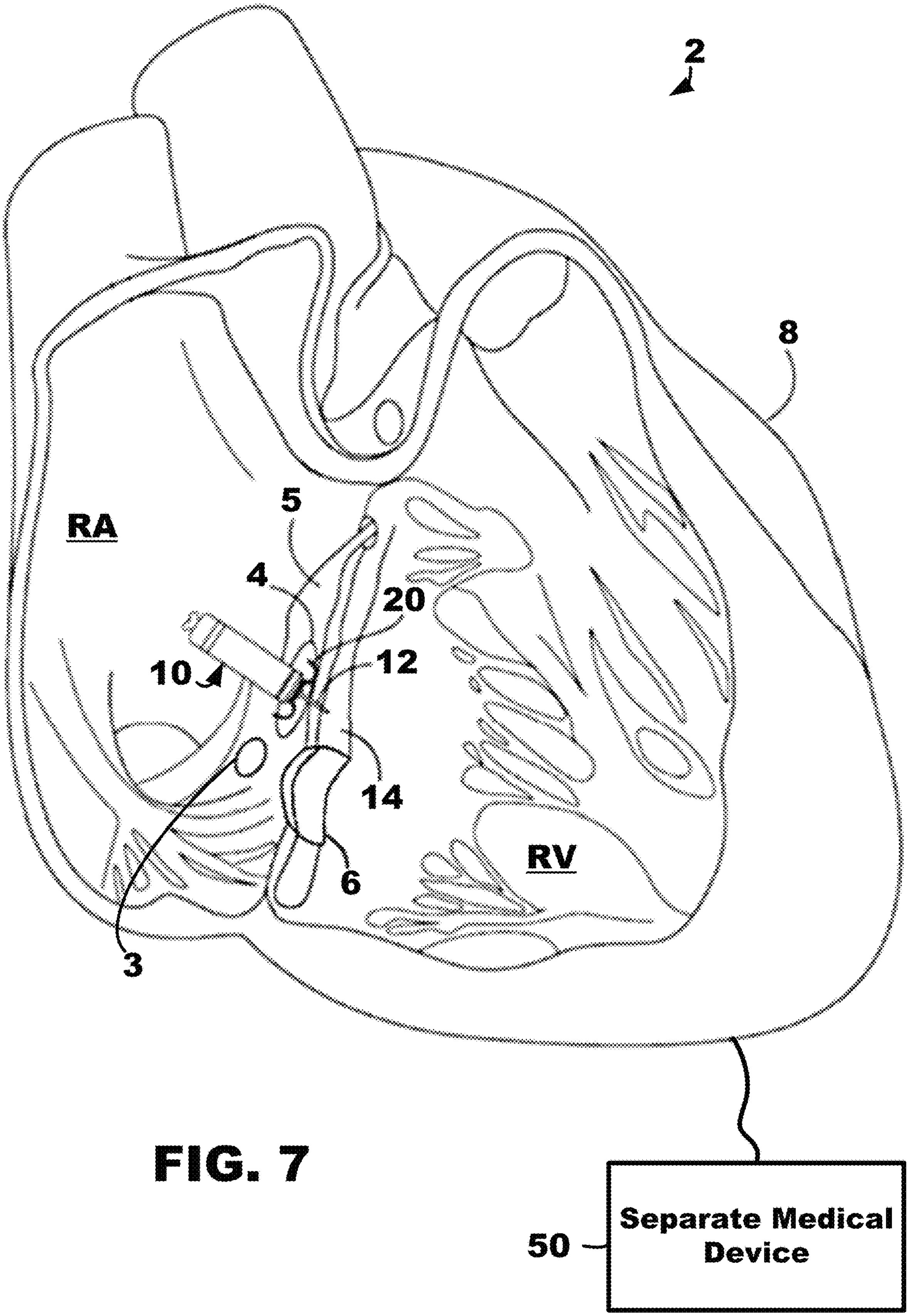
FIG. 7 is a conceptual diagram of an illustrative cardiac therapy system including an intracardiac medical device implanted in a patient's heart and a separate medical device positioned outside of the patient's heart.

An illustrative ventricle from atrium (VfA) cardiac therapy system is depicted in FIG. 7 that may be configured to be used with, for example, the systems and methods described herein with respect to FIGS. 1-6. Although it is to be understood that the present disclosure may utilize one or both of leadless and leaded implantable medical devices, the illustrative cardiac therapy system of FIG. 7 includes a leadless intracardiac medical device 10 that may be configured for single or dual chamber therapy and implanted in a patient's heart 8. In some embodiments, the device 10 may be configured for single chamber pacing and may, for example, switch between single chamber and multiple chamber pacing (e.g., dual or triple chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device 10 against the atrial endocardium in a target implant region 4. The target implant region 4 may lie between the Bundle of His 5 and the coronary sinus 3 and may be adjacent, or next to, the tricuspid valve 6. The device 10 may be described as a ventricle-from-atrium device because, for example, the device 10 may perform, or execute, one or both of sensing electrical activity from and providing therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right atrial endocardium and central fibrous body.

The device 10 may be described as a leadless implantable medical device. As used herein, "leadless" refers to a device being free of a lead extending out of the patient's heart 8. Further, although a leadless device may have a lead, the lead would not extend from outside of the patient's heart to inside of the patient's heart or would not extend from inside of the patient's heart to outside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from a distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at a distal end region of the shaft such that the electrode may be positioned within the ventricular myocardium for sensing ventricular signals and delivering ventricular pacing pulses (e.g., to depolarize the left ventricle and/or right ventricle to initiate a contraction of the left ventricle and/or right ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual or triple chamber pacing), single chamber pacing with multiple chamber sensing, single chamber pacing and/or sensing, or other clinical therapy and applications as appropriate.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 7), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical-pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 8:
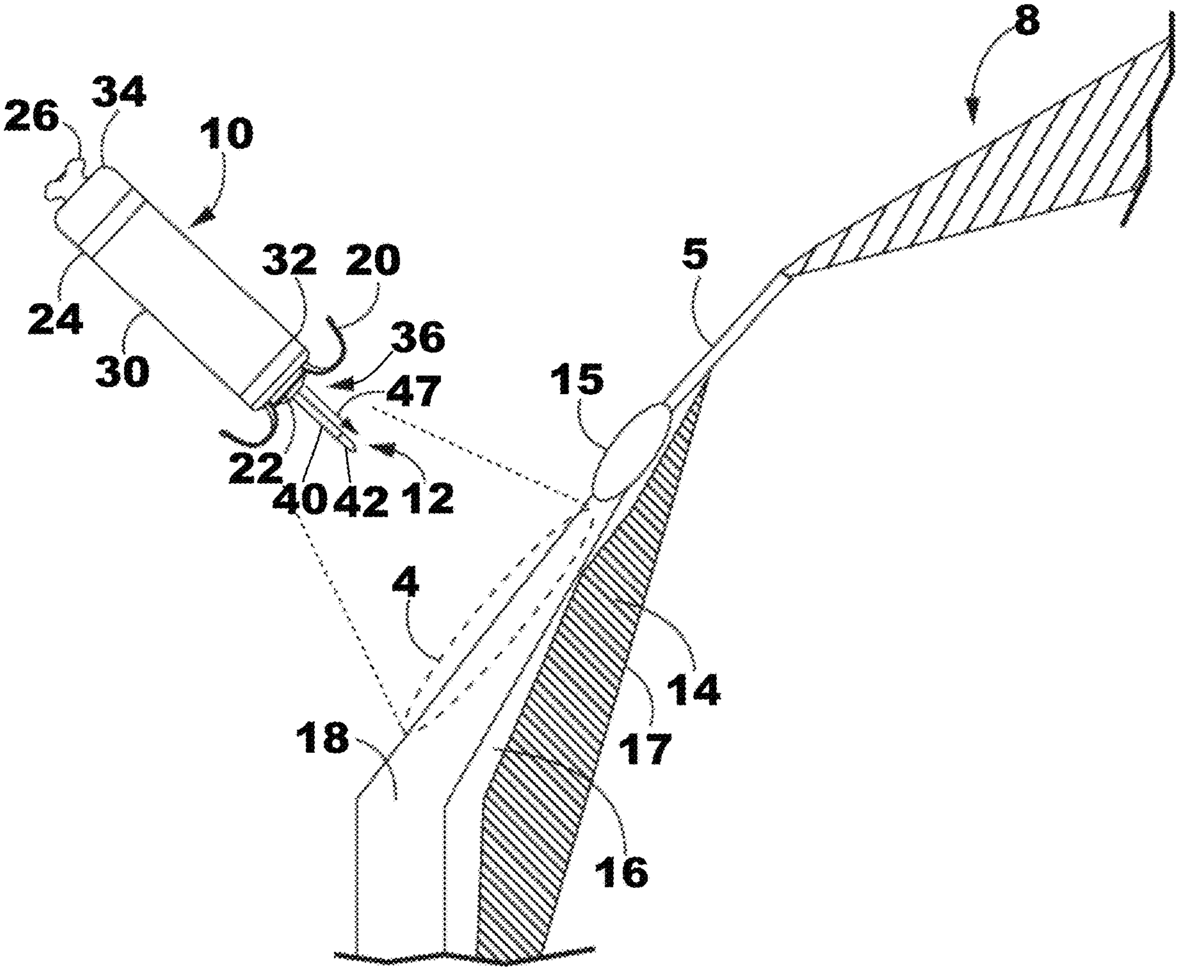
FIG. 8 is an enlarged conceptual diagram of the intracardiac medical device of FIG. 7 and anatomical structures of the patient's heart.

FIG. 8 is an enlarged conceptual diagram of the intracardiac medical device 10 of FIG. 7 and anatomical structures of the patient's heart 8. In particular, the device 10 is configured to sense cardiac signals and/or deliver pacing therapy. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 10. The housing 30 may include (e.g., be formed of or from) an electrically conductive material such as, e.g., titanium or titanium alloy, stainless steel, MP35N (a non-magnetic nickel-cobalt-chromium-molybdenum alloy), platinum alloy, or other bio-compatible metal or metal alloy. In other examples, the housing 30 may include (e.g., be formed of or from) a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 and as defining a generally-cylindrical shape, e.g., to facilitate catheter delivery. In other embodiments, the housing 30 may be prismatic or any other shape to perform the functionality and utility described herein. The housing 30 may include a delivery tool interface member 26, e.g., defined, or positioned, at the proximal end region 34, for engaging with a delivery tool during implantation of the device 10.

All or a portion of the housing 30 may function as a sensing and/or pacing electrode during cardiac therapy. In the example shown, the housing 30 includes a proximal housing-based electrode 24 that circumscribes a proximal portion (e.g., closer to the proximal end region 34 than the distal end region 32) of the housing 30. When the housing 30 is (e.g., defines, formed from, etc.) an electrically-conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to form, or define, the proximal housing-based electrode 24. When the housing 30 is (e.g., defines, formed from, etc.) a non-conductive material, such as a ceramic, glass or polymer material, an electrically-conductive coating or layer, such as a titanium, platinum, stainless steel, or alloys thereof, may be applied to one or more discrete areas of the housing 30 to form, or define, the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32, and therefore, may be referred to as a proximal housing-based electrode 24. In other examples, however, the proximal housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one such example as shown, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemi-spherical distal tip with a relatively narrow tip-diameter (e.g., less than about 1 millimeter (mm)) for penetrating into and through tissue layers without using a sharpened tip or needle-like tip having sharpened or beveled edges.

The dart electrode assembly 12 may be configured to pierce through one or more tissue layers to position the tip electrode 42 within a desired tissue layer such as, e.g., the ventricular myocardium. As such, the height 47, or length, of the shaft 40 may correspond to the expected pacing site depth, and the shaft 40 may have a relatively-high compressive strength along its longitudinal axis to resist bending in a lateral or radial direction when pressed against and into the implant region 4. If a second dart electrode assembly 12 is employed, its length may be unequal to the expected pacing site depth and may be configured to act as an indifferent electrode for delivering of pacing energy to and/or sensing signals from the tissue. In one embodiment, a longitudinal axial force may be applied against the tip electrode 42, e.g., by applying longitudinal pushing force to the proximal end 34 of the housing 30, to advance the dart electrode assembly 12 into the tissue within the target implant region.

The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. Thus, the dart electrode assembly 12 including the shaft 40 may be described as being resilient. When the shaft 40 is not exposed to any external force, or to only a force along its longitudinal central axis, the shaft 40 may retain a straight, linear position as shown.

In other words, the shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by a height, or length, 47 of the shaft 40.

The one or more fixation members 20 may be described as one or more "tines" having a normally curved position. The tines may be held in a distally extended position within a delivery tool. The distal tips of tines may penetrate the heart tissue to a limited depth before elastically, or resiliently, curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual or triple chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of tip electrode 42 and shaft 40 from about 3 mm to about 8 mm in various examples. The diameter of the shaft 40 may be less than about 2 mm, and may be about 1 mm or less, or even about 0.6 mm or less.

Figure 9:
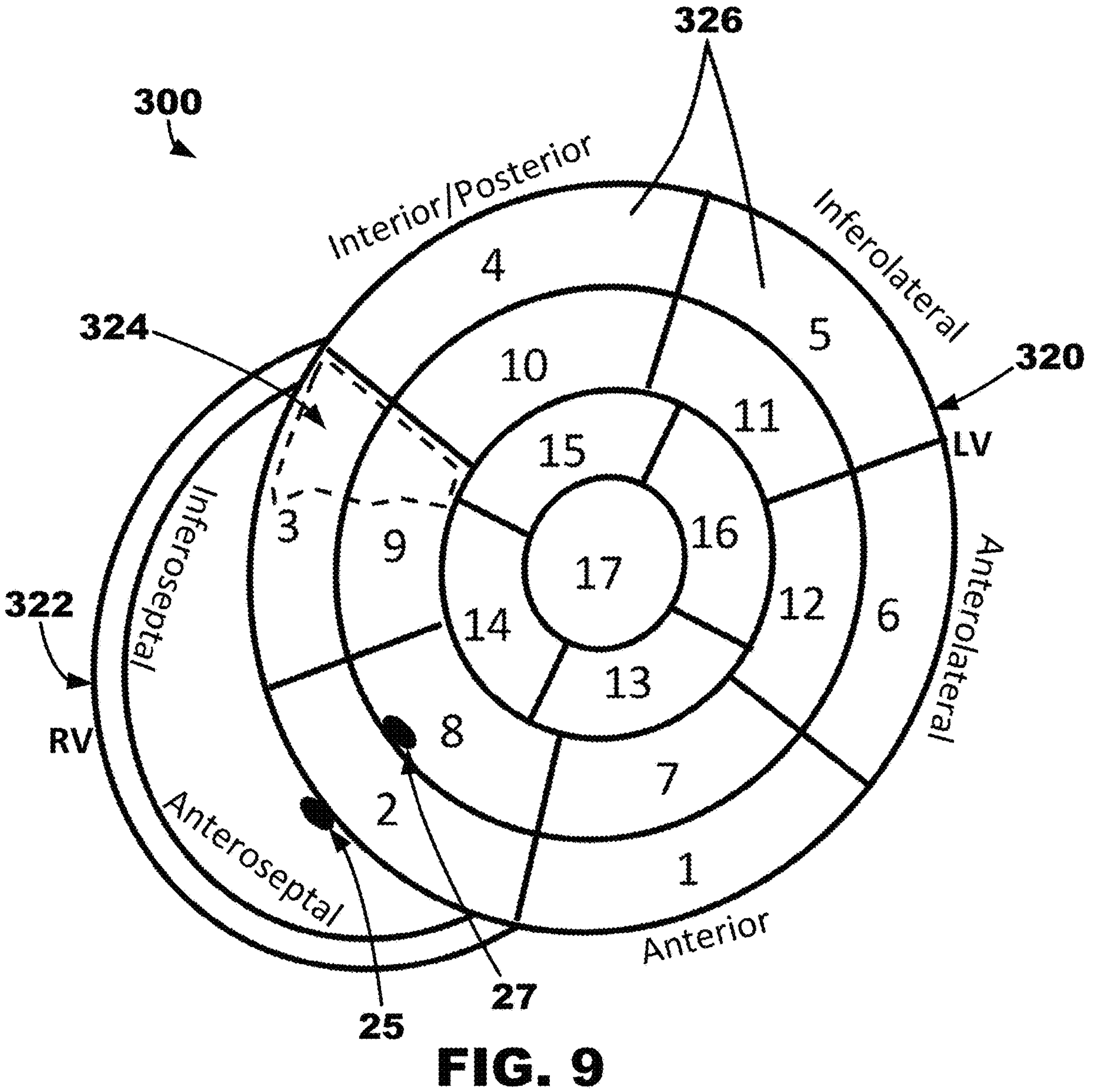
FIG. 9 is a conceptual diagram of a map of a patient's heart in a standard 17 segment view of the left ventricle showing various electrode implantation locations for use with the illustrative systems and devices described herein.

FIG. 9 is a two-dimensional (2D) ventricular map 300 of a patient's heart (e.g., a top-down view) showing the left ventricle 320 in a standard 17 segment view and the right ventricle 322. The map 300 defines, or includes, a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) 25 and left bundle branch (LBB) 27.

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body. Once implanted, the tissue-piercing electrode may be positioned in the target implant region 4 (FIGS. 7-8), such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 3 and mid-inferoseptal area 9 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 10:
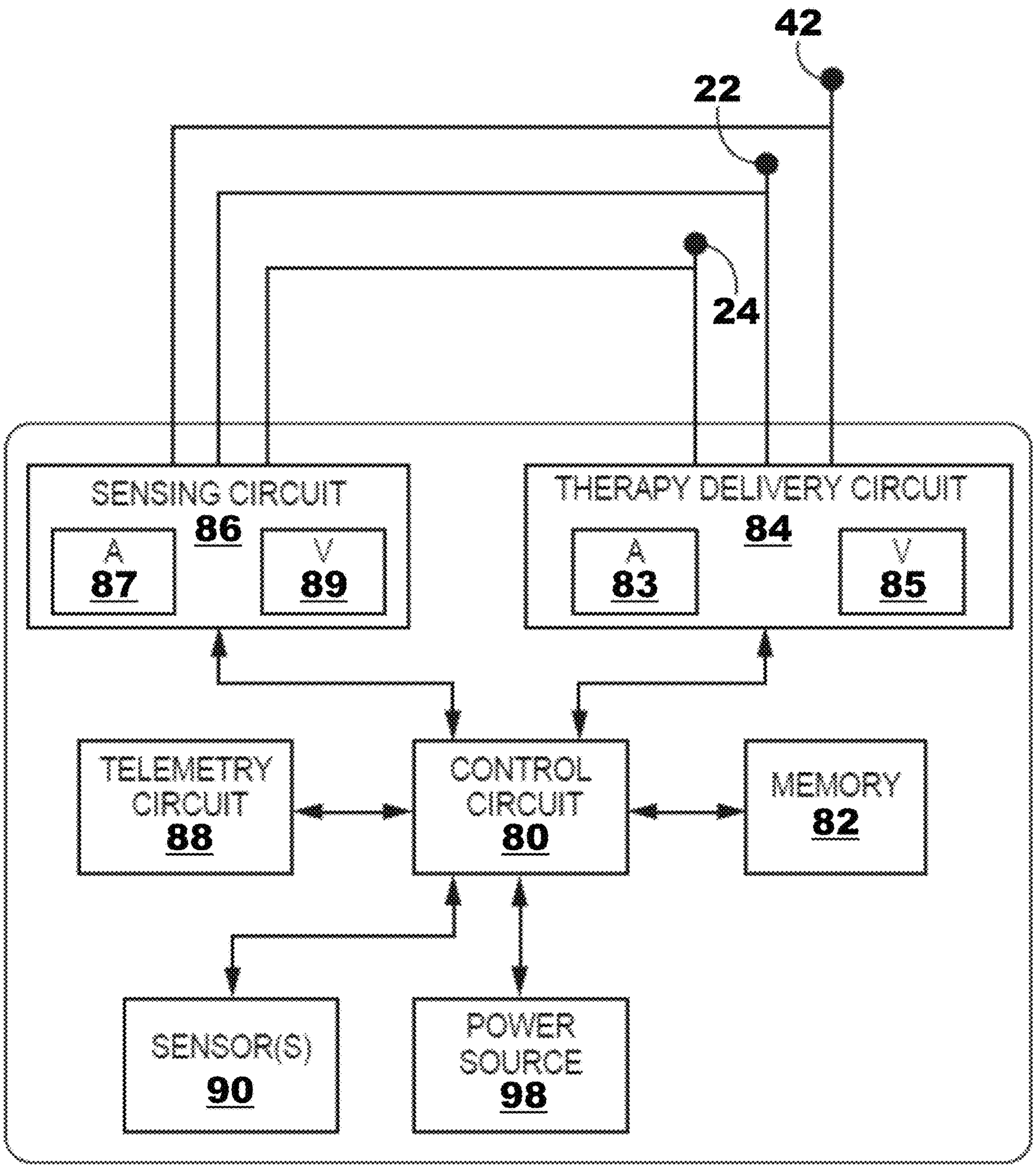
FIG. 10 is a block diagram of illustrative circuitry that may be enclosed within the housing of the medical devices of FIGS. 7-8, for example, to provide the functionality and therapy described herein.

A block diagram of circuitry is depicted in FIG. 10 that may be enclosed within the housings 30 of the device 10 to provide the functions of sensing cardiac signals, determining capture, and/or delivering pacing therapy according to one example or within the housings of any other medical devices described herein. The separate medical device 50 as shown in FIG. 7 may include some or all the same components, which may be configured in a similar manner. The electronic circuitry enclosed within the housing 30 may include software, firmware, and hardware that cooperatively monitor atrial and ventricular electrical cardiac signals, determine whether cardiac system capture has occurred, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing signals that are correlated to one or more physiological functions, states, or conditions of the patient. For example, the sensor(s) 90 may include a patient activity sensor, for use in determining a need for pacing therapy and/or controlling a pacing rate. In other words, the device 10 may include other sensors 90 for sensing signals from the patient for use in determining whether to deliver and/or controlling electrical stimulation therapies delivered by the therapy delivery circuit 84.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components 80, 82, 84, 86, 88, 90 may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown in FIG. 10 represent functionality included in the device 10 and may include any discrete and/or integrated electronic circuit components that implement analog, and/or digital circuits capable of producing the functions attributed to the medical device 10 described herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer readable media storing instructions that, when executed by one or more processing circuits, cause the control circuit 80 and/or other processing circuitry to determine posterior left bundle branch engagement and/or perform a single, dual, or triple chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (A-V) pacing interval. If an R-wave is sensed before the A-V pacing interval expires, the ventricular pacing pulse may be inhibited. If the A-V pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 42 and the proximal housing-based electrode 24 may be coupled to the ventricular pacing circuit 85 as a bipolar cathode and anode pair for delivering ventricular pacing pulses, e.g., upon expiration of an A-V or V-V pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set one or more atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 87. The control circuit 80 starts an A-V pacing interval in response to a delivered atrial pacing pulse to provide synchronized multiple chamber pacing (e.g., dual or triple chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single chamber or multiple chamber pacing (e.g., dual or triple chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

The techniques described in this disclosure, including those attributed to the IMD 10, device 50, the computing apparatus 140, and the computing device 160 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

All references and publications cited herein are expressly incorporated herein by reference in their entirety for all purposes, except to the extent any aspect incorporated directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a first medical device may be operatively coupled to another medical device to transmit information in the form of data or to receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all the listed elements or a combination of at least two of the listed elements. The phrases "at least one of," "comprises at least one of," and "one or more of" followed by a list refers to any one of the items in the list and any combination of two or more items in the list.

ILLUSTRATIVE EMBODIMENTS

Embodiment 1: A system comprising:

an electrode apparatus comprising a plurality of external electrodes to be disposed proximate a patient's skin, wherein the plurality of external electrodes comprise a plurality of left external electrodes positioned to the left side of the patient's torso; and a computing apparatus comprising processing circuitry, the computing apparatus operably coupled to the electrode apparatus and configured to:

measure surrogate cardiac electrical activation times using the plurality external electrodes of the electrode apparatus during delivery of cardiac conduction system pacing therapy, wherein the surrogate cardiac electrical activation times are representative of depolarization of cardiac tissue that propagates through the torso of the patient, generate electrical heterogeneity information (EHI) based on the measured surrogate cardiac electrical activation times during delivery of the cardiac conduction system pacing therapy, wherein the EHI comprises a left-sided metric of dispersion based on the surrogate cardiac electrical activation times measured using the plurality of left external electrodes, and determine whether a left bundle branch of the cardiac conduction system is engaged by the cardiac conduction system pacing therapy based on the left-sided metric of dispersion.

Embodiment 2: A method comprising:

measuring surrogate cardiac electrical activation times using a plurality external electrodes disposed proximate a patient's skin during delivery of cardiac conduction system pacing therapy, wherein the plurality of external electrodes comprise a plurality of left external electrodes positioned to the left side of the patient's torso, wherein the surrogate cardiac electrical activation times are representative of depolarization of cardiac tissue that propagates through the torso of the patient;

generating electrical heterogeneity information (EHI) based on the measured surrogate cardiac electrical activation times during delivery of the cardiac conduction system pacing therapy, wherein the EHI comprises a left-sided metric of dispersion based on the surrogate cardiac electrical activation times measured using the plurality of left external electrodes; and determining whether a left bundle branch of the cardiac conduction system is engaged by the cardiac conduction system pacing therapy based on the left-sided metric of dispersion.

Embodiment 3: The system or method as set forth in any one of embodiment 1 and embodiment 2, wherein the left-sided metric of dispersion comprises a left-sided standard deviation of surrogate cardiac electrical activation times measured using the plurality of left external electrodes.

Embodiment 4: The systems or methods as set forth in embodiment 3, wherein determining whether a left bundle branch of the cardiac conduction system is engaged by the cardiac conduction system pacing therapy based on the left-sided metric of dispersion comprises comparing the left-sided standard deviation to a local dispersion threshold value.

Embodiment 5: The systems or methods as set forth in embodiment 4, wherein the local dispersion threshold value is less than or equal to 25 milliseconds.

Embodiment 6: The systems or methods as set forth in any one of embodiments 1-5, wherein the EHI further comprises a global metric of dispersion of all activation times based on the surrogate cardiac electrical activation times measured using all of the plurality of external electrodes, wherein determining whether a left bundle branch of the cardiac conduction system is engaged by the cardiac conduction system pacing therapy is also based on the global metric of dispersion of all activation times.

Embodiment 7: The systems or methods as set forth in any one of embodiments 1-6, wherein the computing apparatus is further configured to adjust one or more paced settings of the cardiac conduction system pacing therapy if the left bundle branch of the cardiac conduction system is not determined to be engaged.

Embodiment 8: The systems or methods as set forth in embodiment 7, wherein the one or more paced settings comprise at least one of a voltage, a pulse width, timing of a V-pacing relative to intrinsic or paced atrial timing, pacing rate, a location of at least one implantable electrode, angle of insertion through the atrioventricular (AV) groove, a pacing polarity, a pacing vector, and a number of pacing electrodes used.

Embodiment 9: The systems or methods as set forth in any one of embodiments 1-8, wherein measuring surrogate cardiac electrical activation times using the plurality external electrodes of the electrode apparatus during delivery of cardiac conduction system pacing therapy comprises measuring surrogate cardiac electrical activation times during delivery of cardiac conduction system pacing therapy at a plurality of different paced settings, wherein generating EHI based on the monitored electrical activity during delivery of the cardiac conduction system pacing therapy comprises generating EHI for each different paced settings of the plurality of different paced settings, and wherein determining whether a left bundle branch of the cardiac conduction system is engaged by the cardiac conduction system pacing therapy based on the left-sided metric of dispersion comprises determining whether a left bundle branch of the cardiac conduction system is engaged by the cardiac conduction system pacing therapy based on the left-sided metric of dispersion for each different paced settings of the plurality of different paced settings.

Embodiment 10: The systems or methods as set forth in any one of embodiments 1-9, wherein the cardiac conduction system pacing therapy comprises ventricle from atrium (VfA) pacing therapy, wherein the VfA pacing therapy is delivered using a tissue-piercing electrode implantable from the triangle of Koch region of the right atrium through the right atrial endocardium and central fibrous body.

Embodiment 11: The systems or methods as set forth in any one of embodiments 1-10, wherein the cardiac conduction system pacing therapy comprises one or more of His bundle pacing therapy, left bundle branch area pacing, and intraseptal left ventricular endocardial pacing.

Embodiment 12: A system comprising:

an electrode apparatus comprising a plurality of external electrodes to be disposed proximate a patient's skin, wherein the plurality of external electrodes comprise a plurality of right external electrodes positioned to the right side of the patient's torso; and a computing apparatus comprising processing circuitry, the computing apparatus operably coupled to the electrode apparatus and configured to:

measure surrogate cardiac electrical activation times using the plurality external electrodes of the electrode apparatus during delivery of cardiac conduction system pacing therapy, wherein the surrogate cardiac electrical activation times are representative of depolarization of cardiac tissue that propagates through the torso of the patient, generate electrical heterogeneity information (EHI) based on the measured surrogate cardiac electrical activation times during delivery of the cardiac conduction system pacing therapy, wherein the EHI comprises a right-sided metric of dispersion based on the surrogate cardiac electrical activation times measured using the plurality of right external electrodes, and determine whether a right bundle branch of the cardiac conduction system is engaged by the cardiac conduction system pacing therapy based on the right-sided metric of dispersion.

Embodiment 13: A method comprising:

measuring surrogate cardiac electrical activation times using a plurality external electrodes disposed proximate a patient's skin during delivery of cardiac conduction system pacing therapy, wherein the plurality of external electrodes comprise a plurality of right external electrodes positioned to the right side of the patient's torso, wherein the surrogate cardiac electrical activation times are representative of depolarization of cardiac tissue that propagates through the torso of the patient;

generating electrical heterogeneity information (EHI) based on the measured surrogate cardiac electrical activation times during delivery of the cardiac conduction system pacing therapy, wherein the EHI comprises a right-sided metric of dispersion based on the surrogate cardiac electrical activation times measured using the plurality of right external electrodes; and determining whether a right bundle branch of the cardiac conduction system is engaged by the cardiac conduction system pacing therapy based on the right-sided metric of dispersion.

Embodiment 14: The system or method as set forth in any one of embodiment 1 and embodiment 2, wherein the right-sided metric of dispersion comprises a right-sided standard deviation of surrogate cardiac electrical activation times measured using the plurality of right external electrodes.

Embodiment 15: The systems or methods as set forth in embodiment 14, wherein determining whether a right bundle branch of the cardiac conduction system is engaged by the cardiac conduction system pacing therapy based on the right-sided metric of dispersion comprises comparing the right-sided standard deviation to a local dispersion threshold value.

Embodiment 16: The systems or methods as set forth in embodiment 15, wherein the local dispersion threshold value is less than or equal to 25 milliseconds.

Embodiment 17: The systems or methods as set forth in any one of embodiments 12-16, wherein the EHI further comprises a global metric of dispersion of all activation times based on the surrogate cardiac electrical activation times measured using all of the plurality of external electrodes, wherein determining whether a right bundle branch of the cardiac conduction system is engaged by the cardiac conduction system pacing therapy is also based on the global metric of dispersion of all activation times.

Embodiment 18: The systems or methods as set forth in any one of embodiments 12-17, wherein the computing apparatus is further configured to adjust one or more paced settings of the cardiac conduction system pacing therapy if the right bundle branch of the cardiac conduction system is not determined to be engaged.

Embodiment 19: The systems or methods as set forth in embodiment 18, wherein the one or more paced settings comprise at least one of a voltage, a pulse width, timing of a V-pacing relative to intrinsic or paced atrial timing, pacing rate, a location of at least one implantable electrode, an angle of insertion through the atrioventricular (AV) groove. a pacing polarity, a pacing vector, and a number of pacing electrodes used.

Embodiment 20: The systems or methods as set forth in any one of embodiments 12-19, wherein measuring surrogate cardiac electrical activation times using the plurality external electrodes of the electrode apparatus during delivery of cardiac conduction system pacing therapy comprises measuring surrogate cardiac electrical activation times during delivery of cardiac conduction system pacing therapy at a plurality of different paced settings, wherein generating EHI based on the monitored electrical activity during delivery of the cardiac conduction system pacing therapy comprises generating EHI for each different paced settings of the plurality of different paced settings, and wherein determining whether a right bundle branch of the cardiac conduction system is engaged by the cardiac conduction system pacing therapy based on the right-sided metric of dispersion comprises determining whether a right bundle branch of the cardiac conduction system is engaged by the cardiac conduction system pacing therapy based on the right-sided metric of dispersion for each different paced settings of the plurality of different paced settings.

Embodiment 21: The systems or methods as set forth in any one of embodiments 12-20, wherein the cardiac conduction system pacing therapy comprises ventricle from atrium (VfA) pacing therapy, wherein the VfA pacing therapy is delivered using a tissue-piercing electrode implantable from the triangle of Koch region of the right atrium through the right atrial endocardium and central fibrous body.

Embodiment 22: The systems or methods as set forth in any one of embodiments 12-21, wherein the cardiac conduction system pacing therapy comprises one or more of His bundle pacing therapy and right bundle branch area pacing.

What is claimed:

1. A system to determine left bundle branch engagement by an implantable medical device delivering cardiac conduction system pacing therapy, the system comprising:

an electrode apparatus comprising a plurality of external electrodes to be disposed proximate a patient's skin, wherein the plurality of external electrodes comprise a plurality of left external electrodes adapted to be positioned to the left side of the patient's torso; and a computing apparatus comprising processing circuitry, the computing apparatus operably coupled to the electrode apparatus and configured to:

measure surrogate cardiac electrical activation times using the plurality external electrodes of the electrode apparatus during delivery of the cardiac conduction system pacing therapy by the implantable medical device, wherein the surrogate cardiac electrical activation times are representative of depolarization of cardiac tissue that propagates through the torso of the patient, generate electrical heterogeneity information (EHI) based on the measured surrogate cardiac electrical activation times during delivery of the cardiac conduction system pacing therapy by the implantable medical device, wherein the EHI comprises a left-sided metric of dispersion based on the surrogate cardiac electrical activation times measured using the plurality of left external electrodes, determine whether a left bundle branch of the cardiac conduction system is engaged by the cardiac conduction system pacing therapy for delivery by the implantable medical device based on the left-sided metric of dispersion, and adjusting one or more paced settings of the cardiac conduction system pacing therapy for delivery by the implantable medical device when the left bundle branch of the cardiac conduction system is not determined to be engaged.

2. The system of claim 1, wherein the left-sided metric of dispersion comprises a left-sided standard deviation of surrogate cardiac electrical activation times measured using the plurality of left external electrodes.

3. The system of claim 2, wherein determining whether a left bundle branch of the cardiac conduction system is engaged by the cardiac conduction system pacing therapy for delivery by the implantable medical device based on the left-sided metric of dispersion comprises comparing the left-sided standard deviation to a local dispersion threshold value.

4. The system of claim 3, wherein the local dispersion threshold value is less than or equal to 25 milliseconds.

5. The system of claim 1, wherein the EHI further comprises a global metric of dispersion of all activation times based on the surrogate cardiac electrical activation times measured using all of the plurality of external electrodes, wherein determining whether a left bundle branch of the cardiac conduction system is engaged by the cardiac conduction system pacing therapy for delivery by the implantable medical device is also based on the global metric of dispersion of all activation times.

6. The system of claim 1, wherein the one or more paced settings comprise at least one of a voltage, a pulse width, timing of a V-pacing relative to intrinsic or paced atrial timing, pacing rate, a location of at least one implantable electrode, angle of insertion through the atrioventricular (AV) groove, a pacing polarity, a pacing vector, and a number of pacing electrodes used.

7. The system of claim 1, wherein measuring surrogate cardiac electrical activation times using the plurality external electrodes of the electrode apparatus during the delivery of cardiac conduction system pacing therapy comprises measuring surrogate cardiac electrical activation times during delivery of the cardiac conduction system pacing therapy at a plurality of different paced settings, wherein generating EHI based on the measured surrogate cardiac electrical activation times during delivery of the cardiac conduction system pacing therapy comprises generating EHI for each different paced settings of the plurality of different paced settings, and wherein determining whether a left bundle branch of the cardiac conduction system is engaged by the cardiac conduction system pacing therapy based on the left-sided metric of dispersion comprises determining whether a left bundle branch of the cardiac conduction system is engaged by the cardiac conduction system pacing therapy based on the left-sided metric of dispersion for each different paced settings of the plurality of different paced settings.

8. The system of claim 1, wherein the cardiac conduction system pacing therapy for delivery by the implantable medical device comprises ventricle from atrium (VfA) pacing therapy, wherein the VfA pacing therapy is for delivery using a tissue-piercing electrode implantable from the triangle of Koch region of the right atrium through the right atrial endocardium and central fibrous body.

9. The system of claim 1, wherein the cardiac conduction system pacing therapy for delivery by the implantable medical device comprises one or more of His bundle pacing therapy, left bundle branch area pacing, and intraseptal left ventricular endocardial pacing.

10. A method of determining left bundle branch engagement by an implantable medical device delivering cardiac conduction system pacing therapy, the method comprising:

measuring surrogate cardiac electrical activation times using a plurality external electrodes disposed proximate a patient's skin during delivery of the cardiac conduction system pacing therapy by the implantable medical device, wherein the plurality of external electrodes comprise a plurality of left external electrodes adapted to be positioned to the left side of the patient's torso, wherein the surrogate cardiac electrical activation times are representative of depolarization of cardiac tissue that propagates through the torso of the patient;

generating electrical heterogeneity information (EHI) based on the measured surrogate cardiac electrical activation times during delivery of the cardiac conduction system pacing therapy by the implantable medical device, wherein the EHI comprises a left-sided metric of dispersion based on the surrogate cardiac electrical activation times measured using the plurality of left external electrodes;

determining whether a left bundle branch of the cardiac conduction system is engaged by the cardiac conduction system pacing therapy for delivery by the implantable medical device based on the left-sided metric of dispersion; and adjusting one or more paced settings of the cardiac conduction system pacing therapy for delivery by the implantable medical device when the left bundle branch of the cardiac conduction system is not determined to be engaged.

11. The method of claim 10, wherein the left-sided metric of dispersion comprises a left-sided standard deviation of surrogate cardiac electrical activation times measured using the plurality of left external electrodes.

12. The method of claim 11, wherein determining whether a left bundle branch of the cardiac conduction system is engaged by the cardiac conduction system pacing therapy for delivery by the implantable medical device based on the left-sided metric of dispersion comprises comparing the left-sided standard deviation to a local dispersion threshold value.

13. The method of claim 12, wherein the local dispersion threshold value is less than or equal to 25 milliseconds.

14. The method of claim 10, wherein the EHI further comprises a global metric of dispersion of all activation times based on the surrogate cardiac electrical activation times measured using all of the plurality of external electrodes, wherein determining whether a left bundle branch of the cardiac conduction system is engaged by the cardiac conduction system pacing therapy for delivery by the implantable medical device is also based on the global metric of dispersion of all activation times.

15. The method of claim 10, wherein the one or more paced settings comprise at least one of a voltage, a pulse width, timing of a V-pacing relative to intrinsic or paced atrial timing, pacing rate, a location of at least one implantable electrode, angle of insertion through the atrioventricular (AV) groove, a pacing polarity, a pacing vector, and a number of pacing electrodes used.

16. The method of claim 10, wherein measuring surrogate cardiac electrical activation times using the plurality external electrodes during delivery of cardiac conduction system pacing therapy for delivery by the implantable medical device comprises measuring surrogate cardiac electrical activation times during delivery of the cardiac conduction system pacing therapy at a plurality of different paced settings, wherein generating EHI based on the measured surrogate cardiac electrical activation times during delivery of the cardiac conduction system pacing therapy comprises generating EHI for each different paced settings of the plurality of different paced settings, and wherein determining whether a left bundle branch of the cardiac conduction system is engaged by the cardiac conduction system pacing therapy for delivery by the implantable medical device based on the left-sided metric of dispersion comprises determining whether a left bundle branch of the cardiac conduction system is engaged by the cardiac conduction system pacing therapy based on the left-sided metric of dispersion for each different paced settings of the plurality of different paced settings.

17. The method of claim 10, wherein the cardiac conduction system pacing therapy for delivery by the implantable medical device comprises ventricle from atrium (VfA) pacing therapy, wherein the VfA pacing therapy is for delivery using a tissue-piercing electrode implantable from the triangle of Koch region of the right atrium through the right atrial endocardium and central fibrous body.

18. The method of claim 10, wherein the cardiac conduction system pacing therapy for delivery by the implantable medical device comprises one or more of His bundle pacing therapy, left bundle branch area pacing, and intraseptal left ventricular endocardial pacing.

19. A system to determine right bundle branch engagement by an implantable medical device delivering cardiac conduction system pacing therapy, the system comprising:

an electrode apparatus comprising a plurality of external electrodes to be disposed proximate a patient's skin, wherein the plurality of external electrodes comprise a plurality of right external electrodes adapted to be positioned to the right side of the patient's torso;

and a computing apparatus comprising processing circuitry, the computing apparatus operably coupled to the electrode apparatus and configured to:

measure surrogate cardiac electrical activation times using the plurality external electrodes of the electrode apparatus during delivery of the cardiac conduction system pacing therapy, wherein the surrogate cardiac electrical activation times are representative of depolarization of cardiac tissue that propagates through the torso of the patient, generate electrical heterogeneity information (EHI) based on the measured surrogate cardiac electrical activation times during delivery of the cardiac conduction system pacing therapy, wherein the EHI comprises a right-sided metric of dispersion based on the surrogate cardiac electrical activation times measured using the plurality of right external electrodes, determine whether a right bundle branch of the cardiac conduction system is engaged by the cardiac conduction system pacing therapy for delivery by the implantable medical device based on the right-sided metric of dispersion, and adjust one or more paced settings of the cardiac conduction system pacing therapy for delivery by the implantable medical device when the right bundle branch of the cardiac conduction system is not determined to be engaged.

20. The system of claim 19, wherein the right-sided metric of dispersion comprises a right-sided standard deviation of surrogate cardiac electrical activation times measured using the plurality of right external electrodes.

21. The system of claim 20, wherein determining whether a right bundle branch of the cardiac conduction system is engaged by the cardiac conduction system pacing therapy for delivery by the implantable medical device based on the right-sided metric of dispersion comprises comparing the right-sided standard deviation to a local dispersion threshold value.

22. The system of claim 21, wherein the local dispersion threshold value is less than or equal to 25 milliseconds.

23. The system of claim 19, wherein the EHI further comprises a global metric of dispersion of all activation times based on the surrogate cardiac electrical activation times measured using all of the plurality of external electrodes, wherein determining whether a right bundle branch of the cardiac conduction system is engaged by the cardiac conduction system pacing therapy for delivery by the implantable medical device is also based on the global metric of dispersion of all activation times.

24. The system of claim 19, wherein the one or more paced settings comprise at least one of a voltage, a pulse width, timing of a V-pacing relative to intrinsic or paced atrial timing, pacing rate, a location of at least one implantable electrode, an angle of insertion through the atrioventricular (AV) groove, a pacing polarity, a pacing vector, and a number of pacing electrodes used.

25. The system of claim 19, wherein measuring surrogate cardiac electrical activation times using the plurality external electrodes of the electrode apparatus during delivery of cardiac conduction system pacing therapy comprises measuring surrogate cardiac electrical activation times during delivery of cardiac conduction system pacing therapy at a plurality of different paced settings, wherein generating EHI based on the measured surrogate cardiac electrical activation times during delivery of the cardiac conduction system pacing therapy comprises generating EHI for each different paced settings of the plurality of different paced settings, and wherein determining whether a right bundle branch of the cardiac conduction system is engaged by the cardiac conduction system pacing therapy for delivery by the implantable medical device based on the right-sided metric of dispersion comprises determining whether a right bundle branch of the cardiac conduction system is engaged by the cardiac conduction system pacing therapy based on the right-sided metric of dispersion for each different paced settings of the plurality of different paced settings.

26. The system of claim 19, wherein the cardiac conduction system pacing therapy for delivery by the implantable medical device comprises ventricle from atrium (VfA) pacing therapy, wherein the VfA pacing therapy is for delivery using a tissue-piercing electrode implantable from the triangle of Koch region of the right atrium through the right atrial endocardium and central fibrous body.

27. The system of claim 19, wherein the cardiac conduction system pacing therapy for delivery by the implantable medical device comprises one or more of His bundle pacing therapy and right bundle branch area pacing.

28. A method of determining right bundle branch engagement by an implantable medical device delivering cardiac conduction system pacing therapy, the method comprising:

measuring surrogate cardiac electrical activation times using a plurality external electrodes disposed proximate a patient's skin during delivery of the cardiac conduction system pacing therapy by the implantable medical device, wherein the plurality of external electrodes comprise a plurality of right external electrodes adapted to be positioned to the right side of the patient's torso, wherein the surrogate cardiac electrical activation times are representative of depolarization of cardiac tissue that propagates through the torso of the patient;

generating electrical heterogeneity information (EHI) based on the measured surrogate cardiac electrical activation times during delivery of the cardiac conduction system pacing therapy, wherein the EHI comprises a right-sided metric of dispersion based on the surrogate cardiac electrical activation times measured using the plurality of right external electrodes;

determining whether a right bundle branch of the cardiac conduction system is engaged by the cardiac conduction system pacing therapy for delivery by the implantable medical device based on the right-sided metric of dispersion; and adjusting one or more paced settings of the cardiac conduction system pacing therapy for delivery by the implantable medical device when the right bundle branch of the cardiac conduction system is not determined to be engaged.

29. The method of claim 28, wherein the right-sided metric of dispersion comprises a right-sided standard deviation of surrogate cardiac electrical activation times measured using the plurality of right external electrodes.

30. The method of claim 29, wherein determining whether a right bundle branch of the cardiac conduction system is engaged by the cardiac conduction system pacing therapy for delivery by the implantable medical device based on the right-sided metric of dispersion comprises comparing the right-sided standard deviation to a local dispersion threshold value.

31. The method of claim 30, wherein the local dispersion threshold value is less than or equal to 25 milliseconds.

32. The method of claim 28, wherein the EHI further comprises a global metric of dispersion of all activation times based on the surrogate cardiac electrical activation times measured using all of the plurality of external electrodes, wherein determining whether a right bundle branch of the cardiac conduction system is engaged by the cardiac conduction system pacing therapy is also based on the global metric of dispersion of all activation times.

33. The method of claim 28, wherein the one or more paced settings comprise at least one of a voltage, a pulse width, timing of a V-pacing relative to intrinsic or paced atrial timing, pacing rate, a location of at least one implantable electrode, angle of insertion through the atrioventricular (AV) groove, a pacing polarity, a pacing vector, and a number of pacing electrodes used.

34. The method of claim 28, wherein measuring surrogate cardiac electrical activation times using the plurality external electrodes during delivery of cardiac conduction system pacing therapy comprises measuring surrogate cardiac electrical activation times during delivery of the cardiac conduction system pacing therapy at a plurality of different paced settings, wherein generating EHI based on the measured surrogate cardiac electrical activation times during delivery of the cardiac conduction system pacing therapy comprises generating EHI for each different paced settings of the plurality of different paced settings, and wherein determining whether a right bundle branch of the cardiac conduction system is engaged by the cardiac conduction system pacing therapy for delivery by the implantable medical device based on the right-sided metric of dispersion comprises determining whether a right bundle branch of the cardiac conduction system is engaged by the cardiac conduction system pacing therapy for delivery by the implantable medical device based on the right-sided metric of dispersion for each different paced settings of the plurality of different paced settings.

35. The method of claim 28, wherein the cardiac conduction system pacing therapy for delivery by the implantable medical device comprises ventricle from atrium (VfA) pacing therapy, wherein the VfA pacing therapy is for delivery using a tissue-piercing electrode implantable from the triangle of Koch region of the right atrium through the right atrial endocardium and central fibrous body.

36. The method of claim 28, wherein the cardiac conduction system pacing therapy for delivery by the implantable medical device comprises one or more of His bundle pacing therapy, right bundle branch area pacing.

* * * * *